US010168525B2

(12) United States Patent
Kim et al.

(10) Patent No.: US 10,168,525 B2
(45) Date of Patent: Jan. 1, 2019

(54) MULTI-WELL FOURIER PTYCHOGRAPHIC AND FLUORESCENCE IMAGING

(71) Applicant: California Institute of Technology, Pasadena, CA (US)

(72) Inventors: Jinho Kim, Pasadena, CA (US); Changhuei Yang, Alhambra, CA (US)

(73) Assignee: California Institute of Technology, Pasadena, CA (US)

( * ) Notice: Subject to any disclaimer, the term of this patent is extended or adjusted under 35 U.S.C. 154(b) by 64 days.

(21) Appl. No.: 15/007,159

(22) Filed: Jan. 26, 2016

(65) Prior Publication Data

US 2016/0216208 A1    Jul. 28, 2016

Related U.S. Application Data

(60) Provisional application No. 62/107,631, filed on Jan. 26, 2015, provisional application No. 62/107,628, filed on Jan. 26, 2015.

(51) Int. Cl.
| | | |
|---|---|---|
| *G02B 21/36* | (2006.01) | |
| *G02B 21/16* | (2006.01) | |
| *G02B 21/00* | (2006.01) | |
| *G01N 21/64* | (2006.01) | |
| *H04N 5/225* | (2006.01) | |

(52) U.S. Cl.
CPC ....... *G02B 21/365* (2013.01); *G01N 21/6452* (2013.01); *G01N 21/6456* (2013.01); *G01N 21/6458* (2013.01); *G02B 21/0076* (2013.01); *G02B 21/16* (2013.01); *H04N 5/2258* (2013.01); *G01N 2021/6478* (2013.01); *G01N 2201/0446* (2013.01)

(58) Field of Classification Search
CPC .. G02B 21/365; G02B 21/0076; G02B 21/16; G01N 21/6456; G01N 21/6452; G01N 21/6458; G01N 2021/6478; G01N 2201/0446
USPC .......................................... 250/459.1, 458.1
See application file for complete search history.

(56) References Cited

U.S. PATENT DOCUMENTS

| | | | |
|---|---|---|---|
| 5,475,527 | A | 12/1995 | Hackel et al. |
| 6,144,365 | A | 11/2000 | Young et al. |
| 6,154,196 | A | 11/2000 | Fleck et al. |
| 6,320,174 | B1 | 11/2001 | Tafas et al. |
| 6,320,648 | B1 | 11/2001 | Brueck et al. |
| 6,747,781 | B2 | 6/2004 | Trisnadi |
| 6,905,838 | B1 | 6/2005 | Bittner |

(Continued)

FOREIGN PATENT DOCUMENTS

| | | |
|---|---|---|
| CN | 101408623 A | 4/2009 |
| CN | 101868740 A | 10/2010 |

(Continued)

OTHER PUBLICATIONS

U.S. Appl. No. 15/007,196, filed Jan. 26, 2016 entitled "Array Level Fourier Ptychographic Imaging".

(Continued)

*Primary Examiner* — Marcus Taningco
*Assistant Examiner* — Gisselle Guitierrez
(74) *Attorney, Agent, or Firm* — Sheila Martinez-Lemke; Weaver Austin Villeneuve & Sampson LLP

(57) ABSTRACT

Certain aspects pertain to multi-well systems, devices, and methods of Fourier ptychographic and fluorescence imaging.

36 Claims, 27 Drawing Sheets

(56) References Cited

U.S. PATENT DOCUMENTS

| | | | |
|---|---|---|---|
| 7,436,503 B1 | 10/2008 | Chen et al. | |
| 7,460,248 B2 | 12/2008 | Kurtz et al. | |
| 7,706,419 B2 | 4/2010 | Wang et al. | |
| 7,787,588 B1 | 8/2010 | Yun et al. | |
| 8,271,251 B2 | 9/2012 | Schwartz et al. | |
| 8,313,031 B2 | 11/2012 | Vinogradov | |
| 8,497,934 B2 | 7/2013 | Milnes et al. | |
| 8,624,968 B1 | 1/2014 | Zheng et al. | |
| 8,942,449 B2 | 1/2015 | Maiden | |
| 9,029,745 B2 | 5/2015 | Maiden | |
| 9,426,455 B2 | 8/2016 | Horstmeyer et al. | |
| 9,497,379 B2* | 11/2016 | Ou | G02B 21/084 |
| 9,829,695 B2 | 11/2017 | Kim et al. | |
| 9,864,184 B2 | 1/2018 | Ou et al. | |
| 9,892,812 B2 | 2/2018 | Zheng et al. | |
| 9,983,397 B2 | 5/2018 | Horstmeyer et al. | |
| 9,993,149 B2 | 6/2018 | Chung et al. | |
| 9,998,658 B2 | 6/2018 | Ou et al. | |
| 2001/0055062 A1 | 12/2001 | Shioda et al. | |
| 2002/0141051 A1 | 10/2002 | Vogt et al. | |
| 2003/0116436 A1 | 6/2003 | Amirkhanian et al. | |
| 2004/0057094 A1 | 3/2004 | Olszak et al. | |
| 2004/0146196 A1 | 7/2004 | Van Heel | |
| 2004/0190762 A1 | 9/2004 | Dowski, Jr. et al. | |
| 2005/0211912 A1* | 9/2005 | Fox | B82Y 10/00 |
| | | | 250/458.1 |
| 2006/0098293 A1 | 5/2006 | Garoutte et al. | |
| 2006/0158754 A1 | 7/2006 | Tsukagoshi et al. | |
| 2006/0173313 A1 | 8/2006 | Liu et al. | |
| 2006/0291707 A1 | 12/2006 | Kothapalli et al. | |
| 2007/0057184 A1 | 3/2007 | Uto et al. | |
| 2007/0133113 A1 | 6/2007 | Minabe et al. | |
| 2007/0159639 A1 | 7/2007 | Teramura et al. | |
| 2007/0171430 A1 | 7/2007 | Tearney et al. | |
| 2007/0189436 A1 | 8/2007 | Goto et al. | |
| 2008/0101664 A1 | 5/2008 | Perez | |
| 2008/0182336 A1 | 7/2008 | Zhuang et al. | |
| 2009/0046164 A1 | 2/2009 | Shroff et al. | |
| 2009/0079987 A1 | 3/2009 | Ben-Ezra et al. | |
| 2009/0125242 A1 | 5/2009 | Choi et al. | |
| 2009/0284831 A1 | 11/2009 | Schuster et al. | |
| 2009/0316141 A1 | 12/2009 | Feldkhun | |
| 2010/0135547 A1 | 6/2010 | Lee et al. | |
| 2010/0271705 A1 | 10/2010 | Hung | |
| 2011/0075928 A1 | 3/2011 | Jeong et al. | |
| 2011/0192976 A1 | 8/2011 | Own et al. | |
| 2011/0235863 A1 | 9/2011 | Maiden | |
| 2012/0069344 A1 | 3/2012 | Liu | |
| 2012/0099803 A1 | 4/2012 | Ozcan et al. | |
| 2012/0105618 A1 | 5/2012 | Brueck et al. | |
| 2012/0118967 A1 | 5/2012 | Gerst | |
| 2012/0157160 A1 | 6/2012 | Ozcan et al. | |
| 2012/0218379 A1 | 8/2012 | Ozcan et al. | |
| 2012/0248292 A1 | 10/2012 | Ozcan et al. | |
| 2012/0250032 A1 | 10/2012 | Wilde et al. | |
| 2012/0281929 A1 | 11/2012 | Brand et al. | |
| 2013/0057748 A1 | 3/2013 | Duparre et al. | |
| 2013/0083886 A1 | 4/2013 | Carmi et al. | |
| 2013/0093871 A1 | 4/2013 | Nowatzyk et al. | |
| 2013/0094077 A1 | 4/2013 | Brueck et al. | |
| 2013/0100525 A1 | 4/2013 | Chiang et al. | |
| 2013/0170767 A1 | 7/2013 | Choudhury et al. | |
| 2013/0182096 A1 | 7/2013 | Boccara et al. | |
| 2013/0223685 A1 | 8/2013 | Maiden | |
| 2014/0007307 A1* | 1/2014 | Routh, Jr. | G01Q 10/04 |
| | | | 850/3 |
| 2014/0029824 A1 | 1/2014 | Shi et al. | |
| 2014/0043616 A1 | 2/2014 | Maiden et al. | |
| 2014/0050382 A1 | 2/2014 | Adie et al. | |
| 2014/0118529 A1 | 5/2014 | Zheng et al. | |
| 2014/0126691 A1 | 5/2014 | Zheng et al. | |
| 2014/0133702 A1 | 5/2014 | Zheng et al. | |
| 2014/0152801 A1 | 6/2014 | Fine et al. | |
| 2014/0153692 A1 | 6/2014 | Larkin et al. | |
| 2014/0160236 A1 | 6/2014 | Ozcan et al. | |
| 2014/0160488 A1 | 6/2014 | Zhou | |
| 2014/0217268 A1 | 8/2014 | Schleipen et al. | |
| 2014/0267674 A1 | 9/2014 | Mertz et al. | |
| 2014/0347672 A1 | 11/2014 | Pavillon et al. | |
| 2014/0368812 A1 | 12/2014 | Humphry et al. | |
| 2015/0036038 A1* | 2/2015 | Horstmeyer | G01N 23/205 |
| | | | 348/342 |
| 2015/0054979 A1 | 2/2015 | Ou et al. | |
| 2015/0160450 A1 | 6/2015 | Ou et al. | |
| 2015/0264250 A1 | 9/2015 | Ou et al. | |
| 2015/0331228 A1 | 11/2015 | Horstmeyer et al. | |
| 2016/0088205 A1 | 3/2016 | Horstmeyer et al. | |
| 2016/0178883 A1 | 6/2016 | Horstmeyer et al. | |
| 2016/0202460 A1* | 7/2016 | Zheng | H04N 5/2256 |
| | | | 348/79 |
| 2016/0210763 A1 | 7/2016 | Horstmeyer et al. | |
| 2016/0216503 A1 | 7/2016 | Kim et al. | |
| 2016/0266366 A1 | 9/2016 | Chung et al. | |
| 2016/0320595 A1 | 11/2016 | Horstmeyer et al. | |
| 2016/0320605 A1 | 11/2016 | Ou et al. | |
| 2016/0341945 A1 | 11/2016 | Ou et al. | |
| 2017/0178317 A1 | 6/2017 | Besley et al. | |
| 2017/0273551 A1 | 9/2017 | Chung et al. | |
| 2017/0299854 A1 | 10/2017 | Kim et al. | |
| 2017/0354329 A1 | 12/2017 | Chung et al. | |
| 2017/0363853 A1 | 12/2017 | Besley | |
| 2017/0371141 A1 | 12/2017 | Besley | |
| 2018/0088309 A1 | 3/2018 | Ou et al. | |

FOREIGN PATENT DOCUMENTS

| | | |
|---|---|---|
| CN | 101872033 A | 10/2010 |
| CN | 102608597 A | 7/2012 |
| CN | 103201648 A | 7/2013 |
| JP | 2007-299604 A | 11/2007 |
| JP | 2010-012222 A | 1/2010 |
| KR | 10-1998-0075050 A | 11/1998 |
| WO | WO 99/53469 A1 | 10/1999 |
| WO | WO 2002/102128 A1 | 12/2002 |
| WO | WO 2003/062744 A1 | 7/2003 |
| WO | WO 2008/116070 A1 | 9/2008 |
| WO | WO 2011/093043 A1 | 8/2011 |
| WO | WO 2012/037182 A1 | 3/2012 |
| WO | WO 2014/070656 A1 | 5/2014 |
| WO | WO 2015/017730 A1 | 2/2015 |
| WO | WO 2015/027188 A1 | 2/2015 |
| WO | WO 2016/090331 | 6/2016 |
| WO | WO 2016/106379 A1 | 6/2016 |
| WO | WO 2016/118761 A1 | 7/2016 |
| WO | WO 2016/123156 A1 | 8/2016 |
| WO | WO 2016/123157 A1 | 8/2016 |
| WO | WO 2016/149120 A1 | 9/2016 |
| WO | WO 2016/187591 A1 | 11/2016 |
| WO | WO 2017081539 A1 | 5/2017 |
| WO | WO 2017081540 A1 | 5/2017 |
| WO | WO 2017081542 A2 | 5/2017 |

OTHER PUBLICATIONS

U.S. Appl. No. 15/003,559, filed Jan. 21, 2016 entitled "Fourier Ptychographic Tomography".

U.S. Appl. No. 15/068,389, filed Mar. 11, 2016 entitled "Correcting for Aberrations in Incoherent Imaging Systems Using Fourier Ptychographic Techniques".

U.S. Appl. No. 15/081,659, filed Mar. 25, 2016 entitled "Fourier Ptychographic Retinal Imaging Methods and Systems".

U.S. Appl. No. 15/160,941, filed May 20, 2016 entitled "Laser-Based Fourier Ptychographic Imaging Systems and Methods".

U.S. Office Action dated Oct. 5, 2015 in U.S. Appl. No. 14/065,305.

U.S. Notice of Allowance dated Dec. 4, 2015 in U.S. Appl. No. 14/065,305.

U.S. Notice of Allowance dated Jan. 14, 2016 in U.S. Appl. No. 14/448,850.

U.S. Notice of Allowance dated Jan. 22, 2016 in U.S. Appl, No. 14/466,481.

U.S. Notice of Allowance dated Apr. 13, 2016 in U.S. Appl. No. 14/448,850.

(56) References Cited

OTHER PUBLICATIONS

U.S. Notice of Allowance dated Apr. 22, 2016 in U.S. Appl. No. 14/466,481.
U.S. Office Action dated Jul. 14, 2016 in U.S. Appl. No. 15/007,196.
International Search Report and Written Opinion dated Feb. 21, 2014 in PCT/US2013/067068.
International Preliminary Report on Patentability dated May 14, 2015 in PCT/US2013/067068.
European Third-Party Observations, dated Jan. 20, 2016 in EP Application No. 13851670.3.
European Extended Search Report dated Mar. 31, 2016 in EP Application No. 13851670.3.
International Preliminary Report on Patentability dated Mar. 3, 2016 issued in PCT/US2014/052351.
International Search Report and Written Opinion dated Dec. 5, 2014 issued in PCT/US2014/052351.
International Search Report and Written Opinion dated Nov. 13, 2014 issued in PCT/US2014/049297.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
International Search Report and Written Opinion dated May 4, 2016 issued in PCT/US2016/015001.
International Search Report and Written Opinion dated May 11 2016 issued in PCT/US2016/015002.
International Search Report and Written Opinion dated Jun. 27, 2016 issued in PCT/US2016/022116.
International Search Report and Written Opinion dated Jun. 30, 2016 issued in PCT/US2016/014343.
"About Molemap," Retrieved Oct. 23, 2015, 2 pages. [http://molemap.net.au/about-us/].
Abramomwitz, M. et al, "Immersion Media," Olympus Microscopy Resource Center, 2012, 6 pp. [http://www.olympusmicro.com/primer/anatomy/immersion.html].
Abramomwitz, M., et al, "Field Curvature," Olympus Microscopy Resource Center, 2012, 3 pp. [http://www.olympusmicro.com/primer/anatomy/fieldcurvature.html].
"Age-Related Macular Degeneration (AMD) | National Eye Institute." [Online]. Available: https://www.nei.nih.gov/eyedata/amd#top. [Accessed: Apr. 5, 2016].
Alexandrov, S., et al, "Spatial information transmission beyond a system's diffraction limit using optical spectral encoding of the spatial frequency," Journal of Optics A: Pure and Applied Optics 10, 025304 (2008).
Alexandrov, S.A., et al, "Synthetic Aperture Fourier holographic optical microscopy," Phys. Rev. Lett. 97, 168102 (2006).
Arimoto, H., et al, "Integral three-dimensional imaging with digital reconstruction," Opt. Lett. 26, 157-159 (2001).
Balan, R., et al, "On signal reconstruction without phase, Applied and Computational Harmonic Analysis 20," No. 3 (2006): 345-356.
Balan, R., et al, "Painless reconstruction from magnitudes of frame coefficients," J Fourier Anal Appl 15:488-501 (2009).
Bauschke, H.H., et al, "Phase retrieval, error reduction algorithm, and Fienup variants: a view from convex optimization," J Opt Soc Am A 19:1334-1345 (2002).
Becker, S., et al, "Templates for convex cone problems with applications to sparse signal recovery," Technical report, Department of Statistics, Stanford University, (2010), 48 Pages.
Betti, R., et al, "Observational study on the mitotic rate and other prognostic factors in cutaneous primary melanoma arising from naevi and from melanoma de novo," Journal of the European Academy of Dermatology and Venereology, 2014.
Bian, L., et al, "Fourier ptychographic reconstruction using Wirtinger flow optimization," Opt. Express 23:4856-4866 (2015).
Bian, Z., et al, "Adaptive system correction for robust Fourier ptychographic imaging," Optics express, 2013. 21(26): p. 32400-32410.
BioTek® Brochure: BioTek's Multi-Mode Microplate Reading Techonologies, 2016, 2 pp. [http://www.biotek.com].
Bishara, W., et al, "Holographic pixel super-resolution in portable lensless on-chip microscopy using a fiber-optic array," Lab Chip 11(7), 1276-1279 (2011).
Bishara, W., et al, "Lensfree on-chip microscopy over a wide field-of-view using pixel super-resolution," Opt. Express 18(11), 11181-11191 (2010).
Blum, A., et al, "Clear differences in hand-held dermoscopes," JDDG: Journal der Deutschen Dermatologischen Gesellschaft, 2006, 4(12): p. 1054-1057.
Blum, A., et al, Dermatoskopie von Hauttumoren: Auflichtmikroskopie; Dermoskopie; digitale Bildanalyse; mit 28 Tabellen. 2003: Springer DE, Chapter 4 "Dermatoskopisch sichtbare Strukturen" p. 15-66.
Born, M., et al, "Principles of Optics: Electromagnetic theory of propagation, interference and diffraction of light" 7th Ed., Cambridge Univ. Press, (1999) pp. 1-31.
Brady, D., et al, "Multiscale gigapixel photography," Nature 486, 386-389 (2012).
Burer, S., et al, "A nonlinear programming algorithm for solving semidefinite programs via low-rank factorization," Math Program, Ser B 95:329-357 (2003).
Burer, S., et al, "Local minima and convergence in low-rank semidefinite programming. Math Program," Ser A 103:427-444 (2005).
Candes, E.J., et al, "Phase retrieval via matrix completion," SIAM J. Imaging Sci. 6:199-225 (2012).
Candes, E.J., et al, "Phase retrieval via Wirtinger flow: theory and algorithms," IEEE Trans. Info. Theory 61:1985-2007 (2015).
Candes, E.J., et al, "PhaseLift: exact and stable signal recovery from magnitude measurements via convex programming.," Comm Pure Appl Math 66:1241-1274 (2013).
Carroll, J., "Adaptive optics retinal imaging: applications for studying retinal degeneration," Arch. Ophthalmol., vol. 126, pp. 857-858, 2008.
Chao, W. et al, "Soft X-ray microscopy at a spatial resolution better than 15 nm," Nature Letters, vol. 435/30, Jun. 2005 pp. 1210-1213.
Chen, T., et al, "Polarization and phase shifting for 3D scanning of translucent objects," Proc. CVPR, (2007).
Chin, L., et al, "Malignant melanoma: genetics and therapeutics in the genomic era," Genes & development, 2006, 20(16): p. 2149-2182.
Choi, W., et al, "Tomographic phase microscopy," Nature Methods 4(9) (2007), pp. 1-3 Published Online Aug. 12, 2007.
Chung, J., et al, "Counting White Blood Cells from a Blood Smear Using Fourier Ptychographic Microscopy," PLoS One 10(7), e0133489 (2015).
Chung, J., et al, "Wide field-of-view fluorescence image deconvolution with aberration-estimation from Fourier ptychography," Feb. 1, 2016, vol. 7, No. 2, Biomedical Optics Express 352.
Colomb, T., et al, "Automatic procedure for aberration compensation in digital holographic microscopy and applications to specimen shape compensation," Appl. Opt. 45, 851-863 (2006).
De Sa, C., et al, "Global convergence of stochastic gradient descent for some non convex matrix problems," Proc. 32nd Int. Conf. Machine Learning (2015), 10 pp.
Debailleul, M., et al, "High-resolution three-dimensional tomographic diffractive microscopy of transparent inorganic and biological samples," Optic Letters 34 (2008).
Denis, L., et al, "Inline hologram reconstruction with sparsity constraints," Opt. Lett. 34, pp. 3475-3477 (2009).
Di, J., et al, "High resolution digital holographic microscopy with a wide field of view based on a synthetic aperture technique and use of linear CCD scanning," Appl. Opt. 47, pp. 5654-5659 (2008).
Dierolf, M., et al, "Ptychographic coherent diffractive imaging of weakly scattering specimens," New J. Phys. 12, 035017 (2010).
Dierolf, M., et al, "Ptychographic X-ray computed tomography at the nanoscale," Nature, vol. 467, pp. 436-439, (2010).
"Doctor Mole—Skin Cancer App," Retrieved Oct. 23, 2015, 1 page. [http://www.doctormole.com].
Dong, S., et al, "FPscope: a field-portable high-resolution microscope using a cellphone lens," Biomed. Opt. Express 5(10), 3305-3310 (2014).

(56) References Cited

OTHER PUBLICATIONS

Dong, S., et al, "High-resolution fluorescence imaging via pattern-illuminated Fourier ptychography," Opt. Express 22(17), 20856-20870 (2014).

Dong, S., et al, "Aperture-scanning Fourier ptychography for 3D refocusing and super-resolution macroscopic imaging," pp. 13586-13599 (Jun. 2, 2014).

Eldar, Y.C., et al,"Sparse phase retrieval from short-time Fourier measurements," IEEE Signal Processing Letters 22, No. 5 (2015): 638-642.

Emile, O., et al, "Rotating polarization imaging in turbid media," Optics Letters 21(20), (1996).

Faulkner, H.M.L., and Rodenburg, J.M., "Error tolerance of an iterative phase retrieval algorithm for moveable illumination microscopy," Ultramicroscopy 103(2), 153-164 (2005).

Faulkner, H.M.L., and Rodenburg, J.M., "Movable aperture lensless transmission microscopy: a novel phase retrieval algorithm," Phys. Rev. Lett. 93, 023903 (2004).

Fazel, M.,"Matrix rank minimization with applications," PhD Thesis (Stanford University, Palo Alto, CA). (2002).

Feng, P., et al, "Long-working-distance synthetic aperture Fresnel off-axis digital holography," Optics Express 17, pp. 5473-5480 (2009).

Fienup, J. R., "Invariant error metrics for image reconstruction," Appl. Opt. 36(32), 8352-8357 (1997).

Fienup, J. R., "Lensless coherent imaging by phase retrieval with an illumination pattern constraint," Opt. Express 14, 498-508 (2006).

Fienup, J. R., "Phase retrieval algorithms: a comparison," Appl. Opt. 21, 2758-2769 (1982).

Fienup, J. R., "Reconstruction of a complex-valued object from the modulus of its Fourier transform using a support constraint," J. Opt. Soc. Am. A 4, 118-123 (1987).

Fienup, J. R., "Reconstruction of an object from the modulus of its Fourier transform," Opt. Lett. 3, 27-29 (1978).

Gan, X., et al, "Image enhancement through turbid media under a microscope by use of polarization gating methods," JOSA A 16(9), (1999).

Gerke T.D., et al, "Aperiodic volume optics," Nature Photonics (2010), vol. 4, pp. 188-193.

Ghosh, A., et al, "Multiview face capture using polarized spherical gradient illumination," ACM Transactions on Graphics 30(6) (2011).

Godara, P., et al, "Adaptive optics retinal imaging: emerging clinical applications.," Optom. Vis. Sci., vol. 87, No. 12, pp. 930-941, Dec. 2010.

Goodman, J.W., "Introduction to Fourier Optics," Roberts & Company Publication, Third Edition, chapters 1-6, pp. 1-172 (2005).

Goodson, A.G., et al, "Comparative analysis of total body and dermatoscopic photographic monitoring of nevi in similar patient populations at risk for cutaneous melanoma," Dermatologic Surgery, 2010. 36(7): p. 1087-1098.

Granero, L., et al, "Synthetic aperture superresolved microscopy in digital lensless Fourier holography by time and angular multiplexing of the object information," Appl. Opt. 49, pp. 845-857 (2010).

Grant, M., et al, "CVX: Matlab software for disciplined convex programming," version 2.0 beta. http://cvxr.com/cvx, (Sep. 2013), 3 pages.

Greenbaum, A., et al, "Field-portable wide-field microscopy of dense samples using multi-height pixel super resolution based lensfree imaging," Lab Chip 12(7), 1242-1245 (2012).

Greenbaum, A., et al, "Increased space—bandwidth product in pixel super-resolved lensfree on-chip microscopy," Sci. Rep. 3, p. 1717 (2013).

Gruev, V., et al, "Dual-tier thin film polymer polarization imaging sensor," Optics Express, vol. 18, No. 18, 12 pages (2010).

Guizar-Sicairos, M., and Fienup, J.R.,"Phase retrieval with transverse translation diversity: a nonlinear optimization approach," Opt. Express 16, 7264-7278 (2008).

Gunturk, B.K., et al, "Image Restoration: Fundamentals and Advances," vol. 7, Chapter 3, pp. 63-68 (CRC Press, 2012).

Gustafsson, M.G.L., "Surpassing the lateral resolution limit by a factor of two using structured illumination microscopy," J. Microsc. 198, 82-87 (2000).

Gutzler, T., et al, "Coherent aperture-synthesis, wide-field, high-resolution holographic : microscopy of biological tissue," Opt. Lett. 35, pp. 1136-1138 (2010).

Haigh, S. J., et al, (2009) "Atomic structure imaging beyond conventional resolution limits in the transmission electron microscope"; Physical Review Letters 103. 126101-1 126101-4.

Han, C., et al, "Wide Field-of-View On-Chip Talbot Fluorescence Microscopy for Longitudinal Cell Culture Monitoring from within the Incubator" Anal. Chem. 85(4), 2356-2360 (2013).

Hillman, T.R., et al, "High-resolution, wide-field object reconstruction with synthetic aperture Fourier holographic optical microscopy," Opt. Express 17, pp. 7873-7892 (2009).

Hofer, H., et al, "Dynamics of the eye's wave aberration," J. Opt. Soc. Am. A, vol. 18, No. 3, p. 497, 2001.

Hofer, H., et al, "Organization of the human trichromatic cone mosaic.," J. Neurosci., vol. 25, No. 42, pp. 9669-9679, Oct. 2005.

Hong, S-H., et al, "Three-dimensional volumetric object reconstruction using computational integral imaging," Opt. Express 12, 483-491 (2004).

Hoppe, W., "Diffraction in inhomogeneous primary wave fields. 1. Principle of phase determination from electron diffraction interference," Acta Crystallogr. A25, 495-501 1969.

Horstmeyer, R., et al, "A phase space model of Fourier ptychographic microscopy," Optics Express, 2014. 22(1): p. 338-358.

Horstmeyer, R., et al, "Digital pathology with fourier ptychography," Comput. Med. Imaging Graphics 42, 38-43 (2015).

Horstmeyer, R., et al, "Overlapped fourier coding for optical aberration removal," Manuscript in preparation, 19 pages (2014).

Horstmeyer, R., et al, "Solving ptychography with a convex relaxation," Physics Optics (2014) 1-8 pages.

Hüe F. et al "Wave-front phase retrieval in transmission electron microscopy via ptychography," Phys. Rev. B 82, 121415 (2010).

Humphry, M., et al, "Ptychographic electron microscopy using high-angle dark-field scattering for sub-nanometre resolution imaging," Nat. Commun. 3, 730 (2012).

IncuCyte® ZOOM System, Brochure, 1-4 pp. (2016) (retrieved Feb. 25, 2016), [http://www.essenbioscience.com/media/uploads/files/8000-0333-E00-IncuCyte_ZOOM_brochure.pdf].

Jaganathan, K., et al, "Recovery of sparse 1-D signals from the magnitudes of their Fourier transform," IEEE International Symposium on Information Theory Proceedings (2012): 1473-1477.

Jaganathan, K., et al, "Phase retrieval with masks using convex optimization," IEEE International Symposium on Information Theory Proceedings (2015): 1655-1659.

Jaganathan, K., et al, "STFT Phase retrieval: uniqueness guarantees and recovery algorithms," arXiv preprint arXiv:1508.02820 (2015).

Joeres, S., et al, "Retinal imaging with adaptive optics scanning laser ophthalmoscopy in unexplained central ring scotoma.," Arch. Ophthalmol., vol. 126, No. 4, pp. 543-547, Apr. 2008.

Jung, J.H., et al, "Microfluidic-integrated laser-controlled microactuators with on-chip microscopy imaging functionality," Lab Chip 14 (19), Oct. 7, 2014, pp. 3781-3789.

Kay, D. B., et al, "Outer retinal structure in best vitelliform macular dystrophy.," JAMA Ophthalmol., vol. 131, pp. 1207-1215, 2013.

Kim, J., et al, Incubator embedded cell culture imaging system (EmSight) based on Fourier ptychographic microscopy. EmSight manuscript, Optical Society of America, 2015.

Kim, M., et al, "High-speed synthetic aperture microscopy for live cell imaging," Opt. Lett. 36, pp. 148-150 (2011).

Kirkland, A.I., et al, "Multiple beam tilt microscopy for super resolved imaging;" Japanese Society of Electron Microscopy: Journal of Electron Microscopy I: 11-22(1997), vol. 46, No. 1 1997.

Kirkland, A.I., et al, "Super-resolution by aperture synthesis: tilt series reconstruction in CTEM," Ultramicroscopy 57, (1995)355-374, Received May 27, 1994, in final form Oct. 2, 1994; 1995 Elsevier Science B.V. SSDI 0304-3991(94)00191-x.

Kittler, H., et al, "Morphologic changes of pigmented skin lesions: a useful extension of the ABCD rule for dermatoscopy," Journal of the American Academy of Dermatology, 1999. 40(4): p. 558-562.

(56) References Cited

OTHER PUBLICATIONS

Kozak, I., "Retinal imaging using adaptive optics technology.," Saudi J. Ophthalmol. Off. J. Saudi Ophthalmol. Soc., vol. 28, No. 2, pp. 117-122, Apr. 2014.
Lauer, V., "New Approach to optical diffraction tomography yielding a vector equation of diffraction tomography and a novel tomography microscope," Journal of Microscopy, vol. 205, Pt 2 Feb. 2002, pp. 165-176, The Royal Microscopical Society 2001.
Lee, K., et al, "Synthetic Fourier transform light scattering," Optics Express 21 (2013).
Levoy, M., et al, "Light field microscopy," ACM Trans. Graphics 25, (2006).
Levoy, M., et al, "Recording and controlling the 4D light field in a microscope using microlens arrays," J. Microsc. 235 (2009).
Li, X., et al, "Sparse signal recovery from quadratic measurements via convex programming," SIAM Journal on Mathematical Analysis 45, No. 5 (2013): 3019-3033.
Lohmann, A. W., et al, "Space-bandwidth product of optical signals and systems," J. Opt. Soc. Am. A 13, pp. 470-473 (1996).
Lue, N., et al, "Live Cell Refractometry Using Hilbert Phase Microscopy and Confocal Reflectance Microscopy," The Journal of Physical Chemistry A, 113, pp. 13327-13330 (2009).
Luxexcel® Brochure, Luxexcel: 3D Printing Service Description, Retrieved Mar. 7, 2016, 5 pp. [http://www.luxexcel.com].
"Lytro," Retrieved Oct. 23, 2015, 6 pp. [https://www.lytro.com/].
Ma, W., et al, "Rapid Acquisition of Specular and Diffuse Normal Maps from Polarized Spherical Gradient Illumination," University of Southern California, Institute for Creative Technologies, 12 pages (2007).
Mahajan, V. N., "Zernike circle polynomials and optical aberrations of systems with circular pupils," Appl. Opt. 33(34), 8121-8124 (1994).
Maiden, A. M., et al, "A new method of high resolution, quantitative phase scanning microscopy," in: M.T. Postek, D.E. Newbury, S.F. Platek, D.C. Joy (Eds.), SPIE Proceedings of Scanning Microscopy, 7729, 2010.
Maiden, A. M.,"An improved ptychographical phase retrieval algorithm for diffractive imaging," Ultramicroscopy 109(10), 1256-1262 (2009).
Maiden, A. M., et al, "Superresolution imaging via ptychography," Journal of the Optical Society of America A. Apr. 2011, vol. 28 No. 4, pp. 604-612.
Maiden, A. M., et al, "Optical ptychography: a practical implementation with useful resolution," Opt. Lett. 35, 2585-2587 (2010).
Marchesini S., "A unified evaluation of iterative projection algorithms for phase retrieval," Rev Sci Instrum 78:011301 (2007).
Marchesini S., et al, "Augmented projections for ptychographic imaging," Inverse Probl 29:115009 (2013).
Marrison, J., et al, "Ptychography-a label free, high-contrast imaging technique for live cells using quantitative phase information," Sci. Rep. 3, 2369 (2013).
Medoff, B.P., et al, "Iterative convolution backprojection algorithms for image reconstruction from limited data," J. Opt. Soc. Am. vol. 73, No. 11, Nov. 1983, pp. 1493-1500.
"Melafind," Retrieved Oct. 23, 2015, 4 pages. [http://www.melafind.com/].
Meyer, R.R., et al, "A method for the determination of the wave aberration function of high-resolution TEM," Ultramicroscopy 99 (2004) 115-123: Elsevier B.V. Doi: 10.1016/j.ultramic.2003.11.001.
Miao, J., et al, "High Resolution 3D X-Ray Diffraction Microscopy," Physical Review Letters, Aug. 19, 2002, vol. 89, No. 8, pp. 1-4.
Mico, V., et al, "Synthetic aperture microscopy using off-axis illumination and polarization coding," Optics Communications, pp. 276, 209-217 (2007).
Mico, V., et al, "Synthetic aperture superresolution with multiple off-axis holograms," JOSA A 23, pp. 3162-3170 (2006).
Mir, M. et al, "Optical measurement of cycle-dependent cell growth," Proceedings of the National Academy of Sciences 108, pp. 13124-13129 (2011).
Mir, M., et al, "Blood screening using diffraction phase cytometry," Journal of Biomedical Optics 15, pp. 027016-027014 (2010).
Moreno, I., "Creating a desired lighting pattern with an LED array," 8th International Conference on Solid State Lighting, Proceedings of SPIE, vol. 7058, 2008, 9 pp.
Mrejen, S., et al, "Adaptive optics imaging of cone mosaic abnormalities in acute macular neuroretinopathy.," Ophthalmic Surg. Lasers Imaging Retina, vol. 45, No. 6, pp. 562-569, Jan. 2014.
Nayar, S. K., et al, "Fast separation of direct and global components of a scene using high frequency illumination," ACM Transactions on Graphics 25(3) (2006).
Ng, R., et al, "Light field photography with a hand-held plenoptic camera", Computer Science Technical Report CSTR, 2005. 2(11).
Nomura, H., and Sato, T., "Techniques for measuring aberrations in lenses used in photolithography with printed patterns," Appl. Opt. 38(13), 2800-2807 (1999).
Ohlsson, H., et al, "Compressive phase retrieval from squared output measurements via semidefinite programming," arXiv:1111.6323 (2011).
Ou, X., et al, "High numerical aperture Fourier ptychography: principle, implementation and characterization," Opt. Express 23:3472-3491 (2015).
Ou, X., et al, "Quantitative phase imaging via Fourier ptychographic microscopy," Optics Letters, 2013. 38(22): p. 4845-4848.
Ou. X., et al, "Embedded pupil function recovery for Fourier ptychographic microscopy," Optics Express 22 (5), pp. 4960-4972 (2014), with Erratum (2015).
Ou. X., et al, "Embedded pupil function recovery for Fourier ptychographic microscopy," submitted Dec. 26, 2013; 13 pp.
Pacheco, S., et al, "Reflective Fourier Ptychography," J. Biomed. Opt. 21(2), pp. 026010-1-026010-7, (Feb 18, 2016). [http://biomedicaloptics.spiedigitallibrary.org].
Recht, B., et al, "Guaranteed minimum-rank solutions of linear matrix equations via nuclear norm minimization," SIAM Review 52, No. 3 (2010): 471-501.
Reinhard, E., et al, "High Dynamic Range Imaging: Acquisition, Display, and Image-based Lighting" (Morgan Kaufmann, 2010).
Rodenburg, J. M., et al, "A phase retrieval algorithm for shifting illumination," Appl. Phys. Lett 85, 4795-4797 (2004).
Rodenburg, J. M., et al, "Hard-X-ray lensless imaging of extended objects," Phys. Rev. Lett. 98, 034801 (2007).
Rodenburg, J. M., et al, "The theory of super-resolution electron microscopy via Wigner-distribution deconvolution," Phil. Trans. R. Soc. Lond. A 339, 521-553 (1992).
Rodenburg, J., "Ptychography and related diffractive imaging methods," Adv. Imaging Electron Phys.150, 87-184 (2008).
Rossi, E.A., et al, "In vivo imaging of retinal pigment epithelium cells in age related macular degeneration.," Biomed. Opt. Express, vol. 4, No. 11, pp. 2527-2539, Jan. 2013.
Rowe, M., et al, "Polarization-difference imaging: a biologically inspired technique for observation through scattering media," Optics Letters, vol. 20, No. 6, 3 pages (1995).
Schechner, Y., "Multiplexing for Optimal Lighting," IEEE Transactions on Pattern Analysis and Machine Intelligence, vol. 29, No. 8, 1339-1354 (2007).
Schnars, U., et al, "Digital recording and numerical reconstruction of holograms," Measurement Science and Technology, 13, R85 (2002).
Schwarz, C., et al, "Imaging interferometric microscopy," Optics letters 28, pp. 1424-1426 (2003).
Shechner, Y., et al, "Polarization-based vision through haze," Applied Optics 42(3), (2003).
Shechtman, Y., et al, "Sparsity based sub-wavelength imaging with partially incoherent light via quadratic compressed sensing," Opt Express 19:14807-14822 (2011).
Siegel, R., et al, "Cancer statistics 2013," CA: a cancer journal for clinicians, 2013. 63(1): p. 11-30.
Stoecker, W., et al, "Diagnostic Inaccuracy of Smartphone Applications for Melanoma Detection: Representative Lesion Sets and the Role for Adjunctive Technologies," JAMA Dermatology, 2013. 149(7): p. 884.
Sun, D., et al, "Estimating a signal from a magnitude spectrogram via convex optimization," arXiv:1209.2076 (2012).

(56) References Cited

OTHER PUBLICATIONS

Sun J., et al, "Coded multi-angular illumination for Fourier ptychography based on Hadamard codes," 5 pages (2015).
Tam, K., et al, "Tomographical imaging with limited-angle input," J. Opt. Soc. Am. 21 (1981).
Thibault, P. et al, "Probe retrieval in ptychographic coherent diffractive imaging," Ultramicroscopy 109(4), 338-343 (2009).
Thibault P., et al, "High-resolution scanning X-ray diffraction microscopy," Science 321, 2008, pp. 379-382.
Thomas, L., et al, "Semiological value of ABCDE criteria in the diagnosis of cutaneous pigmented tumors," Dermatology, 1998. 197(1): p. 11-17.
Tian, L., et al, "Multiplexed Coded Illumination for Fourier Ptychography with an LED Array Microscope," Optical Society of America, 14 pages (2014).
Tippie, A.E., et al, "High-resolution synthetic-aperture digital holography with digital phase and pupil correction," Opt. Express 19, pp. 12027-12038 (2011).
Turpin, T., et al, "Theory of the synthetic aperture microscope," pp. 230-240 (1995).
Tyson, R., "Principles of Adaptive Optics" (CRC Press, 2010).
Vulovic, M., et al, "When to use the projection assumption and the weak-phase object approximation in phase contrast cryo-EM," Ultramicroscopy 136 (2014) 61-66.
Waldspurger, I., et al, "Phase recovery, maxcut and complex semidefinite programming," Mathematical Programming 149, No. 1-2 (2015): 47-81.
Wang, Q., et al, "Adaptive Optics Microperimetry and OCT Images Show Preserved Function and Recovery of Cone Visibility in Macular Telangiectasia Type 2 Retinal Lesions," Invest. Ophthalmol. Vis. Sci., vol. 56, pp. 778-786 (2015).
Wang, Z., et al, "Tissue refractive index as marker of disease," Journal of Biomedical Optics 16, 116017-116017 (2011).
Watanabe, M., et al, "Telecentric optics for focus analysis," IEEE trans. pattern. anal. mach. intell., 19 1360-1365 (1997).
Wesner, J., et al, "Reconstructing the pupil function of microscope objectives from the intensity PSF," in Current Developments in Lens Design and Optical Engineering III, R. E. Fischer, W. J. Smith, and R. B. Johnson, eds., Proc. SPIE 4767, 32-43 (2002).
Williams, A., et al, "Fourier ptychographic microscopy for filtration-based circulating tumor cell enumeration and analysis," J. Biomed. Opt. 19(6), 066007 (2014).
Wolf, J., et al, "Diagnostic Inaccuracy of Smartphone Applications for Melanoma Detection," JAMA Dermatology, 2013, 149(7): p. 885-885.
Wu, J., et al, "Focal plane tuning in wide-field-of-view microscope with Talbot pattern illumination," Opt. Lett. 36, 2179-2181 (2011).
Wu, J., et al, "Wide field-of-view microscope based on holographic focus grid illumination," Opt. Lett. 35, 2188-2190 (2010).
Xu, W., et al, "Digital in-line holography for biological applications," Proc. Natl Acad. Sci. USA 98, pp. 11301-11305 (2001).
Yuan, C., et al, "Angular multiplexing in pulsed digital holography for aperture synthesis," Optics Letters 33, pp. 2356-2358 (2008).
Zeiss, C., "Microscopy, Cells Need the Perfect Climate, System Solutions for Live Cell Imaging under Physiological Conditions," printed Feb. 2008, 1-42 pgs.
Zhang, Y., et al, "Self-learning based fourier ptychographic microscopy," Optics Express, 16pgs (2015).
Zhang, Y., et al, "Photoreceptor Perturbation Around Subretinal Drusenoid Deposits as Revealed by Adaptive Optics Scanning Laser Ophthalmoscopy," Am. J. Ophthalmol., vol. 158, No. 3, pp. 584-596, 2014.
Zheng, G., et al, "Characterization of spatially varying aberrations for wide field-of-view microscopy," Opt. Express 21, 15131-15143 (2013).
Zheng, G., et al, "Microscopy refocusing and dark-field imaging by using a simple LED array," Opt. Lett. 36, 3987-3989 (2011).
Zheng, G., et al, "0.5 gigapixel microscopy using a flatbed scanner," Biomed. Opt. Express 5, 1-8 (2014).
Zheng, G., et al, "Sub-pixel resolving optofluidic microscope for on-chip cell imaging," Lab Chip 10, pp. 3125-3129 (2010).
Zheng, G. "The ePetri dish, an on-chip cell imaging platform based on subpixel perspective sweeping microscopy (SPSM)," Proc. Natl. Acad. Sci. USA 108, pp. 16889-16894 (2011).
Zheng, G., et al, "Wide-field, high-resolution Fourier ptychographic microscopy," Nature Photonics, vol. 7, pp. 739-745, Published Online Jul. 28, 2013 at www.nature.com/naturephotonics.
Chung, J., et al, "Wide-field Fourier ptychographic microscopy using laser illumination source," Optical Society of America, 13 pgs., Mar. 23, 2016.
Guo, K., et al, "Optimization of sampling pattern and the design of Fourier ptychographic illuminator," Optical Society of America; Optics Express, vol. 23, No. 5, pp. 6171-6180 (2015).
Phillips, Z., et al, "Multi-Contrast Imaging and Digital Refocusing on a Mobile Microscope with a Domed LED Array," PLoS One, 10 (5), pp. 1-13 (2015).
Horstmeyer, R., et al, "Standardizing the resolution claims for coherent microscopy," Nature Photonics, vol. 10, pp. 68-71, Feb. 2016.
Horstmeyer, R., et al, "Solving ptychography with a convex relaxation," New Journal of Physics, vol. 17 (2015) 1-14 pages.
U.S. Notice of Allowance dated Aug. 23, 2016 in U.S. Appl. No. 14/466,481.
U.S. Office Action dated Aug. 16, 2016 in U.S. Appl. No. 14/065,280.
U.S. Office Action dated Sep. 16, 2016 I U.S. Appl. No. 14/065,305.
U.S. Notice of Allowance dated Nov. 2, 2016 in U.S. Appl. No. 14,572,493.
U.S. Office Action dated Nov. 22, 2016 in U.S. Appl. No. 15/003,559.
U.S. Supplemental Notice of Allowance dated Dec. 12, 2016 in U.S. Appl. No. 14/572,493.
U.S. Notice of Allowance dated Jan. 13, 2017 in U.S. Appl. No. 14/065,305.
U.S. Final Office Action dated Jan. 23, 2017 in U.S. Appl. No. 15/007,196.
U.S. Office Action dated Feb. 21, 2017 in U.S. Appl. No. 14/960,252.
U.S. Supplemental Notice of Allowability dated Mar. 2, 2017 in U.S. Appl. No. 14/065,305.
U.S. Notice of Allowance dated Mar. 8, 2017 in U.S. Appl. No. 14/572,493.
U.S. Office Action dated Mar. 13, 2017 in U.S. Appl. No. 14/658,019.
U.S. Notice of Allowance dated Mar. 22, 2017 in U.S. Appl. No. 15/007,196.
U.S. Office Action dated Mar. 24, 2017 in U.S. Appl. No. 14/710,947.
U.S. Notice of Allowance dated Mar. 31, 2017 in U.S. Appl. No. 14/572,493.
U.S. Final Office Action dated Apr. 3, 2017 in U.S. Appl. No. 14/065,280.
International Search Report and Wrtitten Opinion dated Sep. 5, 2016 issued in PCT/US2016/033638.
Chinese Office Action [Description in English] dated Jul. 11, 2016 issued in Application No. CN 201380068831.6.
Chinese Office Action [Description in English] dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Applicatoin No. 14832857.8.
Chinese Second Office Action [Description in English] dated Feb. 17, 2017 issued in Application No. CN201380068831.6.
Kim, M., et al, "High-speed synthetic aperture microscopy for live cell imaging," Optics Letters, vol. 36, No. 2, Jan. 15, 2011, pp. 148-150. <doi:10.1364/OL.36.000148>.
Lu, H., et al, "Quantitative phase imaging and complex field reconstruction by pupil modulation differential phase contrast," Optics Express, vol. 24, No. 22, Oct. 31, 2016, pp. 25345-25361. <doi:10.1364/OE.24.025345>.
Ou, X., et al, "Aperture scanning Fourier ptychographic microscopy," Biomedical Optics Express, vol. 7, No. 8, Aug. 1, 2016, pp. 3140-3150. <doi:10.1364/BOE.7.003140>.
Horstmeyer, R., et al, "Diffraction tomography with Fourier ptychography," Optica, vol. 3, No. 8, Aug. 2016, pp. 827-835. <doi:10.1364/OPTICA.3.000827>.

(56) References Cited

OTHER PUBLICATIONS

Bian, L., et al, "Fourier ptychographic reconstruction using Poisson maximum likelihood and truncated Wirtinger gradient," NPG: Scientific Reports 6, article No. 27384, Jun. 10, 2016, pp. 1-10. <doi:10.1038/srep27384> [URL: http://www.nature.com/scientificreports/].
Wu, J., et al, "Harmonically matched grating-based full-field quantitative high-resolution phase microscope for observing dynamics of transparent biological samples," OSA Publ., Optics Express, vol. 15, No. 26, Dec. 24, 2007, pp. 18141-18155. <doi:10.1364/OE.15.018141>.
Wu, J., et al, "Paired-angle-rotation scanning optical coherence tomography forward-imaging probe," OSA Publ., Optics Letters, vol. 31, No. 9, May 1, 2006, pp. 1265-1267. <doi: 10.1364/OL.31.001265>.
Kawata, S. et al, "Optical microscope tomography. I. Support constraint," Journal Optical Society America A, vol. 4, No. 1, Jan. 1987, pp. 292-297. <doi:10.1364/JOSAA.4.000292>.
Chai, A., et al, "Array imaging using intensity-only measurements," IOP Publishing Inverse Problems, vol. 27, No. 1, Jan. 2011, pp. 1-16. <doi:10.1088/0266-5611/27/1/015005> [Retrieved on Mar. 24, 2017] [URL: http://www.stacks.iop.org/IP/27/015005].
Preliminary Amendment dated Mar. 17, 2014 filed in U.S. Appl. No. 14/065,280.
Preliminary Amendment dated Apr. 25, 2016 filed in U.S. Appl. No. 14/710,947.
Preliminary Amendment dated Nov. 28, 2016 filed in U.S. Appl. No. 15/206,859.
Preliminary Amendment dated Mar. 17, 2014 filed in U.S. Appl. No. 14/065,305.
Preliminary Amendment dated Nov. 28, 2016 filed in U.S. Appl. No. 15/209,604.
U.S. Notice of Allowance dated Jun. 9, 2017 in U.S. Appl. No. 14/065,305.
U.S. Notice of Allowance dated Jun. 9, 2017 in U.S. Appl. No. 15/206,859.
U.S. Notice of Allowance dated Jun. 9, 2017 in U.S. Appl. No. 15/007,196.
U.S. Notice of Allowance dated Jun. 20, 2017 in U.S. Appl. No. 14/572,493.
U.S. Supplemental Notice of Allowance dated Jun. 28, 2017 in U.S. Appl. No. 15/206,859.
U.S. Final Office Action dated Jul. 27, 2017 in U.S. Appl. No. 15/003,559.
U.S. Notice of Allowance dated Aug. 16, 2017 in U.S. Appl. No. 15/209,604.
Office Action dated Aug. 31, 2017 in U.S. Appl. No. 15/636,494.
U.S. Notice of Allowance dated Sep. 1, 2017 in U.S. Appl. No. 15/206,859.
Office Action dated May 19, 2017 in U.S. Appl. No. 15/081,659.
Notice of Allowance dated Sep. 20, 2017 in U.S. Appl. No. 15/007,196.
Notice of Allowance dated Oct. 11, 2017 in U.S. Appl. No. 14/572,493.
Notice of Allowance dated Oct. 20, 2017 in U.S. Appl. No. 15/081,659.
Office Action dated Nov. 3, 2017 in U.S. Appl. No. 15/068,389.
Notice of Allowance dated Dec. 4, 2017 in U.S. Appl. No. 14/065,305.
Final Office Action dated Dec. 14, 2017 in U.S. Appl. No. 14/960,252.
Final Office Action dated Dec. 28, 2017 in U.S. Appl. No. 14/710,947.
Final Office Action dated Jan. 17, 2018 in U.S. Appl. No. 14/658,019.
Notice of Allowance dated Jan. 23, 2018 in U.S. Appl. No. 15/206,859.
Office Action dated Jan. 25, 2018 in U.S. Appl. No. 14/065,280.
Notice of Allowance dated Jan. 26, 2018 in U.S. Appl. No. 15/209,604.
Notice of Allowance dated Feb. 9, 2018 in U.S. Appl. No. 15/081,659.
Office Action dated Apr. 4, 2018 issued in U.S. Appl. No. 15/003,559.
Office Action dated Apr. 13, 2018 issued in U.S. Appl. No. 15/160,941.
Chinese Office Action [Description in English] dated May 31, 2016 issued in Application No. CN 201380068831.6.
Chinese Second Office Action [Description in English] dated Jan. 22, 2017 issued in Application No. CN201380068831.6.
International Preliminary Report on Patentability dated Jun. 15, 2017 issued in Application No. PCT/US2015/064126.
European Office Action dated May 16, 2017 issued in European Patent Application No. 13851670.3.
International Preliminary Report on Patentability dated Jul. 6, 2017 issued in Application No. PCT/US2015/067498.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
International Preliminary Report on Patentability dated Aug. 10, 2017 issued in Application No. PCT/US2016/015002.
Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.
Japanese Office Action dated Oct. 17, 2017 issued in Application No. 2015539884.
Chinese Office Action [Summary in English] dated Oct. 26, 2017 issued in CN 201480057911.6.
International Preliminary Report on Patentability dated Nov. 30, 2017 issued in PCT/US2016/033638.
Australian Examination Report 1/Office Action dated Jan. 18, 2018 issued in AU 2014308673.
Chinese First Office Action dated Feb. 24, 2018 issued in CN 201680003937.1.
Abrahamsson, S., et al., "Fast multicolor 3D imaging using aberration-corrected mulitfocus microscopy," Brief Communications: Nature Methods, vol. 10, No. 1, Jan. 2013, pp. 60-65. <doi:10.1038/nmeth.2277>.
Bunk, O., et al, "Influence of the overlap parameter on the convergence of the ptychographical iterative engine," Ultramicroscopy, vol. 108, (2008), pp. 481-487. <doi: 10.1016/j.ultramic.2007.08.003>.
Holloway, J., et al. "SAVI: Synthetic apertures for long-range, subdiffraction-limited visible imaging using Fourier ptychography," Science Advances | Research Article, vol. 3, No. 4, Apr. 14, 2017, pp. 1-11. <doi:10.1126/sciadv.1602564> [retrieved on Nov. 28, 2017] <URL:http://advances.sciencemag.org/>.
Hoppe, W., "Diffraction in inhomogeneous primary wave fields. 1. Principle of phase determination from electron diffraction interference." Acta Crystallographica Section a-Crystal Physics Diffraction Theoretical and General Crystallography, A25, Jan. 1, 1969, pp. 495-501. (English Machine Translation Incl.).
Kner, P., "Phase diversity for three-dimensional imaging," Journal of the Optical Society of America A, vol. 30, No. 10, Oct. 1, 2013, pp. 1980-1987. <doi:10.1364/JOSAA.30.001980>.
Reinhard, E., et al, "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.
Sankaranarayanan, Aswin C., et al, "CS-MUVI: Video Compressive Sensing for Spatial-Multiplexing Cameras," Proceedings of the IEEE International Conference Computational Photography (ICCP), Apr. 2012, pp. 11. <doi:10.1109/ICCPhot.2012.6215212>.
Tian, L., et al, "3D differential phase-contrast microscopy with computational illumination using an LED array," Optics Letters, vol. 39, No. 5, Mar. 1, 2014, pp. 1326-1329. <doi:10.1364/OL39.001326>.
Tian, L., et al, "Computational illumination for high-speed in vitro Fourier ptychographic microscopy," Optica: Research Article, vol. 2, No. 10, Oct. 14, 2015, pp. 904-911. <doi:10.1364/OPTICA.2.000904>.
Wills, S., "Synthetic Apertures for the Optical Domain," Optics & Photonics News Article [webpage], The Optical Society (OSA), Apr. 18, 2017, pp. 2. <URL:https://www.osa-opn.org/home/newsroom/2017/april/synthetic_apertures_for_the_optical_domain/>.

(56) References Cited

OTHER PUBLICATIONS

Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Zheng, G., "Fourier Ptychographic Imaging: A MATLAB tutorial," IOP Concise Physics, Morgan & Claypool Publication, San Rafael, CA., May 2016, pp. 96. <ISBN: 978-1-6817-4272-4 (ebook)> <doi: 10.1088/978-1-6817-4273-1>.
Zheng, G., et al, "Wide-field, high-resolution Fourier ptychographic microscopy," Nature Photonics, vol. 7, Sep. 2013, Published Online Jul. 28, 2013, pp. 739-746. <doi:10.1038/NPHOTON.2013.187>.
U.S. Notice of Allowance dated Jun. 27, 2018 in U.S. Appl. No. 15/636,494.
Office Action Interview Summary dated May 3, 2018 in U.S. Appl. No. 15/068,389.
Final Office Action dated Jun. 6, 2018 issued in U.S. Appl. No. 15/068,389.
European Extended Search Report dated Jun. 6, 2018 issued in Application No. 15865492.1.
Extended European Search Report dated Jul. 3, 2018 issued in Application No. EP 15874344.3.
Jacques, et al., "Imaging Superficial Tissues With Polarized Light," Lasers in Surgery and Medicine, vol. 26, No. 2, Apr. 25, 2000, pp. 119-129.
Jenson, et al. "Types of imaging, Part 2: An Overview of Fluorescence Microscopy." The Anatomical Record, vol. 295, No. 10, Oct. 1, 2012, pp. 1621-1627.
Sarder, et al. "Deconvolution Methods for 3-D Fluorescence Microscopy Images," IEEE Signal Processing Magazine, vol. 23, No. 3, May 2006, pp. 32-45.
U.S. Appl. No. 15/963,966, filed Apr. 26, 2018, Ou et al.
U.S. Appl. No. 15/959,050, filed Apr. 20, 2018, Horstmeyer et al.
European Extended Search Report dated Aug. 14, 2018 issued in EP 16744003.1.
U.S. Notice of Allowance dated Oct. 5, 2018 in U.S. Appl. No. 15/636,494.
U.S. Office Action dated Sep. 7, 2018 in U.S. Appl. No. 14/979,154.
Extended European Search Report dated Sep. 12, 2018 issued in Application No. EP 16740769.1.
Notice of Allowance dated Sep. 17, 2018 in U.S. Appl. No. 15/820,295.
U.S. Office Action dated Oct. 4, 2018 in U.S. Appl. No. 14/658,019.
Preliminary Amendment dated Jun. 13, 2018 filed in U.S. Appl. No. 15/820,295.
U.S. Notice of Allowance dated Jul. 25, 2018 in U.S. Appl. No. 14/710,947.
Japanese First Office Action dated Jul. 31, 2018 issued in Application No. JP 2016-531919.
Chinese Second Office Action dated Jul. 3, 2018 issued in Application No. CN 201480054301.0.
Chinese Third Office Action dated Jul. 13, 2018 issued in CN 201480057911.6.
Preliminary Amendment filed Jul. 11, 2018 in U.S. Appl. No. 15/959,050.
Preliminary Amendment filed Jul. 23, 2018 in U.S. Appl. No. 15/963,966.
Extended European Search Report dated Aug. 8, 2018 issued in Application No. EP 16744002.3.

\* cited by examiner

Z=−100 μm

MULTI-WELL FOURIER PTYCHOGRAPHIC AND FLUORESCENCE IMAGING

CROSS-REFERENCES TO RELATED APPLICATIONS

This is a non-provisional application claiming priority to and benefit of U.S. Provisional Patent Application No. 62/107,631, titled "Real-time Cell Culture Monitoring via Fourier Ptychographic Microscopy" and filed on Jan. 26, 2015 and U.S. Provisional Patent Application No. 62/107,628, titled "Development of 96-well Plate Fluorescence Imaging System" and filed on 26 Jan. 2015, which are both hereby incorporated by reference in their entireties and for all purposes; This application is also related to U.S. patent application Ser. No. 15/007,196 (issuing as U.S. Pat. No. 9,829,695 on Nov. 28, 2017, titled "ARRAY LEVEL PTYCHOGRAPHIC IMAGING" and filed on the same day as the present application, which is hereby incorporated by reference in its entirety and for all purposes.

FEDERALLY SPONSORED RESEARCH OR DEVELOPMENT

This invention was made with government support under Grant No. OD007307 awarded by the National Institutes of Health. The government has certain rights in the invention.

FIELD

Certain aspects are generally related to digital imaging, and more specifically, to imaging systems, devices, and methods for Fourier ptychographic and fluorescence imaging.

BACKGROUND

Live cell imaging and other cell culture monitoring is widely used in bioscience experiments for a better understanding of dynamic cellular behaviors such as migration, division, differentiation, interaction with the environment, and organelle-level events. Cell culture monitoring can also provide the opportunity to detect unanticipated cell death and contamination at an early stage to rescue failing cell culture in a timely manner.

For longitudinal studies, bioscientists have traditionally resorted to building a specialized incubation and imaging chamber onto a conventional microscope, and imaging the cultured cells directly on the microscope stage as discussed in http://www.zeiss.com/microscopy/en_us/products/microscope-components/incubation.html. This approach, however, is not only expensive, but occupies a significant amount of real estate in the lab. Furthermore, field-of-view and image resolution are coupled to the physical properties of the objective lens in the conventional microscope. Thus field-of-view and image resolution must be traded off when using this conventional microscope platform. Another conventional approach to cell culture monitoring is to incorporate imaging systems within incubators as discussed in http://www.essenbioscience.com/essen-products/incucyte/. Unfortunately, these conventional systems also employ a standard microscope. Moreover, mechanical scanning is used. As a result, it is difficult to obtain wide field of view and high resolution imaging at the same time in these conventional systems. In addition, these systems are expensive to build and maintain and their throughput is limited by the conventional microscope itself. That is, the number of resolvable pixels, characterized by the space-bandwidth product (SBP) accessible through a conventional microscope is typically limited to 10 megapixels. This SBP limitation constrains the rate of image acquisition or throughput achieved by the conventional systems.

Most recently, on-chip microscopes have been developed with the purpose of overcoming the SBP limit of the conventional microscope. These on-chip microscopes have demonstrated successful high resolution and large field-of-view (FOV) imaging of the cell cultures from within the incubator. Examples of these on-chip microscopes can be found at G. Zheng, S. A. Lee, Y. Antebi, M. B. Elowitz, and C. Yang, "The ePetri dish, an on-chip cell imaging platform based on subpixel perspective sweeping microscopy (SPSM)," Proc. Natl. Acad. Sci. U.S.A. 108(41), 16889-16894 (2011), J. H. Jung, C. Han, S. A. Lee, J. Kim, and C. Yang, "Microfluidic-integrated laser-controlled microactuators with on-chip microscopy imaging functionality," Lab Chip 14(19), 3781-3789 (2014), and C. Han, S. Pang, D. V. Bower, P. Yiu, and C. Yang, "Wide field-of-view on-chip Talbot fluorescence microscopy for longitudinal cell culture monitoring from within the incubator," Anal. Chem. 85(4), 2356-2360 (2013). However, these on-chip microscopes have the inherent limitation that cells need to be grown on top of the image sensor. This limitation is a marked departure from the conventional cell culture workflow. If culture cells or biological sample is imaged on top of the sensor chip, the surface is made with silicon-based material (usually silicon nitride), so cell culture environment changes. Even though a special layer may be coated onto the image sensor, the bottom layer of the surface is different from plastic or glass used in a conventional cell culture workflow. Furthermore, the imaging sensor surface is an active layer and making heat during operation. So the cell culture environment can be affected by the temperature change related with this heat unless the system is designed for the cooling. Other lensless imaging methods, such as digital in-line holography, can work without this restriction and can provide high imaging SBP in the brightfield mode, but the absence of optical focusing elements prevents them from having effective fluorescence imaging capability. Focusing elements are needed for effective fluorescence imaging capability since due fluorescence emissions are incoherent and of low intensity, which degrades the resolution of fluorescence images without any focusing elements. Examples of digital in-line holography can be found in W. Bishara, T. W. Su, A. F. Coskun, and A. Ozcan, "Lensfree on-chip microscopy over a wide field-of-view using pixel super-resolution," Opt. Express 18(11), 11181-11191 (2010), W. Bishara, U. Sikora, O. Mudanyali, T. W. Su, O. Yaglidere, S. Luckhart, and A. Ozcan, "Holographic pixel super-resolution in portable lensless on-chip microscopy using a fiber-optic array," Lab Chip 11(7), 1276-1279 (2011), and A. Greenbaum, U. Sikora, and A. Ozcan, "Field-portable wide-field microscopy of dense samples using multi-height pixel super-resolution based lensfree imaging," Lab Chip 12(7), 1242-1245 (2012).

SUMMARY

Certain aspects pertain to multi-well based (MWB) systems, devices, and methods of Fourier ptychographic and fluorescence imaging. In some aspects, multiple MWB systems can be implemented into an incubator. In some aspects, an MWB system has multiple imaging devices within a single body to image samples in parallel in a multi-well plate.

Certain aspects pertain to an imaging device for bright field Fourier ptychographic imaging and fluorescence imaging. The imaging device comprises a first fluorescence illumination source configured to provide excitation light of a first range of wavelengths to a transparent well. The imaging device further comprises an optical system having a pair of objectives positioned oppositely. The imaging device further comprises an image sensor configured to receive light propagated through the optical system from the transparent well. The image sensor is further configured to acquire a sequence of uniquely illuminated intensity measurements of light passing through a sample in the well based on sequential illumination at different illumination angles from a variable illumination source. The image sensor is further configured to acquire a first fluorescence image of the sample based on light emitted by the sample in response to excitation light of the first range of wavelengths. In certain implementations, the imaging sensor receives signals from a processor (e.g., of a controller) with control instructions for acquiring images.

Certain aspects pertain to a system for Fourier ptychographic imaging and fluorescence imaging. The system comprises a body configured to receive a multi-well plate and imaging devices arranged for one to one correspondence with wells in the multi-well plate. Each imaging device comprises a first fluorescence illumination source configured to provide excitation light of a first range of wavelengths to the corresponding well and an optical system with a pair of objectives positioned oppositely. Each imaging device further comprises an image sensor for capturing intensity measurements based on light received from the corresponding well. The system is configured to generate an improved resolution brightfield image of the sample using Fourier ptychographic reconstruction based on a sequence of uniquely illumination intensity measurements acquired during sequential illumination at different illumination angles by a variable illumination source. The system is also configured to generate a first fluorescence image based on light emitted by the sample in response to receiving excitation light of the first range of wavelengths.

Certain aspects pertain to an imaging method comprising sequentially illuminating the multi-well plate with plane wave illumination at a plurality of illumination angles. For each well in the well plate, the imaging method acquires a sequence of uniquely illuminated intensity measurements from light passing through a sample in the corresponding well based on sequential illumination at the plurality of illumination angles. In addition, for each well in the well plate, reconstructing with a Fourier ptychography reconstruction process an improved resolution brightfield image of the sample based on the sequence of uniquely illuminated intensity measurements. In certain implementations, the imaging method further comprises calibrating positions of light sources of a variable illumination source to locations of image sensors receiving light from wells in a multi-well plate.

These and other features are described in more detail below with reference to the associated drawings.

DETAILED DESCRIPTION

Figure 1:
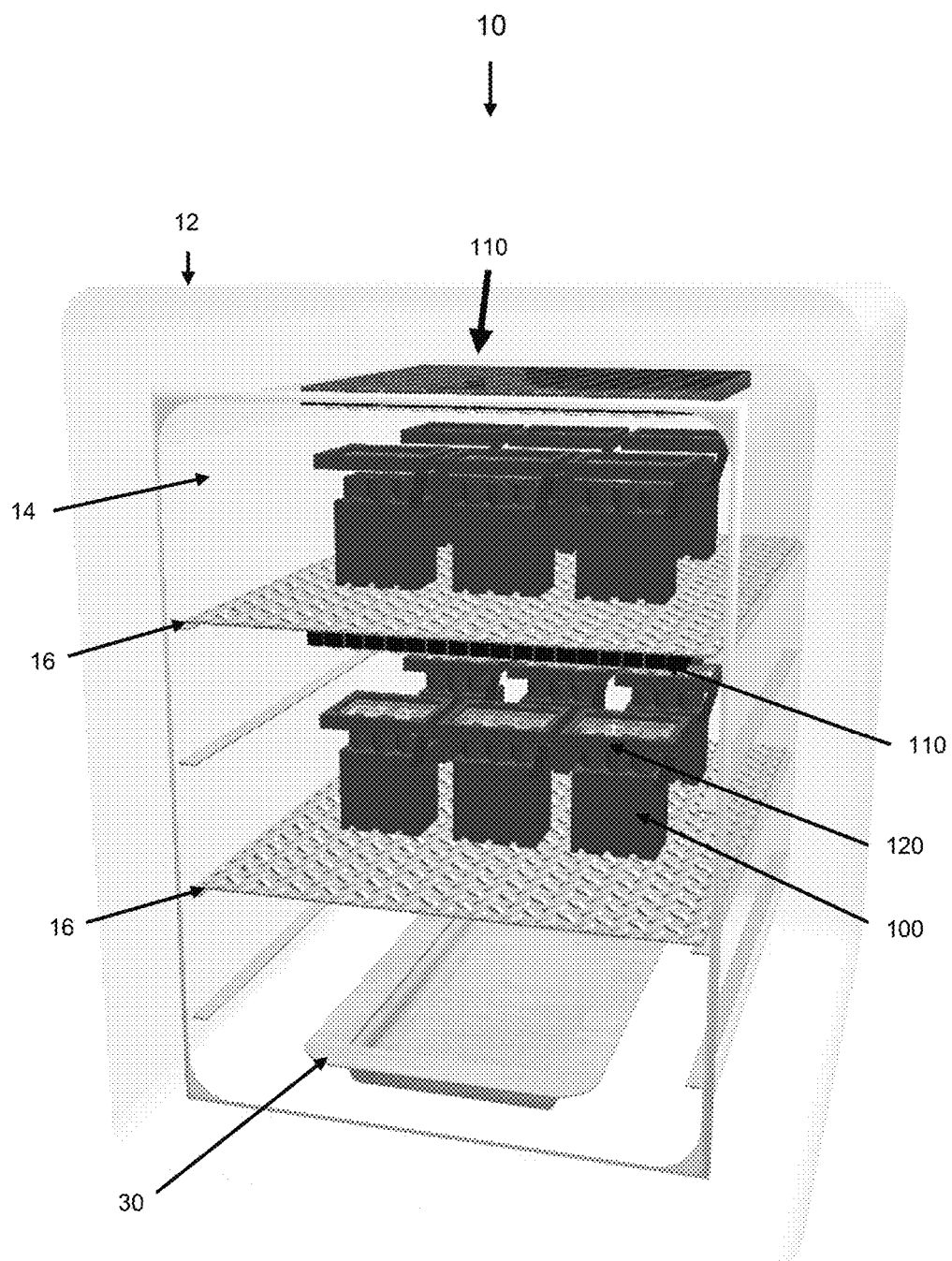
FIG. 1 is a schematic drawing of components of an incubator system with multiple WMB systems for Fourier ptychographic bright-field imaging and/or fluorescence imaging, according to an embodiment.

Different aspects are described below with reference to the accompanying drawings. The features illustrated in the drawings may not be to scale.

I. Introduction

Certain aspects pertain to multi-well based (MWB) systems, devices, and methods for high resolution Fourier ptychographic bright-field imaging and mid-resolution fluorescence imaging. In aspects, an MWB system includes a body designed to receive a multi-well plate (e.g., 6-well plate or a 12-well plate) and includes multiple imaging devices for imaging corresponding wells in the multi-well plate. In these aspects, each imaging device has one or more high power fluorescence illumination sources for providing fluorescence illumination to the corresponding well, an optical system with a pair of objectives (e.g., low NA objectives) positioned oppositely in an imaging column, and an image sensor. The image sensor receives light collected and focused from the corresponding well as propagated by the optical system. An LED matrix or other variable illumination source sequentially illuminates the wells in the well-plate from different illumination angles to provide Fourier ptychographic illumination. In some aspects, an emission filter is located between the pair of objectives to block excitation light from the one or more fluorescence illumination sources. In one aspect, the wavelength of the illumination from the variable illumination source falls within the passband of the emission filter so that image sensor can acquire a sequence of uniquely illuminated bright field images based on the Fourier ptychographic illumination and fluorescence images based on the Fluorescence illumination without having to remove the emission filter. A FP reconstruction process can be used to generate an improved resolution brightfield image of the sample in each well from the uniquely illuminated bright field images of the sample captured by the image sensor. Thus, certain MWB systems can generate both high-resolution bright-field images and mid-resolution fluorescence images of the samples in multiple wells in parallel. Since the imaging devices of certain MWB systems can be compact and arranged in parallel columns, they can have approximately the same footprint as the multi-well plate and multiple systems can be placed into a single incubator.

Fourier ptychographic (FP) techniques can be used to overcome the SBP limit of conventional imaging systems. Some examples of conventional microscopes systems that use FP imaging techniques are discussed in G. Zheng, R. Horstmeyer, and C. Yang, "Wide-field, high-resolution Fourier ptychographic microscopy," Nat. Photonics 7(9), 739-745 (2013), X. Ou, R. Horstmeyer, C. Yang, and G. Zheng, "Quantitative phase imaging via Fourier ptychographic microscopy," Opt. Lett. 38(22), 4845-4848 (2013), R. Horstmeyer and C. Yang, "A phase space model of Fourier ptychographic microscopy," Opt. Express 22(1), 338-358 (2014), X. Ou, G. Zheng, and C. Yang, "Embedded pupil function recovery for Fourier ptychographic microscopy," Opt. Express 22(5), 4960-4972 (2014), X. Ou, R. Horstmeyer, G. Zheng, and C. Yang, "High numerical aperture Fourier ptychography: principle, implementation and characterization," Opt. Express 23(3), 3472-3491 (2015), J. Chung, X. Ou, R. P. Kulkarni, and C. Yang, "Counting White Blood Cells from a Blood Smear Using Fourier Ptychographic Microscopy," PLoS One 10(7), e0133489 (2015), A. Williams, J. Chung, X. Ou, G. Zheng, S. Rawal, Z. Ao, R. Datar, C. Yang, and R. Cote, "Fourier ptychographic microscopy for filtration-based circulating tumor cell enumeration and analysis," J. Biomed. Opt. 19(6), 066007 (2014), and R. Horstmeyer, X. Ou, G. Zheng, P. Willems, and C. Yang, "Digital pathology with Fourier ptychography," Comput. Med. Imaging Graphics 42, 38-43 (2015), which are hereby incorporated by reference for the discussion.

Certain aspects pertain to an imaging device that can implement FP techniques for bright-field, high-resolution imaging and can also acquire mid-resolution fluorescence images. To implement the FP techniques, a variable illumination source (e.g., LED matrix) with a series of discrete light sources provides plane wave illumination sequentially at a series of illumination directions to the sample. An image sensor captures a sequence of intensity distribution measurements (raw intensity images) from light passing through the sample at different exposure times while the sample is sequentially illuminated at the different illumination directions. The intensity images can be combined in the spatial frequency domain using a Fourier ptychographic reconstruction process to render a high-resolution image. By using a low magnification (with low numerical aperture (NA)) objective as the collection element, the imaging device can improve resolution while maintaining a wide field-of-view.

In certain aspects, the imaging devices of an MWB system are configured for high throughput cell culture imaging. In these cases, the components of the imaging devices are designed and arranged into a single body for a simple and compact MWB system capable of imaging multiple samples in parallel. Since the MWB system is compact, multiple MWB systems can be embedded into an incubator system for parallel monitoring of many cell cultures. Since the imaging devices of this MWB system does not require that the sample be placed on top of the image sensor, a cell culture can be grown and imaged in a multi-well plate.

In certain aspects, the imaging devices of an MWB system use high resolution imaging techniques that tolerate experimental errors such as misalignment and/or defocus, which can be beneficial for long time monitoring (e.g., longitudinal studies) without interruption. In certain cases, imaging devices of an MWB system implement an imaging method with a calibration process that can correct misalignment of the multi-well plate and/or digital refocus the high resolution image as part of the FP reconstruction process. The digital refocusing capability available with the FP reconstruction process can be useful for small drift and mechanical instability of the well plate. This is a marked benefit to a user of the system since the user can retain and refocus images that might have been rejected with conventional imaging techniques. In addition, this eliminates the need for mechanical auto-focusing solutions and simplifies the imaging device. Some details of the digital refocusing capability of FP techniques is described in G. Zheng, R. Horstmeyer, and C. Yang, "Wide-field, high-resolution Fourier ptychographic microscopy," Nat. Photonics 7(9), 739-745 (2013), which is hereby incorporated by reference in its entirety. Since the components and their arrangement can be simple, these imaging devices can be compact and cost-effective. Systems with multiple imaging device units can be made cost-effectively and compactly to provide simultaneous imaging capability, for example. The ability to perform parallel imaging can boost the effective system SBP by a factor equal to the number of parallel units.

In certain aspects, the imaging devices of an MWB system are designed with a wide field-of-view that is large enough to monitor a representative part of the sample which is useful to make cell culture monitoring most effective in biological research. In some cases, imaging devices have a field-of-view in the range of 0.01 $mm^2$ to 100 $cm^2$. In certain aspects, imaging devices are designed to produce images at a resolution that is high enough to distinguish cellular changes of interest. In some cases, imaging devices have a spatial resolution of 2 μm to 10 μm.

II. Systems for Fourier Ptychographic Bright-Field Imaging and Fluorescence Imaging Certain aspects pertain to an incubator system comprising an incubator with an internal volume that can be loaded with one or more MWB systems. In certain cases, an MWB system has multiple imaging devices (also called imaging units) with vertical imaging columns arranged in parallel within a single body. As designed, the MWB system can simultaneously (in parallel) image samples in multiple wells of a multi-well plate loaded on the top of the body. Each imaging device of this MWB system is configured for both Fourier ptychographic bright-field high resolution imaging and mid-resolution fluorescence imaging of a sample in a corresponding well of a multi-well plate. An example of an incubator is a biological incubator having an internal volume of 200 liters.

In some cases, the incubator system has multiple horizontal shelves that are spaced apart horizontally in the internal volume. The horizontal shelves are sized and spaced apart to hold various equipment such as plates, flasks and/or one or more MWB systems. In one aspect, an incubator system has horizontal shelves sized and spaced apart so that one or more MWB systems can be loaded onto a horizontal shelf. In one example, the spacing between adjacent horizontal shelves is at least 250 mm apart. The incubator system also includes electrical connectors between the imaging devices in each of the MWB systems to a processor(s) (e.g., microprocessor) and/or power supply(ies).

In one aspect, the incubator system includes a variable illumination source (e.g., an LED matrix) located on a surface or other structure above a horizontal shelf that can be loaded with one or more MWB systems. In one example, the horizontal shelf that will be loaded is a lower shelf of the incubator. In this case, the LED matrix or other variable illumination source faces downward and is located on a bottom surface of the horizontal shelf above this lower shelf. In another case, the horizontal shelf being loaded is the top shelf of the incubator. In this case, the LED matrix or other variable illumination source faces downward and is located on the internal surface of the upper horizontal wall of the internal volume of the incubator. Although certain examples of an incubator system are described herein with an incubator of two horizontal shelves with six MWB systems per shelf, it would be understood that the disclosure is not so limiting and that other examples of an incubator system can have an incubator configured with more or fewer shelves and/or load more or fewer MWB systems on a horizontal shelf.

FIG. 1 is a schematic drawing of components of an incubator system 10 with multiple MWB systems 100 for Fourier ptychographic bright-field imaging and/or fluorescence imaging, according to an embodiment. The incubator system 10 comprises an incubator 12 having an internal volume 14 (e.g., 200 liters), two horizontal shelves 16 in the internal volume 14, and a water tray 30 proximal the lower surface of the incubator 12. The horizontal shelves 16 are spaced apart (e.g., at least 250 mm apart). Twelve (12) MWB systems 100 for Fourier ptychographic bright-field imaging and/or fluorescence imaging are shown loaded onto two horizontal shelves 16 (six to a shelf) in the internal volume 14 of the incubator 12. The incubator system includes two variable illumination sources 110 in the form of color LED matrixes. A first variable illumination source 110 is configured to provide FP sequential illumination to the six MWB systems 100 loaded onto the top horizontal shelf 16 of the incubator 12. The first variable illumination source 110 is attached to the bottom surface of the upper horizontal wall of the internal volume 14 of the incubator 12. The second variable illumination source 110 is attached to the bottom surface of the upper horizontal shelf 16 above the lower horizontal shelf loaded with the MWB systems 100. The incubator system 10 also includes electrical connections (shown in FIG. 2D) between the MWB systems 100 and a processor(s) and/or power supply(ies).

In the illustrated example, six (6) MWB systems 100 on each horizontal shelf 16 share a variable illumination source 110. The variable illumination source 110 provides sequential illumination at different illumination angles to the samples in the well plates of the MWB systems 100. In other examples, each MWB system 100 has its own variable illumination source 110 or shares with more or fewer MWB system 100 systems.

Certain aspects pertain to an MWB system with multiple parallel imaging devices. Each imaging device has vertically aligned components so that multiple parallel imaging devices can be arranged in a single body to be able to simultaneously image samples in multiple wells in a multi-well plate loaded on the top of the body. Each imaging device is configured for both Fourier ptychographic brightfield high resolution imaging and mid-resolution fluorescence imaging of a sample in a single well of the multi-well plate (e.g. six (6) well plate or twelve (12) well plate). The body of this MWB system is designed to accept and hold the multi-well plate. For example, the body may include a lip in the shape of the outer perimeter of the multi-well plate for seating the multi-well plate.

As used herein, a multi-well plate refers to a flat plate of transparent material having multiple wells, each well for receiving and containing a sample. Generally the wells are of a round or square shape with an open top end for receiving the sample and a closed bottom. In one example, each well of the multi-well plate is a round with a diameter of thirty-six (36) mm. In one example, each well of the multi-well plate is a round with a diameter of thirty-four (34) mm. In one example, each well of the multi-well plate is a round with a diameter of twenty-three (23) mm. A sample being imaged in a well can be comprised of one or more objects and/or one or more portions of an object. Each object may be, for example, a biological entity, an inorganic entity, etc. Some examples of biological entities that can be imaged include whole cells, cell components, microorganisms such as bacteria or viruses, and cell components such as proteins. An example of an inorganic entity that can be imaged is a semiconductor wafer. The sample may be provided in a medium such as a liquid.

In certain aspects, an imaging device of an MWB system receives sequential illumination from a variable illumination source (or shares a variable illumination source with other imaging device) and includes at least one high power fluorescence illumination source configured to provide excitation light and an imaging part with a: imaging optical system arranged in a vertical column. In some cases, the imaging device or MWB system includes the variable illumination source. The imaging optical system is a 1:1 system in certain implementations. Other ratios can be used. In some cases, the imaging optical system is designed to match the resolution of the objective lenses with half of the pixel size of the image sensor.

Although certain examples of an MWB system are described herein as having six (6) imaging devices for independent imaging samples in six wells in a 6-well plate, it would be understood that the disclosure is not so limiting and that MWB systems can have fewer or more imaging devices (units). For example, an MWB system can have 12 imaging devices for imaging samples in 12 wells of a 12-well plate.

As used herein, a variable illumination source refers to a device that can be configured to provide plane wave illumination sequentially at n different illumination angles to a sample of one or more MWB systems. Each illumination angle corresponds to a location of a corresponding region in the Fourier domain. The variable illumination source comprises an arrangement of multiple discrete light elements at different locations, for example, in a two-dimensional grid, a line array, concentric circles, etc. In some cases, each discrete light element includes multiple light sources, for example, a red light source, a blue light source, and a green light source. In FIG. 1, for example, the variable illumination source 110 is a three color LED (two-dimensional) matrix where each LED includes a red light source, a blue light source, and a green light source. By sequentially illuminating n different discrete elements (or groups thereof) at different locations, the variable illumination source provides plane wave illumination at n different illumination angles. In one aspect, the variable illumination source is in the form of a two-dimensional matrix, (e.g., 32×32 matrix, 100×100 matrix, 32×64 matrix, 64×64 matrix, and 128×128 matrix).

To provide sequential illumination, the variable illumination source illuminates different discrete elements (or groups thereof) at different locations during the FP image acquisition process. The order and timing of the activation of the discrete elements of the variable illumination source are provided in illumination instructions. In one example, the order of illumination is a circular pattern starting/ending from/to the center position. In another example, the order of illumination follows a serpentine patter from top row to bottom row.

Although typically the light sources of a variable illumination source are coherent light sources, in one aspect, sources with finite-sized active areas that emit incoherent light can be used. This light that is incoherent at the finite-sized source will form a partially coherent field upon propagation to the sample plane, and computational corrections can be applied in the Fourier reconstruction process to account for the partially coherent nature of the incident illumination.

In some aspects, the variable illumination source provides visible light. An example of a variable illumination source that provides visible light is a light emitting diode (LED) matrix. In this example, each LED is a light element. Another example of a variable illumination source that provides visible light is a liquid crystal display (LCD).

Each imaging device of an MWB system includes a fluorescence illumination part having one or more high power fluorescence illumination sources for providing fluorescence illumination, which is excitation light for activating fluorophores in the sample. Each high-power fluorescence illumination source is designed to generate excitation light of a certain range of wavelengths. In multi-color fluorescence imaging examples, each imaging device has a separate high power fluorescence illumination source for each band being imaged.

Each high-power fluorescence illumination source includes one or more high power light sources (e.g., high-power LEDs) and an excitation filter for passing excitation light of a range of wavelengths and blocking other wavelengths. In one example, a high-power fluorescence illumination source includes six (6) high-power LEDs. In one example, a high-power fluorescence illumination source includes one (1) high-power LED. In one example, a high-power fluorescence illumination source includes multiple high-power LEDs. For single color (band) fluorescence imaging, each imaging device has at least one high power fluorescence illumination source with a high power light source(s) (e.g., LED) and an excitation filter for passing excitation light of a certain range of wavelengths and blocking other wavelength. For multi-color (multi-channel) fluorescence imaging, the number of sets of high power light source(s) and filters increases by the number of fluorescence channels. For multi-band fluorescence imaging, a different high power fluorescence illumination source is used for each fluorescence channel. Each high power fluorescence illumination source is illuminated at a different image acquisition time so that a monochromic fluorescence image is separately acquired for each channel. A processor can implement instructions to convert a monochromic fluorescence image into a color fluorescence image. In multi-color embodiments, a processor can generate a multi-color fluorescence image by overlaying image data from multiple color fluorescence. For example, a processor can generate a blue-green fluorescence image by overlaying image data from a blue fluorescence image and a green fluorescence image.

To provide fluorescence illumination while maintaining a compact system, the one or more high power fluorescence illumination sources of an imaging device can be located at the side of the well being illuminated, according to certain aspects. At this side location, the one or more high power fluorescence illumination sources can shine excitation light to the sample directly from the side of the well without blocking the light path from the variable illumination source. In one aspect, the one of more high-power fluorescence illumination sources of each imaging device are installed into or on the side of the multi-well plate. Generally, the one or more high-power fluorescence illumination sources (both high power light source(s) and excitation filter) are inclined toward the well center so the path of the direct excitation light goes to the center of each well (i.e. the region of interest of each well). In some cases, the one or more high-power fluorescence illumination sources are positioned at an angle from the plane at the bottom inner surface of the well. The angle is selected to be out of the numerical aperture (NA) of the first objective lens to prevent the acceptance of the powerful unscattered excitation light. In one aspect, the angle is 6 degrees. In another aspect, the angle is 4.6 degrees.

In one aspect, the LED matrix or other variable illumination source is shared by multiple imaging devices and/or multiple MWB systems. In this aspect, a single illuminated light element (e.g., LED) can provide plane wave illumination to multiple imaging devices and/or MWB systems simultaneously. For example, the incubator system 10 described with respect to FIG. 1 has six (6) MWB systems 100 on each horizontal shelf 20, all six MWB systems 100 sharing the variable illumination source 110 on a surface above the horizontal shelf 20. With sharing configurations, the effective footprint of each imaging device is reduced, which makes more parallel experiments possible in the limited internal volume inside the incubator. This sharing configuration also frees up space between the multi-well plate and the variable illumination source, which provides space for easy access to the multi-well plate and eliminates the possibility of unnecessary reflection from additional surfaces. According to certain aspects, an MWB system includes parallel sets of vertically aligned imaging devices in a single body. The imaging part of each imaging device includes an optical system and an image sensor of, for example, a CMOS sensor camera. The optical system has a pair of objectives positioned oppositely in an imaging column and an emission filter between the objectives. The objectives include a first collection objective that collects light issuing from the sample and a second focusing objective that focuses light to the image sensor. In certain implementations, the optical system is a 1:1 system to allow for 1-to-1 imaging of the sample onto the image sensor. The 1:1 imaging system provides for wide field of view imaging of the sample in the well by using a first collection objective with a low magnification (low NA). In some cases, optical system is designed for a field of view to image over an area of a well having a diameter of about 36 mm or greater.

In one example, the first collection objective has an NA of about 0.1. In another example, the first collection objective has an NA of about 0.2. In another example, the first collection objective has an NA of about 0.4. In another example, the first collection objective has an NA of less than 0.05. In another example, the first collection objective has an NA of less than 0.01.

By using two of the same objectives, the imaging device can made more compact by maintaining the same footprint and without reducing the resolution of the objective lens. Also, by making the infinite plane between the two objective lenses, the imaging devices can be fine tuned to focus each well independently without changing the magnification of each well. In one example, each objective is an Olympus 4×/NA 0.1 objective lens.

In some cases, the optical system also has an emission filter between the first objective and the second objective at the Fourier plane of the sample. The emission filter blocks excitation light from the one or more high-power fluorescence illumination sources of the device. In one aspect, the emission filter is an interference filter. In an example of an imaging device for single channel fluorescence imaging, the emission filter is a band pass or a long pass filter. In an example of an imaging device for the multi-channel fluorescence imaging, the emission filter is a multiband filter.

In one aspect, the range of wavelengths of the brightfield illumination from the variable illumination source fall within the passband of the emission filter so that the emission filter passes light from the variable illumination source that passes through the sample in the well. In this case, the image sensor can acquire both a sequence of uniquely illuminated bright field images and fluorescence images while leaving the emission filter in place. In another aspect, the range of wavelengths of the brightfield illumination from the variable illumination source do not fall within the passband of the emission filter and the emission filter is removed during the FP image acquisition process.

According to certain aspects, each imaging device of an MWB system includes an image sensor (e.g., CMOS sensor) that can acquire n uniquely illuminated intensity images during the FP image acquisition process and that can acquire a fluorescence image during each fluorescence image acquisition process. The image sensor acquires each image by measuring an intensity distribution of light incident the sensing area of image sensor over an exposure time. The image sensor is part of a USB camera in many examples. The image sensor is a monochromic detector.

In one aspect, the size of the image sensor matches with the field number of the objective lens and/or the size of each sensor element (pixel) matches with half of the resolution which the objective can provide. This sizing allows the imaging device to make full use of objective field of view. In order to make full use of the SBP of the optical system, the pixel size of the sensor should be equal or smaller than half of the resolution of the objective lens, and the size of the sensor surface should be equal or larger than the field of view of the objective. When both of the above condition is equal, the system is well designed and most effective.

During each fluorescence image acquisition process, the image sensor acquires a monochromic fluorescence image while a high power fluorescence illumination source provides fluorescence illumination (excitation light) of a range of wavelengths. The monochromic image is converted into a color fluorescence image by the processor. If the MWB system has multiple high-power fluorescence illumination sources, the image sensor can acquire multiple monochromic fluorescence images, each fluorescence image while one of the high-power fluorescence illumination sources provides fluorescence illumination.

An image acquisition (sample) time refers to a time during the exposure duration of the image sensor during which the image sensor measures an intensity distribution to capture a single intensity image. During an FP image acquisition process, the image sensor captures n uniquely illuminated intensity images (e.g., n=1, 2, 5, 10, 20, 30, 50, 100, 1000, 10000, etc.). In some cases, the image sensor samples images at a uniform sampling rate during an image acquisition process. In one case, the sampling rates may be in the range of 0.1 to 1000 frames per second.

As mentioned above, the image sensor captures n uniquely illuminated intensity images during an FP image acquisition process. Each of the plurality of n uniquely illuminated intensity images captured by the image sensor is associated with a region in Fourier space. In Fourier space, the neighboring regions share an overlapping area over which they sample the same Fourier domain data. In one example, the neighboring regions in Fourier space overlap by about 2% to about 99.5% of the area of one of the regions. In another example, the neighboring regions in Fourier space overlap by about 65% to about 75% of the area of one of the regions. In another example, the neighboring regions in Fourier space overlap by about 65% of the area of one of the regions. In another example, the neighboring regions in Fourier space overlap by about 70% of the area of one of the regions. In another example, the neighboring regions in Fourier space overlap by about 75% of the area of one of the regions.

Figure 2A:
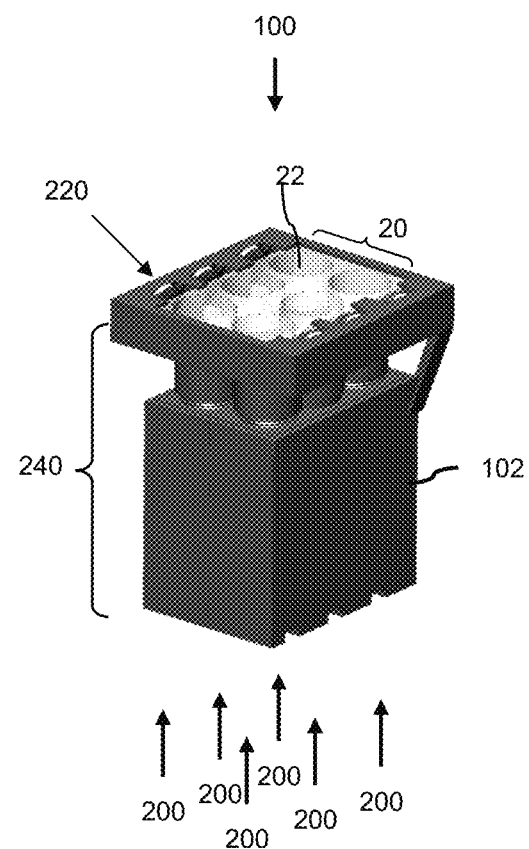
FIG. 2A is a schematic drawing of components of one of the MWB systems shown in FIG. 1, according to an embodiment.
Figure 2B:
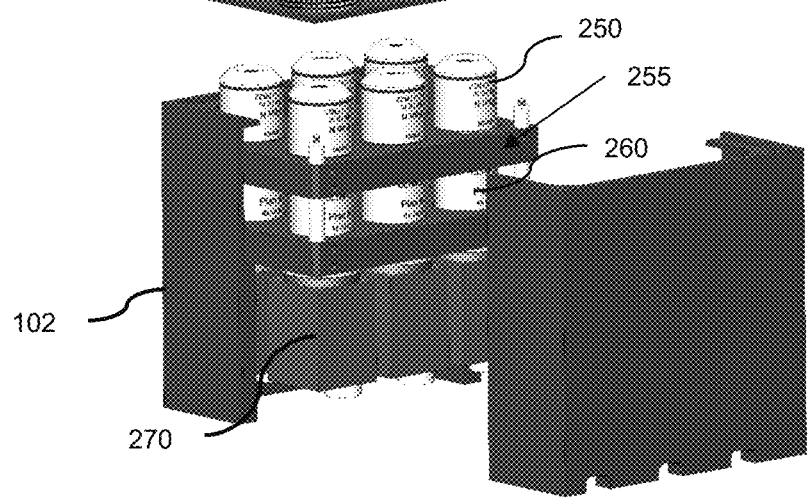
FIG. 2B is a schematic drawing of an exploded view of some of the components of the MWB system shown in FIG. 2A.

FIG. 2A is a schematic drawing of components of one of the MWB systems 100 shown in FIG. 1, according to an embodiment. The illustrated MWB system 100 is designed to be compatible with a 6-well plate 20. The MWB system 100 is comprised of six (6) imaging devices 200 arranged in parallel within a single body 102. As designed, the six imaging devices 200 can image samples in the six wells 22 of the 6-well plate 20. In FIG. 2A, the 6-well plate 20 is loaded into the top of the body 102 of the MWB system 100. FIG. 2B is a schematic drawing of an exploded view of some of the components of the MWB system 100 shown in FIG. 2A.

In certain aspects, each imaging device of an MWB system includes an FP illumination part, a fluorescence illumination part, and an imaging part. In FIGS. 2A and 2B, the FP illumination part is in the form of a variable illumination source 110 shared with other MWB systems 100. The variable illumination source 110 provides FP illumination i.e. sequential illumination at different illumination angles to the samples within the 6-well plates 20 of the MWB systems 100 on a horizontal shelf 16.

In FIGS. 2A and 2B, each imaging device 200 also includes a fluorescence illumination part in the form of a high power fluorescence illumination source 220. The high power fluorescence illumination source 220 is configured to provide excitation light (fluorescence illumination) to the well 22 from the side of the well-plate 20. In one aspect, the high power fluorescence illumination source 220 is installed into or on the side of the well-plate 20.

Figure 2C:
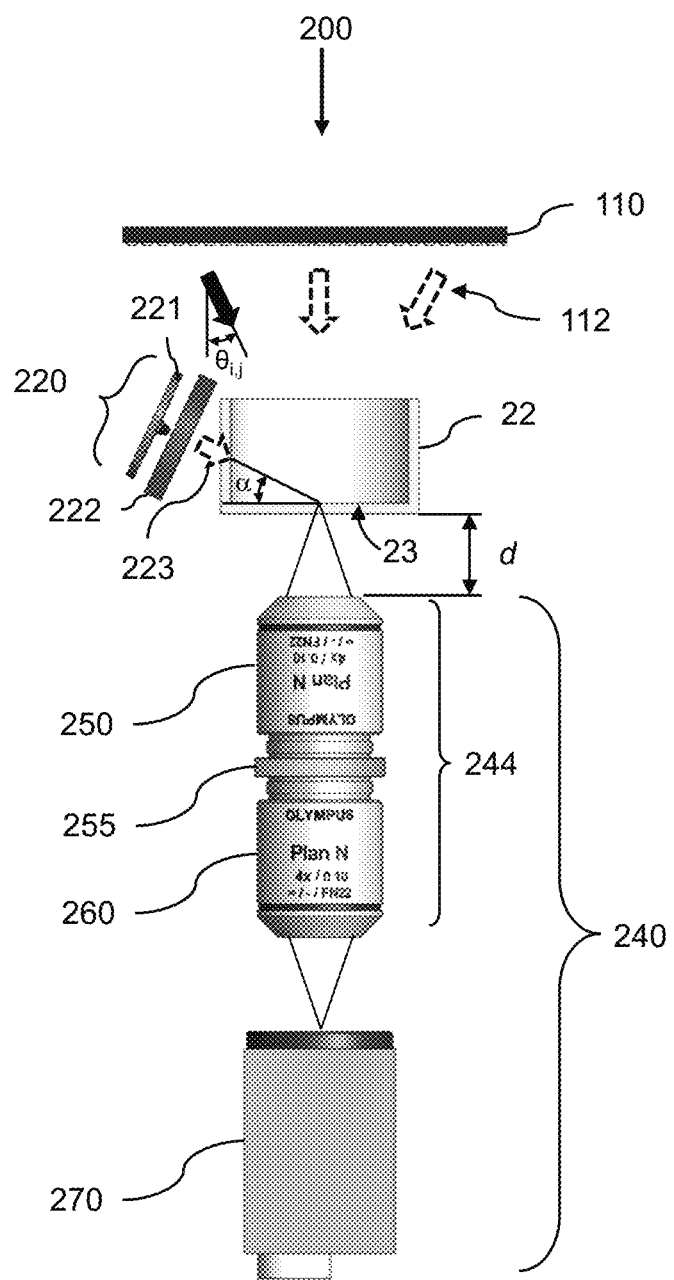
FIG. 2C is a schematic drawing of a side view of components of the imaging device of the MWB system shown in FIGS. 2A and 2B.

In FIGS. 2A and 2B, each imaging device 200 also includes an imaging part 240. The imaging part 240 includes an optical system and an image sensor 270. In FIGS. 2A, 2B, and 2C, each of the image sensors is in a 5 MP CMOS camera (e.g., Imaging Source, DMK 23UP031 with a pixel size of 2.2 µm). The optical system has a pair of the same objectives (e.g., Olympus 4×, NA0.1 or other low magnification objective) including a first objective 250 and a second objective 260 positioned oppositely and forming a vertical imaging column. This 1:1 imaging system allows for 1-to-1 imaging of the sample onto the image sensor 270. In order to have large field-of-view of imaging, the objectives, 250 and 260, are of low magnification. In one example, each of the objectives 250, 260 has an NA of about 0.10. In one example, each of the objectives 250, 260 has an NA of about 0.08. In one example, each of the objectives 250, 260 has an NA of about 0.13. Some examples of objectives 250 and 260 are commercially available at low cost.

The 1:1 optical system also includes an emission filter 255 located between the first objective 250 and the second objective 260. The emission filter 255 blocks excitation light from the high power fluorescence illumination source 220. In the illustrated example, the range of wavelengths of the brightfield illumination from the variable illumination source 110 fall within the passband of the emission filter 255 so that image sensor 270 can acquire both a sequence of uniquely illuminated bright field images and fluorescence images without removing the emission filter 255.

Each imaging device 200 shown in FIGS. 2A and 2B can capture a sequence of raw bright-field images using the image sensor 270 while the variable illumination source provides sequential illumination from different illumination angles. In one aspect, the image sensor 270 captures raw images sequentially while different LEDs light up in turn. Each raw bright-field image is generally of poor resolution since the objectives 250 and 260 are of low magnification. Due to the low magnification of the first objective 250, a large field-of-view of the sample can be imaged. The imaging device 200 can use Fourier ptychographic (FP) techniques to generate a high-resolution bright field image of the sample with the sequence of low resolution intensity images acquired by the image sensor. Using FP techniques, the uniquely illuminated raw intensity images are stitched together in the Fourier domain using a phase retrieval operation in the FP reconstruction process, which results in the high-resolution bright-field image. Details of the FP reconstruction process can be found in G. Zheng, R. Horstmeyer and C. Yang, "Wide-field, high-resolution Fourier ptychographic microscopy," Nature Photonics, 2013, which is hereby incorporated by reference in its entirety. Some details of the FP reconstruction process can be found in Section III.

Each imaging device 200 in FIGS. 2A and 2B can monitor the sample (e.g., cell culture) located in each well 22 using both high resolution and wide field of view imaging and mid-resolution fluorescence imaging with the approximate system footprint of a 6-well plate. By using an optical system with the same objectives 250 and 260 in a vertical imaging column, the imaging device 200 is reduced in size to allow for spacing (e.g., on 30 mm centers) in the MWB system 100 of less than a spacing of a 6-well plate. This configuration allows for assigning an imaging device 200 to each well 22 of the 6-well plate 20 with both high resolution FP imaging and mid-resolution fluorescence imaging (single or multi-band). With this configuration, the MWB system 100 can image multiple wells in a multi-well plate simultaneously without the use of any mechanical movement is typically needed in conventional systems used to image multi-well plates.

FIG. 2C is a schematic drawing of a side view of components of the imaging device 200 of the MWB system 100 shown in FIGS. 2A and 2B, according to an embodiment. The imaging device 200 comprises a variable illumination source 110 for providing FP sequential illumination 112. As used herein, FP sequential illumination refers to plane wave illumination at n different illumination angles sequentially provided during a FP raw image acquisition cycle. In one aspect, FP sequential illumination is accomplished by sequentially illuminating different discrete light elements (e.g., LEDs) at different locations of the variable illumination source 110. In FIG. 2C, the variable illumination source 110 is shown providing illumination at three different illumination angles at three image acquisition times by illuminating different light elements, one by one sequentially. FIG. 2C is depicted at an acquisition time $t_i$, where i=1 to n. At this acquisition time, $t_i$, plane wave illumination depicted by the solid arrow is being provided by the variable illumination source at an illumination angle, $\theta_i$. The dashed arrows depict plane wave illumination at other acquisition times as provided by the variable illumination source 110.

The imaging device 200 also includes a high power fluorescence illumination source 220 for providing excitation light 223. The high power fluorescence illumination source 220 is installed to provide excitation light 223 from the side of the well 22. The high-power fluorescence illumination source 220 includes high-power LEDs 221 (e.g., six high-power LEDs) and an excitation filter 222. The excitation filter 222 passes the excitation light 223 and blocks other wavelengths. The high-power fluorescence illumination source 220 is positioned to direct excitation light 223 at a small angle, a, from a plane at the bottom inner surface 23 of the well 22 to prevent much of the excitation light 223 from being collected by the first objective 250. At the acquisition time, $t_i$, depicted in the illustrated example, the high-power fluorescence illumination source 220 is not currently providing excitation light 223 as depicted by the dashed arrow. Excitation light 223 is provided at another image acquisition time.

The imaging device 200 also includes an imaging part 240 with an optical system 244, and an image sensor 270 of, for example, a USB connected camera. The optical system 244 includes a first objective 250 and a second objective 260 that form an imaging column. The objectives 250 and 260 are the same and positioned oppositely to form an imaging column that allows 1-to-1 imaging of the sample onto the image sensor 270 of the USB connected camera. For large field-of-view of imaging, the objectives, 250 and 260, are of low magnification. The 1:1 optical system 244 also includes an emission filter 255 located between the first objective 250 and the second objective 260 at the Fourier plane of the sample. The emission filter 255 blocks excitation light from the high power fluorescence illumination source 220.

Figure 2D:
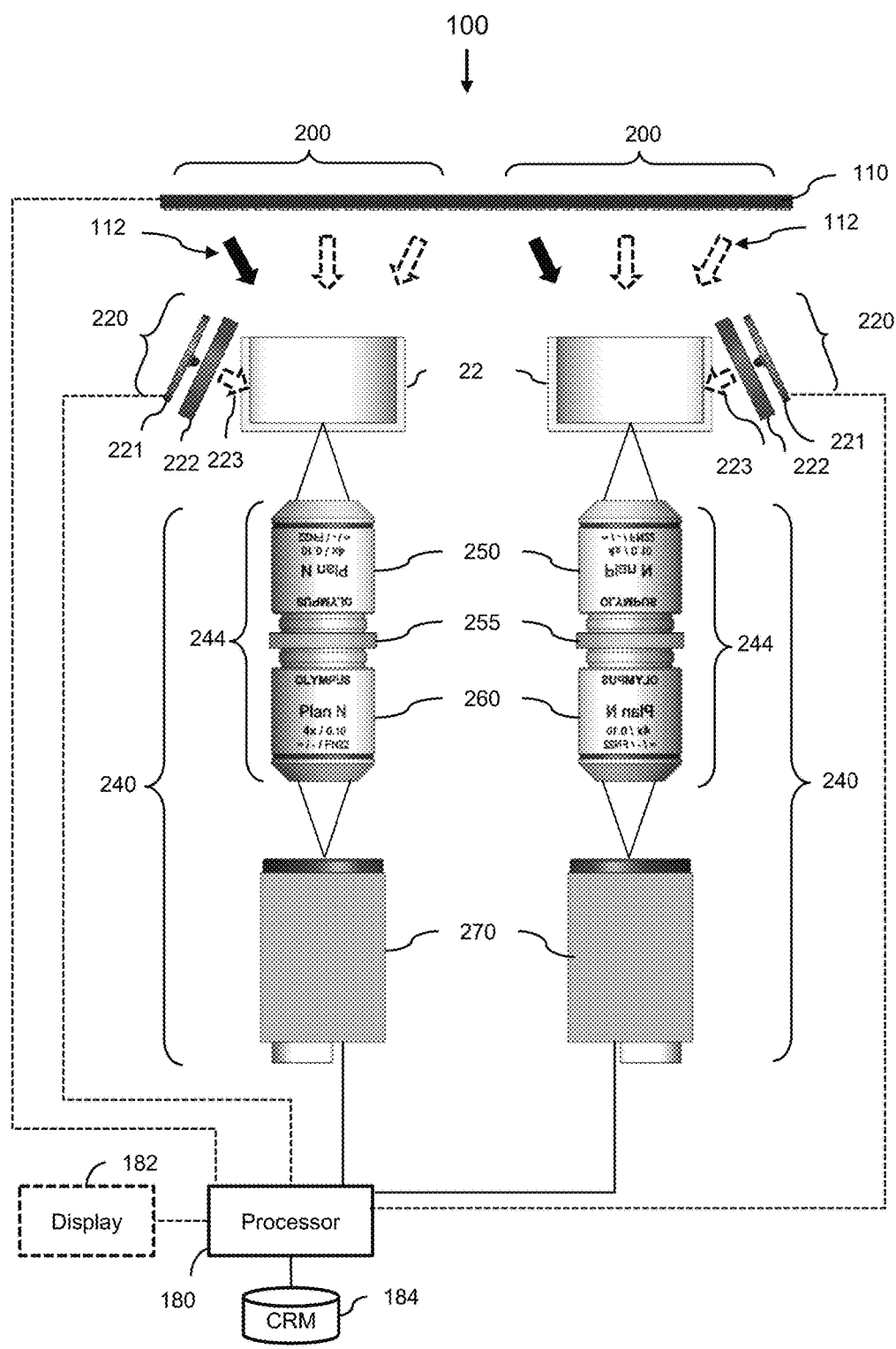
FIG. 2D is a schematic drawing of a side view of components of the MWB system shown in FIGS. 2A, 2B, and 2C, and also a processor, computer readable medium (CRM), and an optional display, according to an embodiment.

FIG. 2D is a schematic drawing of a side view of components of the MWB system 100 shown in FIGS. 2A, 2B, and 2C, and also including a processor 180, computer readable medium (CRM) 182, and an optional display 182 (denoted by a dashed line), according to an embodiment. In this view, two of the imaging devices 200 of the MWB systems 100 are shown sharing a variable illumination source 110 for providing FP sequential illumination 112 to the wells 22 of the 6-well plate 20 (shown in FIGS. 2A and 2B). In FIG. 2D, the variable illumination source 110 is shown providing illumination at three different illumination angles at three image acquisition times to each well 22 by illuminating different pairs of light elements, each pair sequentially. At the acquisition time depicted in the illustrated example, plane wave illumination is provided by the variable illumination source 110 from a pair of light elements of the variable illumination source 110. The dashed arrows depict plane wave illumination at other acquisition times.

Each imaging device 200 includes a high power fluorescence illumination source 220 for providing excitation light 223 from the side of the well 22 of each imaging device 200. Each high-power fluorescence illumination source 220 includes high-power LEDs 221 and an excitation filter 222 for passing excitation light 223 and blocking other wavelengths. The high-power fluorescence illumination source 220 is positioned to direct excitation light 223 at a small angle (shown in FIG. 2C) from a plane at the bottom inner surface 23 of the well 22. At the acquisition time, $t_i$, depicted in the illustrated example, the high-power fluorescence illumination source 220 is not providing excitation light 223 as depicted by the dotted arrow. That is, at the time shown in this illustrated example, the variable illumination source 110 is turned on and providing plane wave illumination 112 from a pair of light elements to the wells 22 and the high power fluorescence illumination source 220 is not turned on.

Each imaging device 200 also includes an imaging part 240 with an optical system 244, and an image sensor 270 of, for example, a USB connected camera. The optical system 244 includes a first objective 250 and a second objective 260 that form an imaging column. The objectives 250 and 260 are the same and positioned oppositely to form an imaging column that allows 1-to-1 imaging of the sample onto the image sensor 270 of the USB connected camera. For large field-of-view of imaging, the objectives, 250 and 260, are of low magnification. The optical system 244 also includes an emission filter 255 located between the first objective 250 and the second objective 260 at the Fourier plane of the sample. The emission filter 255 blocks excitation light from the high power fluorescence illumination source 220. In FIG. 2C, the emission filter 255 is between the objectives 150 and 160 at the Fourier plane of the sample.

FIG. 2D also shows the processor 180, computer readable medium (CRM) 184, and optional display 182 that is shared by one or more of the MWB systems 100 of the incubator system 10 shown in FIG. 1. The CRM 184 is in communication with the processor 180. The optional display 182 is in communication with the processor 180. The processor 180 is also in communication with each of the image sensors 270. Optionally, the processor 180 is also in communication with the variable illumination source 110 and/or the high power fluorescence illumination sources 220 as denoted by dotted lines. In one aspect, the processor 180, display 182 and CRM 184 are components of a computing device such as, for example, a smartphone, laptop, desktop, tablet, and the like.

During an exemplary operation of the MWB system 100 shown in FIGS. 2A-2D, each image sensor 270 captures a sequence of n uniquely illuminated intensity images during FP sequential illumination at n illumination angles. For example, a sequence of one hundred sixty nine (169) images from sequential illumination at one hundred sixty nine (169) illumination angles from turning on each LED in a two-dimensional 13×13 LED matrix. The processor 180 stiches the data together from the sequence of n uniquely illuminated intensity images in the spatial frequency domain using a FP reconstruction process to render a higher resolution brightfield image of the sample in the well 22 associated with the image sensor 270. The MWB system 100 performs fluorescence imaging by illuminating the sample with a different high power fluorescence illumination source for each fluorophore being activated and associated fluorescence image being captured. In one case, the bright-field illumination wavelength of the variable illumination source falls within the pass band of the emission filter 255 and the image sensor 270 can collect both brightfield and fluorescence images while the emission filter 255 remains in place between the objectives 250 and 260. In another case, the emission filter 255 is inserted between the objectives 250 and 260 before the fluorescence imaging cycle and/or removed before an FP image acquisition process.

In single band embodiments, the imaging device of an MWB system need only include a single high power fluorescence illumination source. For example, the imaging device 100 shown in FIG. 2A has a single high-power fluorescence illumination source that includes six high power LEDs and a first excitation filter that passes a first range of wavelengths. In this aspect, the imaging device also includes a single band emission filter at the Fourier plane of the one-to-one optical system between the first objective and the second objective. The single band emission filter blocks excitation light of the first range of wavelengths.

In dual band embodiments, an imaging device has at least two high power fluorescence illumination sources: a first high-power fluorescence illumination source and a second high-power fluorescence illumination source. The first high-power fluorescence illumination source has a high power light source and a first excitation filter that passes excitation light of a first range of wavelengths. In one case, the first range of wavelengths is a range between 320 nm and 380 nm. In another case, the first range of wavelengths is a range between 410 nm and 460 nm. In another case, the first range of wavelengths is a range between 470 nm and 500 nm. The second high-power fluorescence illumination source has a high power light source and a second excitation filter that passes excitation light of a second range of wavelengths. In one case, the second range of wavelengths is a range between 470 nm and 500 nm. In another case, the second range of wavelengths is a range between 570 nm and 600 nm. In another case, the second range of wavelengths is a range between 450 nm and 500 nm. In dual band embodiments, the imaging device also includes a dual band emission filter at the Fourier plane of the one-to-one optical system between the first objective and the second objective. The dual band emission filter blocks excitation light of a first range of wavelengths and blocks excitation light of the first range of wavelengths.

In dual band embodiments, the imaging device can generate a first monochromic fluorescence image based on the first range wavelengths and a second monochromic fluorescence image based on the second range of wavelengths. In one aspect, a processor implements instructions to convert one or both of the monochromic fluorescence images into color fluorescence images. The processor can implement instructions to combine the color fluorescence images into a dual-color fluorescence images. This dual-color fluorescence image is useful in biological tests to distinguish between different features of the sample displayed in different colors.

Figure 3A:
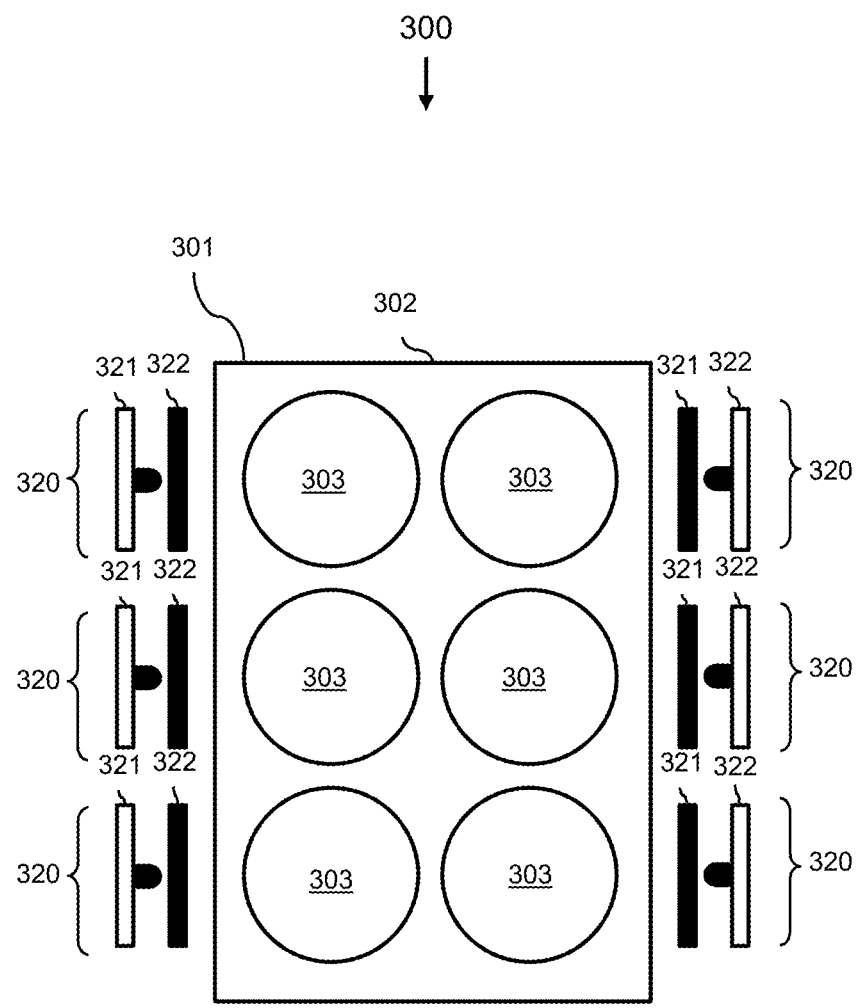
FIG. 3A is a schematic drawing of a plan view of components an MWB system configured for single band fluorescence imaging, according to an embodiment.

FIG. 3A is a schematic drawing of a plan view of components an MWB system 300 configured for a single band fluorescence imaging, according to a single band embodiment. Components of the MWB system 300 are similar to those described with respect to FIGS. 2A, 2B, 2C, and 2D. In this example, the imaging devices of the MWB system 300 have a single band emission filter (not shown) between the objectives. The illustrated MWB system 300 comprises six (6) of the same imaging devices arranged within a body 301 to be able to image samples in all six wells 303 in the 6-well plate 302 loaded on top of the body 301. Each of the imaging devices includes a high power fluorescence illumination source 320 for providing excitation light of a first range of wavelengths. The high power fluorescence illumination sources 320 are installed to provide the excitation light from the side of the 6-well plate 302 proximal the well 303 with the sample being imaged. The high power fluorescence illumination source 320 is directed to the center of the well 303. Each high power fluorescence illumination source 320 includes a high-power light source (e.g. LED) 321 and an excitation filter 322. The excitation filter 322 passes excitation light of the first range of wavelengths and blocks other wavelengths. During the fluorescence imaging method, the high-power light sources (e.g. LED) 321 of the MWB system 300 are turned on and the MWB system 300 can acquire a fluorescence image of each sample in the six wells 303. The first fluorescence image is based on emissions collected from fluorophores in the sample activated by the first range of wavelengths.

Figure 3B:
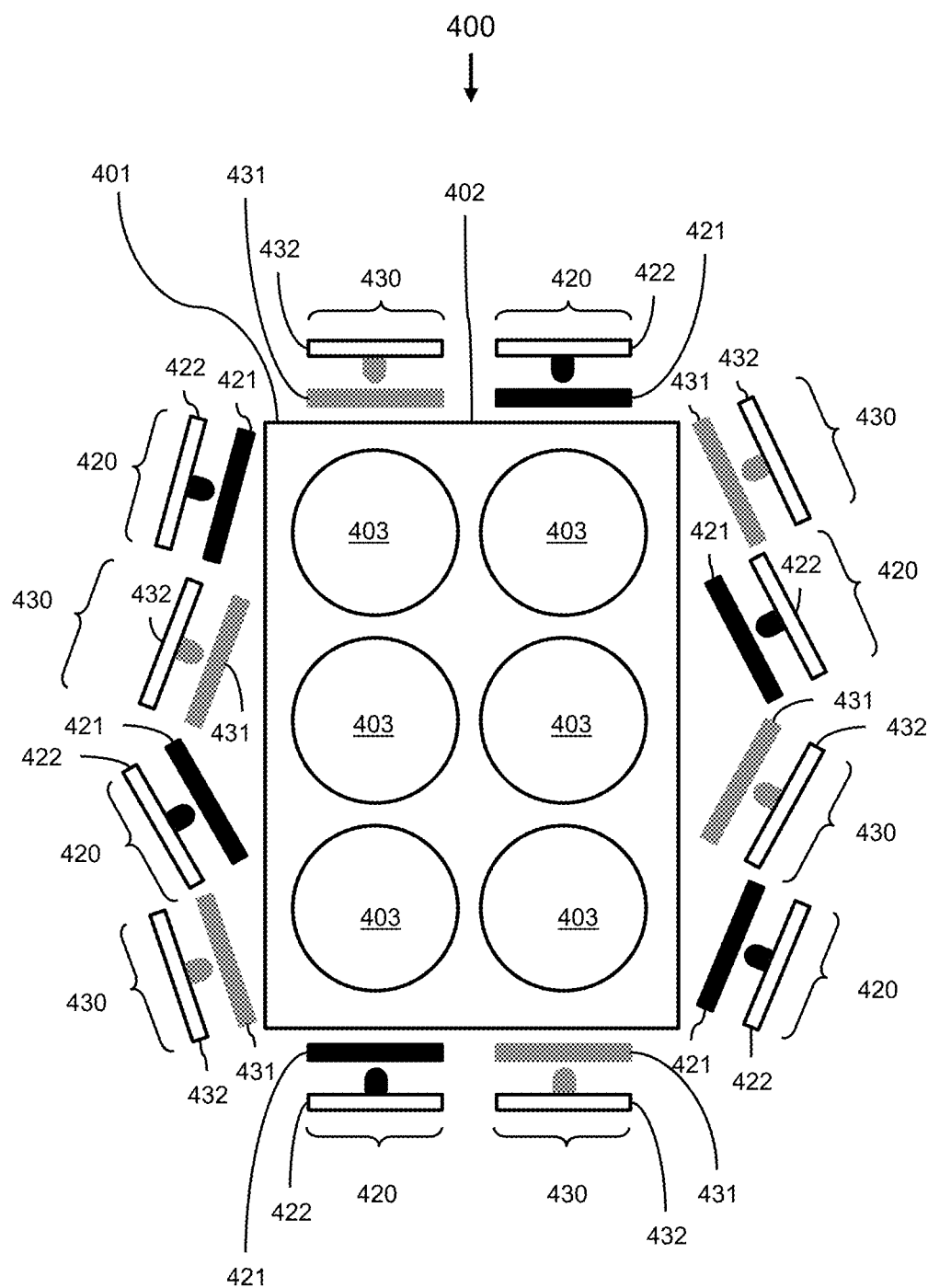
FIG. 3B is a schematic drawing of a plan view of components an MWB system configured for dual band fluorescence imaging, according to an embodiment.

FIG. 3B is a schematic drawing of a plan view of components an MWB system 400, according to a dual band embodiment. The illustrated MWB system 400 comprises six (6) of the same imaging devices arranged within a body 401 to be able to image samples in all six wells 403 in the 6-well plate 402 loaded on top of the body 401. Each of the imaging devices includes a first high power fluorescence illumination source 420 for providing excitation light of a first range of wavelengths and a second high power fluorescence illumination source 430 for providing excitation light of a second range of wavelengths. The high power fluorescence illumination sources 420 and high power fluorescence illumination sources 430 are installed to provide the excitation light from the side of the 6-well plate 402 proximal the well 403 with the sample being imaged. The high power fluorescence illumination source 420 and high power fluorescence illumination source 430 are oriented to direct excitation light to the center of the well 403. Each first high power fluorescence illumination source 420 includes a high-power light source (e.g. LED) 421 and a first excitation filter 422. Each second high power fluorescence illumination source 430 includes a high-power light source (e.g. LED) 431 and a second excitation filter 432. The first excitation filter 422 passes excitation light of the first range of wavelengths and blocks other wavelengths. The second excitation filter 432 passes excitation light of the second range of wavelengths and blocks other wavelengths. In this example, the imaging devices of the MWB system 400 has a dual band emission filter (not shown) between the objectives. The dual band emission filter (not shown) between the objectives blocks excitation light of a first range of wavelengths and a second range of wavelengths. During the fluorescence imaging method, the high-power light sources (e.g. LEDs) 421 of the MWB system 400 are turned on and the image sensor of each imaging device acquires a first monochromic fluorescence image of the sample in the corresponding well. The first fluorescence image based on emissions from fluorophores in the sample activated by the first range of wavelengths. At another time during the fluorescence imaging process, the high-power light sources (e.g. LEDs) 431 of the MWB system 400 are turned on and the image sensor of each imaging device acquires a second monochromic fluorescence image of the sample in the corresponding well. The second fluorescence image is based on emissions from fluorophores in the sample activated by the second range of wavelengths. The MWB system 400 use a processor to convert the first and second monochromic fluorescence images into first and second color fluorescence images and overlay the data from the first and second fluorescence images to generate a dual-color fluorescence image.

Figure 4A:
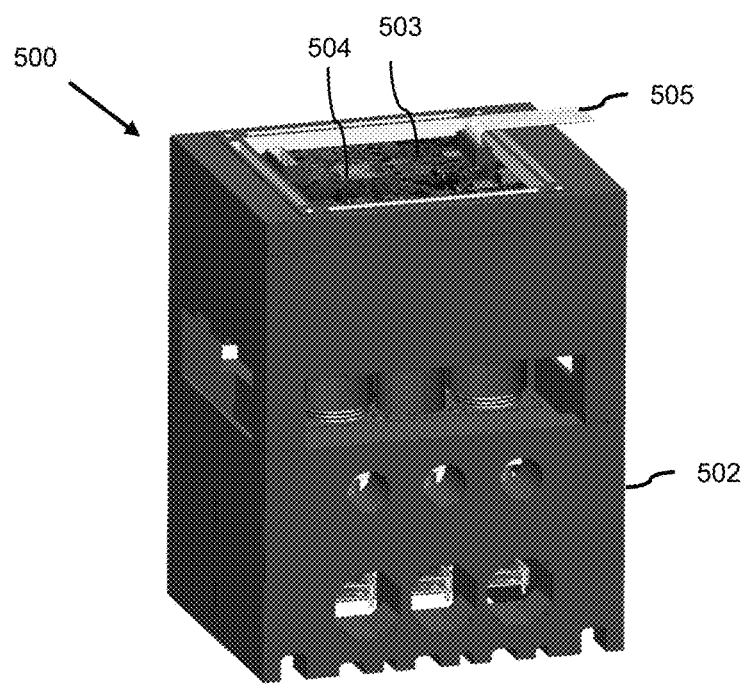
FIG. 4A is a schematic drawing of an MWB system configured for dual band fluorescence imaging, according to an embodiment.
Figure 4B:
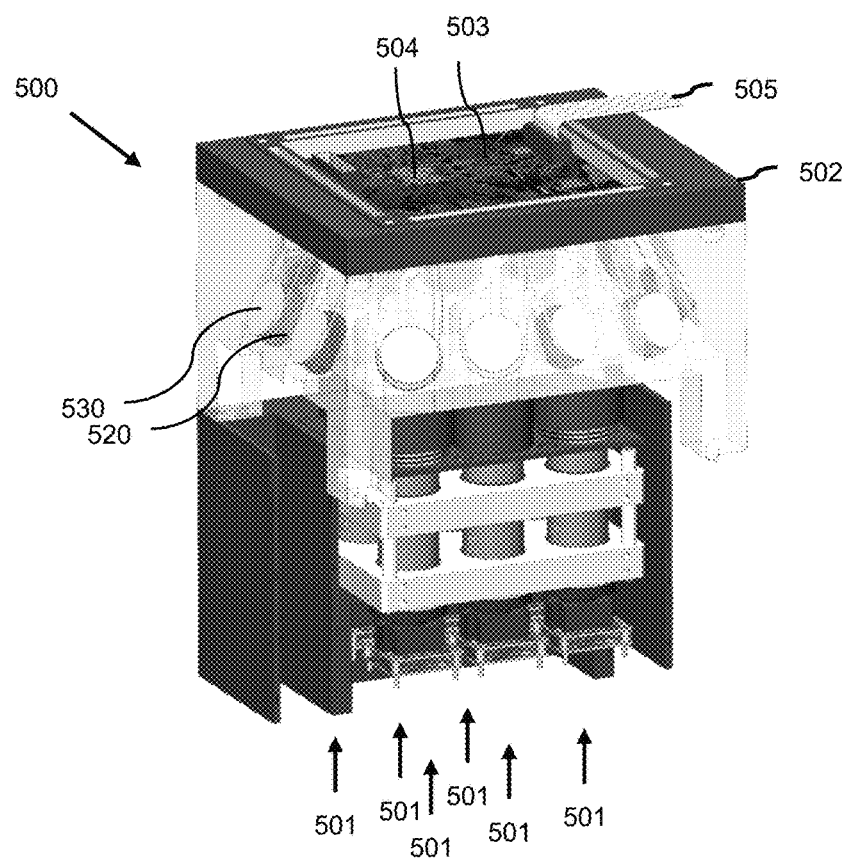
FIG. 4B is a schematic drawing of some the components of MWB system shown in FIG. 4A, according to an embodiment.

FIG. 4A is a schematic drawing of an MWB system 500, according to a dual band embodiment. Some of the components of the MWB system 500 are similar to those described with respect to FIG. 3B. The illustrated MWB system 500 is comprised of six (6) of the same imaging devices 501 arranged within a single body 502 to be able to image samples in all six wells in the 6-well plate. FIG. 4B is a schematic drawing of some of the components of MWB system 500 shown in FIG. 4A, according to an embodiment. In this drawing some of the components are illustrated as being transparent to view inner components. The MWB system 500 includes an electrical connection 505 in the form of a ribbon cable bewteen the variable illumiantion source and a processor.

Each of the imaging devices 501 includes a first high power fluorescence illumination source 520 for providing excitation light of a first range of wavelengths and a second high power fluorescence illumination source 530 for providing excitation light of a second range of wavelengths. The high power fluorescence illumination sources 520 and high power fluorescence illumination sources 530 are installed to provide the excitation light from the side of well with the sample being imaged. The high-power fluorescence illumination sources 520 and 530 are positioned at an angle from the plane at the bottom inner surface of the well. The angle is out of the numerical aperture (NA) of the first objective lens to prevent the acceptance of the powerful unscattered excitation light. The high power fluorescence illumination source 520 and high power fluorescence illumination source 530 are oriented to direct excitation light generally to the center of the well. Each high power fluorescence illumination source 520 includes one or more high-power light sources (e.g. LEDs) and a first excitation filter. Each high power fluorescence illumination source 530 includes one or more high-power light sources (e.g. LEDs) and an excitation filter. The first excitation filter passes excitation light of the first range of wavelengths and blocks other wavelengths. The second excitation filter passes excitation light of the second range of wavelengths and blocks other wavelengths. In this example, the imaging devices of the MWB system 500 has a dual band emission filter (not shown) between the objectives of each imaging device. The dual band emission filter (not shown) between the objectives blocks excitation light of a first range of wavelengths and a second range of wavelengths. During the fluorescence imaging method, the high-power light sources (e.g. LEDs) of the first high-power fluorescence illumination sources 520 are turned on and the image sensor can acquire a first fluorescence image of each sample in the six wells. The first fluorescence image based on emissions from fluorophores in the sample activated by the first range of wavelengths. At another time during the fluorescence imaging method, the high-power light sources (e.g. LEDs) of the second high-power fluorescence illumination sources 530 are turned on and the image sensor can acquire a second fluorescence image of each sample in the six wells. The second fluorescence image is based on emissions from fluorophores in the sample activated by the second range of wavelengths. The MWB system 500 can use a processor to convert the first and second monochromic fluorescence images into first and second color fluorescence images and overlay the data from the first and second color fluorescence images to generate a dual-color fluorescence image.

The MWB system 500 also includes a circuit board or other dielectric substrate 503 with a controller 504. The variable illumination source can be electrically and physically coupled onto or into the circuit board 503. Conductive leads of the variable illumination source can be electrically coupled with the controller 504 via conductive traces printed or otherwise deposited on a first or upper surface of the circuit board 503 while the light-emitting portions of the variable illumination source can be oriented so as to radiate light away from a second or lower surface of the circuit board 503 toward optical system. In the illustrated implementation, the controller 504 is mounted on the same circuit board 503 as the variable illumination source. In some other implementations, the controller 504 can be mounted onto a separate circuit board that is electrically coupled with the circuit board 503.

Figure 5:
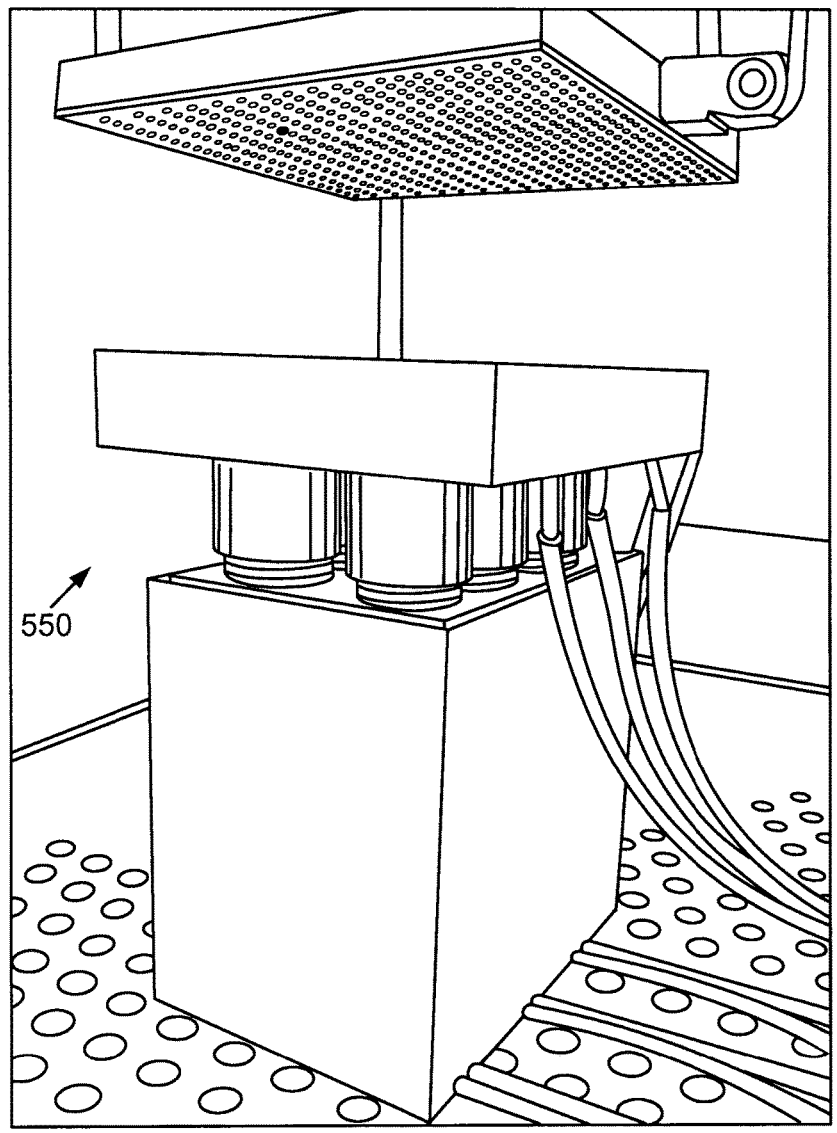
FIG. 5 is a photograph of an MWB system, according to an embodiment.

FIG. 5 is a photograph of an MWB system 550, according to an embodiment. The MWB system 550 is shown located in an incubator such as the incubator 12 shown in FIG. 1. The MWB system 600 has a body and a variable illumination source in the form of an LED matrix located at a distance above the 6-well plate. The MWB system 550 includes electrical connectors between the high-power LED module and a processor and/or a power supply. The size of the MWB system 550 is 125 mm (Wide)×133 mm (Long)× 170 mm (Height) including a 6-well plate and high-power LED module. In the illustrated example, the body was 3-D printed using a Makerbot 3D printer.

Certain components of the MWB systems are in electronic communication with other components and/or with one or more processors. The electronic communication between these various components may be in wired and/or wireless form. For example, FIG. 4A shows an electrical connection 505 in the form of a ribbon cable to the variable illumiantion source 110 of the MWB system 500.

According to certain aspects, an incubator system or an MWB system includes one or more processors and one or more computer readable medium (CRM). In some cases, a display is also included. For example, FIG. 2D shows an MWB system 100 having a processor 180, a computer readable medium (CRM) 184, and an optional (denoted by dotted line) display 182. The processor(s) is an electronic communication with the CRM(s) and optionally with the variable illumination source and/or the high power fluorescence illumination source(s) to send control signals. For example, control signals may be sent to the variable illumination source and the image sensor to synchronize the sequential illumination with the exposure (sampling) times of the image sensor.

The CRM(s) is in electronic communication with the processor to store and retrieve data. The optional display is an electronic communication with the processor receive display data for displaying images and other data. In one aspect, the processor, optional display and CRM are components of a computing device such as, for example, a smartphone, laptop, desktop, tablet, and the like. Although a single processor and single CRM are described with respect to illustrated examples, multiple processors and/or multiple CRM can be used.

The processor(s) (e.g., microprocessor) receives instructions stored on the CRM and executes those instructions to perform one or more functions of one or more MWB systems and/or an incubator sytem. Example processors include, for example, one or more of a general purpose processor (CPU), an application-specific integrated circuit (ASIC), an programmable logic device (PLD) such as a field-programmable gate array (FPGA), or a System-on-Chip (SoC) that includes one or more of a CPU, ASIC, PLD as well as a memory and various interfaces. The processor is configured to receive the image data from the image sensor. In one example, the processor executes instructions to perform operations of the FP reconstruction process and/or other operations of the FP imaging method. In another example, the processor executes instructions stored on the CRM to send control signals to the variable illumination source to sequentially illuminating discrete light elements for sequential illumination and/or executes instructions stored on the CRM to send control signals to the image sensor to measure intensity over an exposure duration to acquire raw intensity measurements (images). In another example, the processor executes instructions stored on the CRM to perform one or more other functions of the system such as, for example, 1) interpreting image data from the sequence of acquired intensity images, 2) reconstructing a higher resolution image from the data from the sequence of acquired intensity images, 3) generating a fluorescence image, 4) generating a dual band fluorescence image by overlaying a first fluorescence image associated with a first range of wavelengths with a second fluorescence associated with a second range of wavelengths and/or 5) displaying one or more images or other output on a display.

In one aspect, the processor(s) is part of a controller that sends signals with control instructions to component(s) of one or more MWB systems to perform one or more functions of the system(s). In one case, the controller can also control power component(s) of one or more MWB systems. In one example, a controller controls the operations of the variable illumination source, fluorescence illumination sources, and/or image sensors. In one case, the controller controls the sequential illumination of light sources in the variable illumination source, for example, by selectively powering on or otherwise allowing only particular ones or subsets of the light sources to form various illumination patterns at particular times and for particular durations during various image acquisitions. The controller also is in communication with at least one internal memory device. The internal memory device can include a non-volatile memory array for storing processor-executable code (or "instructions") that is retrieved by the processor to perform various functions or operations described herein for carrying out various operations on the image data or other functions of the MWB systems. The internal memory device also can store raw and/or processed image data (including FP-reconstructed images and raw intensity images). In some implementations, the internal memory device or a separate memory device can additionally or alternatively include a volatile memory array for temporarily storing instructions to be executed as well as image data to be processed, stored, or displayed. In some implementations, the controller itself can include volatile and in some instances also non-volatile memory.

The MWB system generally implements one or more processors configured to receive image data from the image sensor(s). In some implementations, the processor executes instructions stored on the CRM to perform one or more processing operations such as FP imaging processes to generate high resolution images, refocus images, and/or for aberration correction. In some implementations, the one or more processors are configured or configurable by a user to output raw image data or processed image over a communication interface (e.g., ribbon cable 505 in FIGS. 4A and 4B) to an external computing device or system 118. Indeed in some implementations, one or more of the operations of the MWB system can be performed by such an external computing device. In some implementations, the processor(s) also can be configured or configurable by a user to output raw image data as well as processed image data over a communication interface for storage in an external memory device or system. The network communication interface also can be used to receive information such as software or firmware updates or other data for download. In some implementations, a MWB system further includes one or more other interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that one or more of the components of teh MWB system can be electrically coupled to communicate with the controller over one or more of a variety of suitable interfaces and cables such as, for example, USB interfaces and cables, ribbon cables, Ethernet cables, among other suitable interfaces and cables.

The data signals output by the image sensors may be, in some implementations, mutliplexed, serialized or otherwise combined by a multiplexer, serializer or other electrical component of the image sensors before being communicated to the processor(s). In such implementations, the processor(s) can further include a demultiplexer, deserializer or other device or component for separating the image data from each of the image sensors so that the image frames (intensity distribution measurements) for each of the sample wells can be processed in parallel.

The CRM(s) (e.g., memory) can store instructions for performing certain functions of one or more MWB systems and/or an incubator sytem. These instructions are executable by a processor. The CRM can also store sequences of (lower resolution) intensity measurements, fluorescence images, and other data associated with the imaging method.

The optional display is in electronic communication with the processor to receive display data for displaying on the display to, for example, an operator of the incubator system. Typically the display is a color display.

Although MWB systems are described in many examples as being implemented in an incubator, MWB systems can be implemented in other environments as well. In one aspect, an MWB system can be implemented in a clean room. In another aspect, an MWB system can be implemented in a manufacturing setting.

III. Imaging Methods for Fourier Ptychographic (FP) Bright-Field Imaging and Fluorescence Imaging The MWB system implements an imaging method that can both use FP techniques to generate an improved resolution bright-field image of each of the samples in a multi-well plate (FP imaging process) and generate a fluorescence image of each sample (fluorescence imaging process).

The FP imaging process typically comprises a raw image acquisition (data collection) process and an FP reconstruction process. During the FP image acquisition process, the image sensor acquires n uniquely illuminated intensity bright field images while the variable illumination source provides plane wave illumination from n different illumination angles. At each image acquisition (sample) time, the image sensor acquires a uniquely illuminated intensity image associated with a single illumination angle. During the FP image acquisition process, each light element (e.g., one or more LEDs) in an illumination sequence will turn on and the image sensor will record an intensity distribution from light passing through the sample to acquire and save a sequence of intensity images associated with the n different illumination angles (i.e., uniquely illuminated intensity images). The low resolution images are combined using a FP reconstruction process to generate a high resolution complex image of the sample. Details of an example of an FP reconstruction process are described in G. Zheng, R, Iorsimeyer, and C. Yang, "Wide-field, high-resolution Fourier ptychographic microscopy," *Nature Photonics* (2013), which is hereby incorporated by reference in its entirety.

During the image acquisition process, the sample is illuminated by a sequence of n illumination angles using a variable illumination source. During the image acquisition process, the optical system filters lights passing through a sample from the variable illumination source and acquires n uniquely illuminated intensity images. During the FP reconstruction process, the n intensity images are iteratively combined in the Fourier domain to generate higher-resolution image data. At each iteration, a filter is applied in the Fourier domain for a particular plane wave incidence angle, an inverse Fourier transform is applied to generate a lower resolution image, the intensity of the lower resolution image is replaced with an intensity measurement, a Fourier transform is applied, and the corresponding region in Fourier space is updated.

The reconstruction process includes a phase retrieval technique that uses angular diversity to recover complex sample images. The recovery process alternates enforcement of known image data acquired in the spatial domain and a fixed constraint in the Fourier domain. This phase retrieval recovery can be implemented using, for example, an alternating projections procedure, a convex reformulation of the problem, or any non-convex variant in-between. Instead of needing to translate a sample laterally by mechanical means, the reconstruction process varies the spectrum constraint in the Fourier domain to expand the Fourier passband beyond that of a single captured image to recover a higher-resolution sample image.

In one aspect, the FP imaging process includes an aberration correction process such as re-focusing (propagating) process. A refocusing process may be useful where the sample was placed at a sample plane at $z=z_0$ where the in-focus plane of the optical element is located at position $z=0$. In other words, the image captured of the sample is not the image at the sample plane, but is the sample profile propagated by a distance of $-z_0$ from the in-focus plane of the optical element. In these cases, the FP imaging process re-focuses the sample by propagating the image data by the $z_0$ distance back to the sample plane, without having to mechanically move the sample in the z-direction. The re-focusing (propagating) step(s) can be performed by multiplying a phase factor in Fourier space.

In one multiplexing embodiment, multiple light elements (LEDs) can be turned on at the same time in a unique pattern during the capture of each raw image (measurement of intensity distribution over an exposure duration). Using a multiplexing process, intensity data associated with each illumination angle can be separated from the raw image captured. An example of a multiplexing process can be found in U.S. patent application Ser. No. 14/960,252 titled "MULTIPLEXED FOURIER PTYCHOGRAPHY IMAGING SYSTEMS AND METHODS" filed on Dec. 4, 2015, which is hereby incorporated by reference in its entirety.

The fluorescence imaging process comprises generating a fluorescence image for each fluorescence illumination at a unique range of wavelengths. During the fluorescence imaging process, a high power fluorescence illumination source is turned on and a monochromic fluorescence image is acquired by the image sensor. A processor can generate a color fluorescence image using the image data from the monochromic fluorescence image. In a multi-band, multi-channel embodiment, each of the high power fluorescence illumination sources is turned on separately and a separate monochromic fluorescent image is acquired for each fluorescence illumination. In this case, the fluorescence imaging process further includes implementing instructions to overlap the multiple color fluorescence images to generate a single multicolor fluorescence image.

The Fourier ptychographic reconstruction process requires accurate illumination direction information associated with FP sequential illumination of the variable illumination source in order to stitch together the raw intensity images into the correct locations in the spatial frequency domain. Because the body of the MWB system is separate from the variable illumination source, there needs to be a calibration process to calibrate the light element positions relative to the image sensor for accurate FP reconstruction. This calibration process is needed when the MWB system is positioned or re-repositioned with respect to the image sensor such as, for example, when the MWB system is installed in an incubator having an LED matrix installed in a horizontal shelf above the MWB system.

Figure 6:
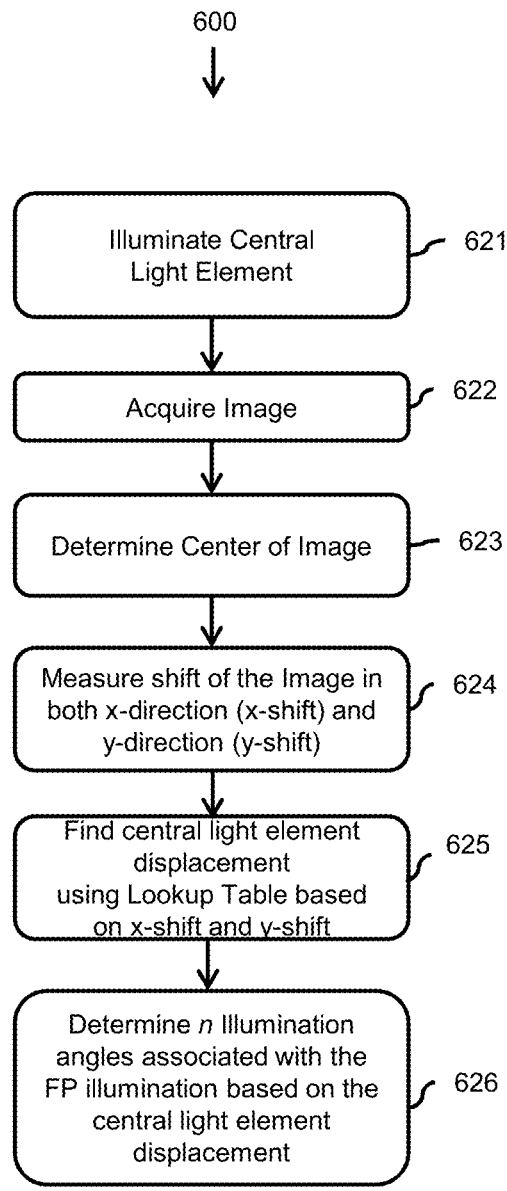
FIG. 6 is a flowchart of a calibration process for calibrating the positions of the discrete light elements (LEDs) of the variable illumination source relative to the image sensors, according to embodiments.

FIG. 6 is a flowchart 600 depicting operations of a calibration process for calibrating the positions of the discrete light elements (LEDs) of the variable illumination source relative to each of the image sensors, according to embodiments. This calibration process is used when the MWB system is positioned or repositioned relative to the variable illumination source.

At operation 621, a central light element (e.g. LED) of the variable illumination source is illuminated. For example, if a variable illumination source is shared among multiple MWB systems, light elements within an area of the variable illumination source provide FP illumination to a particular MWB system. In this case, the central light element of the area used to provide FP illumination is illuminated. If a single variable illumination source is used to provide FP illumination for the MWB system, the central light element of the variable illumination source is illuminated. A central light element is the LED which located most closely to the center of the objective lens. In this case, illuminate one LED which makes brightest image from the image sensor. There is only one LED position which makes brightest image. That LED is the central light element for the image sensor. The operations are carried out for each image sensor.

In one embodiment, the calibration process determines the central light element by turning on light elements sequentially and capturing an image for each light element illumination. The highest intensity image is determined from the multiple images captured. The central light element is determined based on the highest intensity image captured during the illumination by the multiple light elements.

At operation 622, the image sensor captures a vignette monochromic image during illumination by the central light element (e.g., LED). The image is converted to black and white. If there is a misalignment between the light element and the image sensor, the center of the image is shifted from the center of the image sensor. At operation 623, the center of the image is determined. At operation 624, the shift of the center of the image is measured in the x-direction (x-shift) and the y-direction (y-shift). At operation 625, the displacement of the central light element is determined based on the x-shift and y-shift of the image using a lookup table/plot. The lookup table/plot provides different displacements of the central light element associated with different values of x-shift and y-shift. Once the displacement of the central light element is determined from the lookup table/plot, the illumination angles associated with the light elements in the variable illumination source can be determined based on the geometry of the variable illumination source. At operation 626, the n illumination angles associated with the FP illumination is determined using the displacement of the central light element.

Figure 7A:
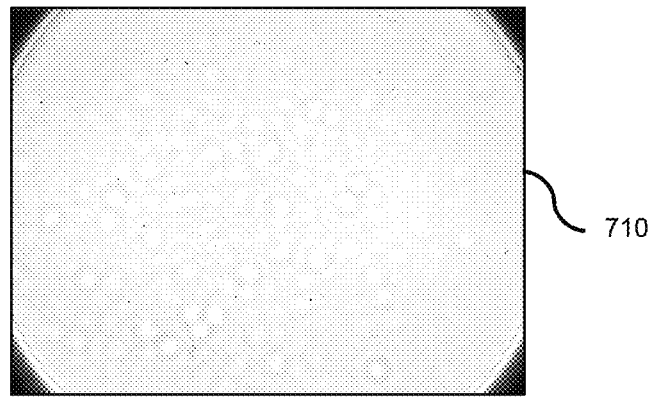
FIG. 7A is a monochrome vignette image captured during illumination by a central LED of an LED matrix, according to an embodiment.
Figure 7B:
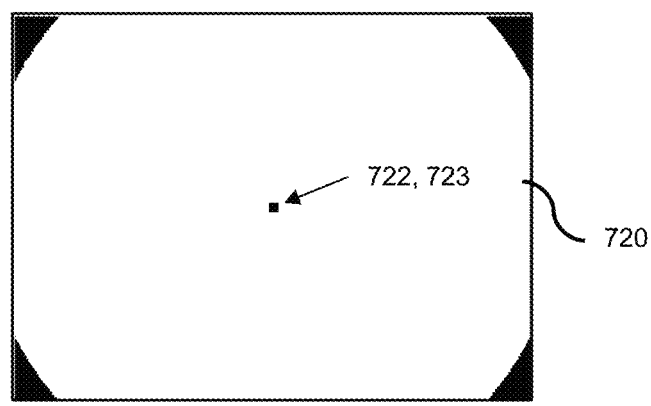
FIG. 7B is a converted black and white image of the image of FIG. 7A.
Figure 7C:
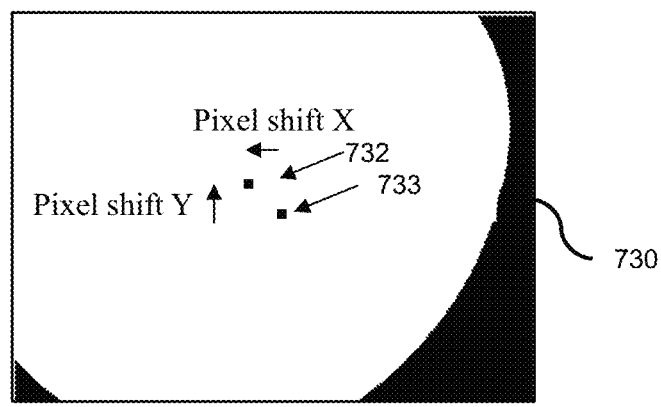
FIG. 7C is an image captured during illumination by a center LED of an LED matrix, according to another embodiment.
Figure 7D:
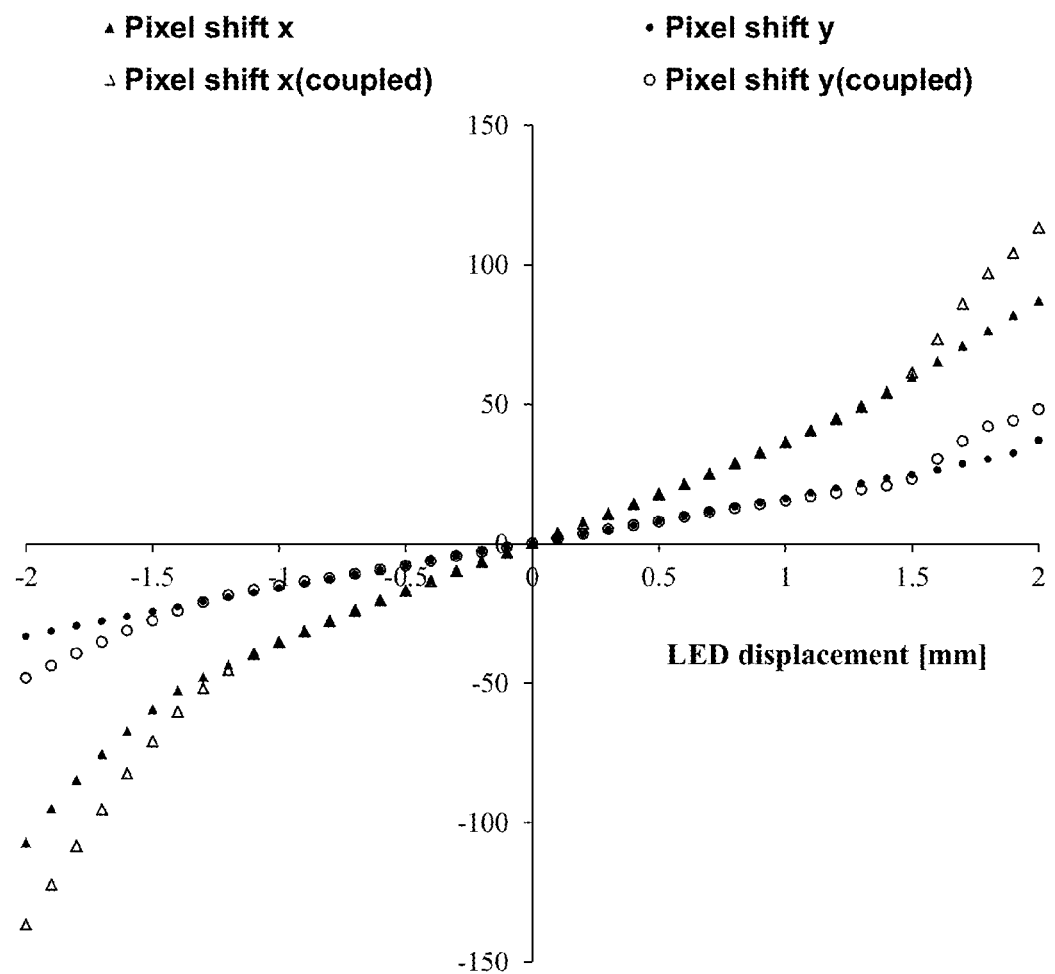
FIG. 7D is a lookup plot of LED displacement associated with x-shift and y-shift of the center of the image with respect to the center of the image sensor, according to an embodiment.

FIG. 7A is a monochrome vignette image captured during illumination by a central LED of an LED matrix, according to an embodiment. FIG. 7B is a converted black and white version of the image of FIG. 7A. In this example, the center 722 of the black and white image is located at the same location as the center 723 of the image sensor and the LED position is well aligned with the imaging sensor of the CMOS camera. FIG. 7C is an image captured during illumination by a center LED of an LED matrix, according to another embodiment. In this case, there is a misalignment between the central LED and the image sensor. As shown, there is a shift between the center 732 of the image and the center 723 of the image sensor. In this case, there is a shift in the x direction (pixel shift X) and a shift in the y direction (pixel shift Y). FIG. 7D is a lookup plot of LED displacement associated with x-shift and y-shift of the center 732 of the image with respect to the center 723 of the image sensor, according to an embodiment. In this example, the lookup table was made by moving the LED matrix relative to the image sensor by known amounts and determining different shifts of the center of the image associated with the LED displacement.

Figure 8:
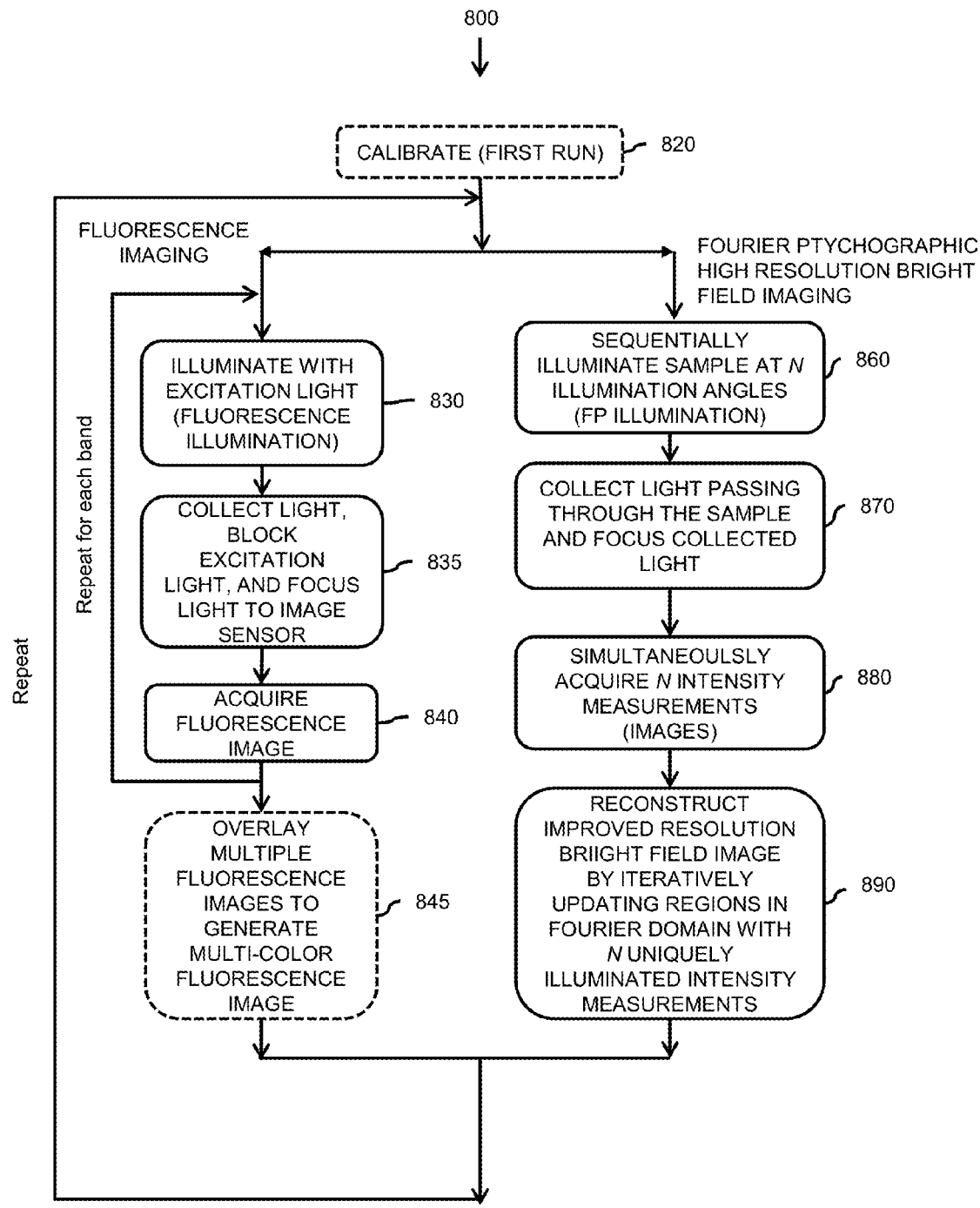
FIG. 8 is a flowchart depicting operations of an imaging method implemented by each of one or more imaging devices of an MWB system, according to embodiments.

FIG. 8 is a flowchart 800 depicting operations of an imaging method implemented by each of one or more imaging devices of an MWB system, according to embodiments. Multiple imaging devices of the MWB system can perform the imaging method in parallel. In one aspect, the imaging method begins its first imaging run with an optional operation (denoted by the dotted line) of calibrating the positions of the variable illumination source with the image sensors of the MWB system. An example of a calibration process is described respect to the flowchart 600 in FIG. 6. The imaging method performs a fluorescence imaging process and/or a FP high resolution bright field imaging process. The imaging method is repeated, for example, on a periodic basis. In one aspect, each run of an imaging method includes a fluorescence imaging process and a FP high resolution bright field imaging process.

If a fluorescence imaging process is performed, the imaging method proceeds to operation 830. At operation 830, a first high power fluorescence illumination source provides excitation light of a first range of wavelengths. The first high power fluorescence illumination source includes a high power light source (e.g. high-power LEDs) and excitation filter for passing excitation light of the first range of wavelengths and blocking other wavelengths. The excitation light of the first range of wavelengths is directed to the center of the sample. Fluorophore in the sample are activated by the excitation light and emit light (emissions) of another range of wavelengths (e.g., blue, green or red light). Since the excitation light is stronger than the emissions, the first high power fluorescence illumination source is facing directly toward the first collection objective of the optical system of the MWB system.

At operation 835, the first collection objective receives light issuing from the sample. An emission filter between the first collection objective and the second focusing objective blocks out any excitation light of the first range of wavelengths and passes the emissions to the second collection objective. The second collection objective receives the emissions and focuses to the image sensor of the MWB system. At operation 840, the image sensor receives the emissions from the second collection objective during fluorescence illumination by the first high power fluorescence illumination source and acquires a monochromic fluorescence intensity image. The image data of the monochromic fluorescence image can be converted into a color fluorescence image.

For multi-band, multichannel embodiments, operations 830, 835 and 840 are repeated for each band. For a dual band embodiment, for example, a second high power fluorescence illumination source provides excitation light of a second range of wavelengths (operation 830). The second high power fluorescence illumination source includes a high power light source (e.g. high-power LEDs) and excitation filter for passing excitation light of the second range of wavelengths and blocking other wavelengths. The first collection objective receives light issuing from the sample (operation 835). In the dual band embodiment, the emission filter is a dual band filter that blocks out excitation light of the first range of wavelengths and the second range of wavelengths. In this case, the dual band emission filter blocks out excitation light of the second range of wavelengths and passes emissions to the second collection objective. The second collection objective receives the emissions and focuses to the image sensor of the MWB system. The image sensor receives the emissions from the second collection objective during fluorescence illumination by the second high power fluorescence illumination source and acquires a second monochromic fluorescence intensity image (operation 840).

The imaging method performs optional (denoted by dotted line) operation 845 for multi-band, multichannel embodiments. In multi-band, multichannel embodiments, multiple color fluorescence images can are overlaid to generate a multi-color fluorescence image. In one aspect, after operation 845, the imaging method may further comprise sending a signal with display data from the processor to a display to display the color fluorescence image or other data on the display before repeating. After operation 845, the imaging method repeats to perform a fluorescence imaging process or a FP high resolution bright field imaging process.

If the FP imaging process is performed, the imaging method proceeds to operation 860. The FP imaging process generally comprises an image acquisition process (operations 660, 670, and 680) and a FP reconstruction process (step 690).

At operation 860, a variable illumination source sequentially illuminates the sample with plane wave illumination at n illumination angles. In one aspect, the variable illumination source provides sequential illumination based on illumination instructions that define the order of illuminated light elements (LEDs).

At operation 870, the optical system collects light issuing from the sample and propagates it to the image sensor. The first objective of the optical system collects light passing through the sample from the variable illumination source. In some cases, the illumination from the variable illumination source is of a range of wavelengths that will be passed by the emission filter between the first objective and the second objective. In these cases, the emission filter does not need to be removed during the FP imaging process. The second objective receives light emission filter and focuses it to the image sensor. The first objective of the optical system receives light passing through the sample from the variable illumination source during FP illumination. The first objective accepts (filters) light at a range of angles with its numerical aperture. In Fourier space, the filtering function of a first objective is represented by a circular pupil with radius of $NA \times k_0$, where $k_0 = 2\pi/\lambda$ is the wave number in vacuum. The FP imaging process updates in Fourier space circular regions defined by this filtering function of the first objective and the n illumination angles.

At operation 880, the image sensor receives light propagated by the optical system. During FP sequential illumination by n illumination angles, the image sensor acquires n uniquely illuminated intensity measurements (images) associated with different illumination angles. The image sensor measures an intensity distribution during an exposure time to acquire an intensity measurement (image). A process of the MWB system receives signal(s) with the data from the n uniquely illuminated intensity measurements (images).

At operation 890, a processor of the MWB system using the imaging method to reconstruct an improved resolution image by iteratively updating regions in Fourier space with the n uniquely illuminated intensity measurements (images). The processor reconstructs the improved resolution image using an FP reconstruction process. Two examples of FP reconstruction processes are discussed in detail with respect to respect to FIG. 9 and FIG. 10. In one aspect, after operation 890, the imaging method may further comprise sending image data from the processor to a display to display the high resolution bright field image or other data on the display before repeating. After operation 890, the imaging method repeats to perform a fluorescence imaging process or a FP high resolution bright field imaging process.

In one aspect, the processor generates a combined fluorescence and high resolution bright-field image of the sample by overlaying a fluorescence image generated by the fluorescence imaging process and a high resolution brightfield image generated by the FP imaging process. In another aspect, the processor generates a combined fluorescence and low resolution bright-field image of the sample by overlaying a fluorescence image generated by the fluorescence imaging process and a low resolution bright-field image captured during the acquisition process of the FP imaging process. In another aspect, the processor generates a high resolution phase image of the sample based on phase data in the FP imaging process.

In one aspect, the MWB system can implement the imaging method for time-lapse imaging or other long term imaging. For example, the imaging method can repeat each run at intervals such as, for example, one hour intervals, two hour intervals, one day intervals, etc. The imaging method can continue repeating each imaging run at intervals for a set period of time (e.g., one week, two weeks, one month, two months, etc.) or can run until an operator stops the imaging method. While this long term imaging continues, the MWB system can be located within an incubator.

FP Reconstruction Process

Certain details of the FP reconstruction process can be found in Zheng, Guoan, Horstmeyer, Roarke, and Yang, Changhuei, "Wide-field, high-resolution Fourier ptychographic microscopy," Nature Photonics vol. 7, pp. 739-745 (2013) and in U.S. patent application Ser. No. 14/065,280, titled "Fourier Ptychographic Imaging Systems, Devices, and Methods" and filed on Oct. 28, 2013. During the FP reconstruction process, overlapping regions in the Fourier domain are iteratively updated with lower resolution intensity image data to generate an improved resolution image.

Figure 9:
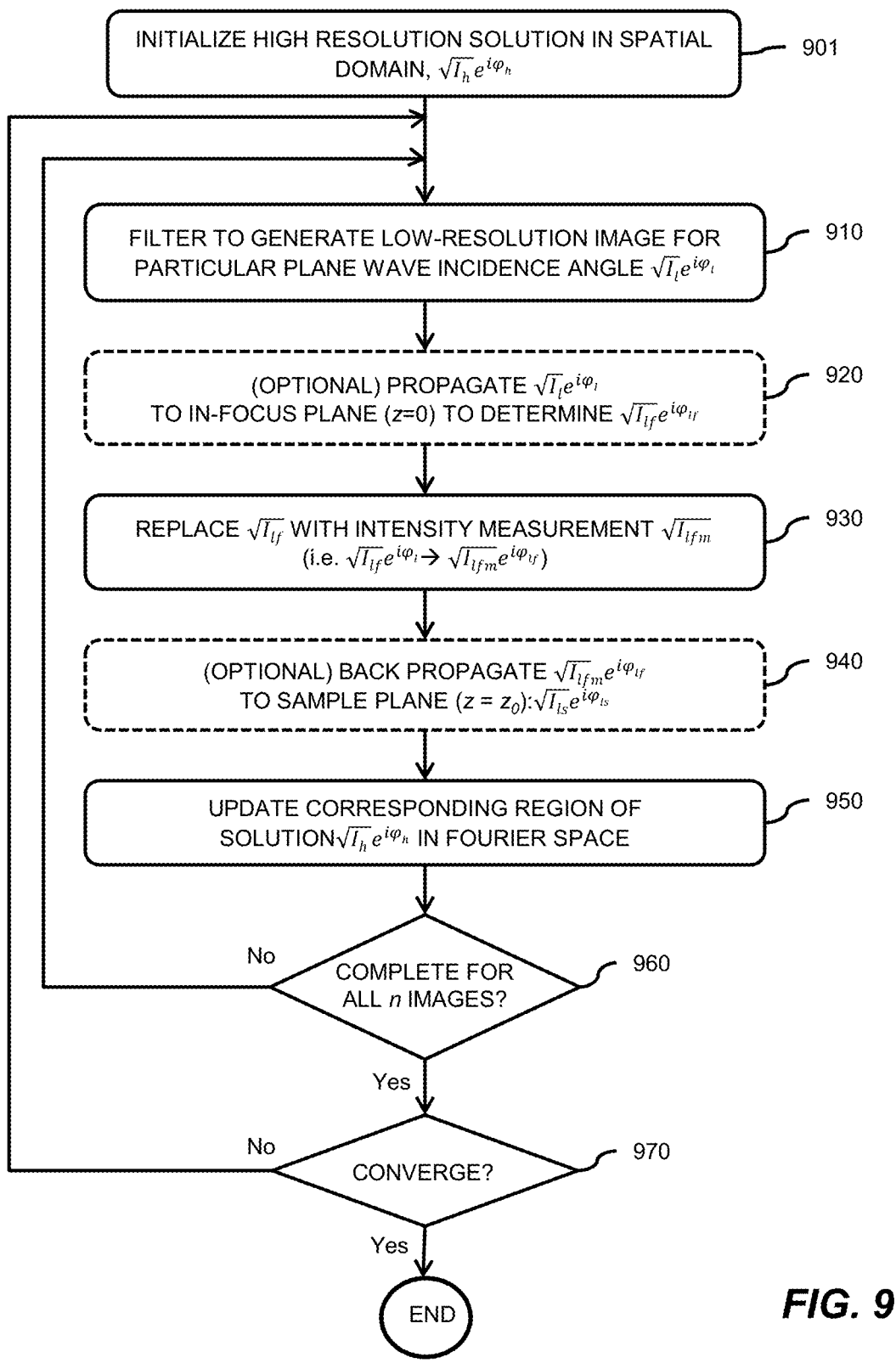
FIG. 9 is a flowchart of a FP reconstruction process, according to an embodiment.

FIG. 9 is a flowchart of a FP reconstruction process, according to an embodiment. Using this FP reconstruction process, an improved resolution image of the sample is reconstructed from n low-resolution intensity distribution measurements, $I_{lm}$ ($k^i_x$, $k^i_y$) (indexed by their illumination wavevector, $k_x^i$, $k_y^i$, with i=1, 2 . . . n) such as the n raw intensity images acquired during operations 860, 870, and 880 of FIG. 8.

At 901, a high-resolution image: $\sqrt{I_h}e^{i\varphi_h}$ is initialized in the spatial domain, and a Fourier transform is applied to the initial value to obtain an initialized Fourier transformed image $\tilde{I}_h$ using a processor of the MWB system. The initialized high-resolution solution may be an initial guess. This initial guess may be determined based on the assumption that the sample is located at the out-of-focus plane z=$z_0$. In some cases, the initial guess may be determined as a random complex matrix (for both intensity and phase). In other cases, the initial guess may be determined as an interpolation of the low-resolution intensity measurement with a random phase. An example of an initial guess is φ=0 and $I_h$ interpolated from any low-resolution image of the sample area. Another example of an initial guess is a constant value. The Fourier transform of the initial guess can be a broad spectrum in the Fourier domain.

In the iterative operations of 910, 920, 930, 940, 950, 960, and 970, the high-resolution image of the sample is reconstructed by iteratively combining low-resolution intensity measurements in Fourier space using the processor of the MWB system. Optional operations 920 and 940 may be performed if the sample is out-of-focus by the amount of $z_0$.

At 910, the processor performs low-pass filtering of the high-resolution image $\sqrt{I_h}e^{i\varphi_h}$ in the Fourier domain to generate a low-resolution image $\sqrt{I_l}e^{i\varphi_l}$ for a particular plane wave incidence angle ($\theta_x^i$, $\theta_y^i$) with a wave vector ($k_x^i$, $k_y^i$). The Fourier transform of the high-resolution image is $\tilde{I}_h$ and the Fourier transform of the low-resolution image for a particular plane wave incidence angle is h. In the Fourier domain, the reconstruction process filters a low-pass region from the spectrum $\tilde{I}_h$ of the high-resolution image $\sqrt{I_h}e^{i\varphi_h}$. The low-pass region is a circular aperture with a radius of NA*$k_0$, where $k_0$ equals $2\pi/\lambda$ (the wave number in vacuum), given by the coherent transfer function of the first objective lens of the MWB system. In Fourier space, the location of the region corresponds to the illumination angle during the current iteration. For an oblique plane wave incidence with a wave vector ($k_x^i$, $k_y^i$), the region is centered about a position ($-k_x^i$, $-k_y^i$) in the Fourier domain of $\sqrt{I_h}e^{i\varphi_h}$.

At optional operation 920, using the processor, the low-resolution image, $\sqrt{I_l}e^{i\varphi_l}$ is propagated in the Fourier domain to the in-focus plane at z=0 to determine the low-resolution image at the focused position: $\sqrt{I_{lf}}e^{i\varphi_{lf}}$. In one embodiment, operation 920 is performed by Fourier transforming the low-resolution image $\sqrt{I_l}e^{i\varphi_l}$, multiplying by a phase factor in the Fourier domain, and inverse Fourier transforming to obtain $\sqrt{I_{lf}}e^{i\varphi_{lf}}$. In another embodiment, operation 920 is performed by the mathematically equivalent operation of convolving the low-resolution image $\sqrt{I_l}e^{i\varphi_l}$ with the point-spread-function for the defocus. In another embodiment, operation 920 is performed as an optional sub-operation of operation 910 by multiplying $\tilde{I}_l$ by a phase factor in the Fourier domain before performing the inverse Fourier transform to produce $\sqrt{I_{lf}}e^{i\varphi_{lf}}$. Optional operation 920 need not be included if the sample is located at the in-focus plane (z=0).

At operation 930, using the processor, the computed amplitude component $\sqrt{I_{lf}}$ of the low-resolution image at the in-focus plane, $\sqrt{I_{lf}}e^{i\varphi_{lf}}$, is replaced with the square root of the low-resolution intensity measurement measured $\sqrt{I_{lfm}}$ by the light detector of the MWB system. This forms an updated low resolution target: $\sqrt{I_{lfm}}e^{i\varphi_{lf}}$.

At optional operation 940, using the processor, the updated low-resolution image $\sqrt{I_{lfm}}e^{i\varphi_{lf}}$ may be back-propagated to the sample plane (z=$z_0$) to determine $\sqrt{I_{ls}}e^{i\varphi_{ls}}$. Optional operation 940 need not be included if the sample is located at the in-focus plane, that is, where $z_0$=0. In one embodiment, operation 940 is performed by taking the Fourier transform of the updated low-resolution image $\sqrt{I_{lfm}}e^{i\varphi_{lf}}$ and multiplying in the Fourier space by a phase factor, and then inverse Fourier transforming it. In another embodiment, operation 940 is performed by convolving the updated low-resolution image $\sqrt{I_{lfm}}e^{i\varphi_{lf}}$ with the point-spread-function of the defocus. In another embodiment, operation 940 is performed as a sub-operation of operation 950 by multiplying by a phase factor after performing the Fourier transform onto the updated target image.

At operation 950, using the processor, a Fourier transform is applied to the updated target image propagated to the sample plane: $\sqrt{I_{ls}}e^{i\varphi_{ls}}$, and this data is updated in the corresponding region of high-resolution solution $\sqrt{I_{h}}e^{i\varphi_{h}}$ in the Fourier space corresponding to the corresponding to the incidence wave vector ($k_x^i$, $k_x^i$).

At operation 960, the processor determines whether operations 1510 through 1560 have been completed for all n uniquely illuminated low resolution intensity images. If operations 1510 through 1560 have not been completed for all the images, operations 1510 through 1560 are repeated for the next image.

At operation 970, the processor determines whether the high-resolution solution has converged. In one example, the processor determines whether the high-resolution solution converged to a self-consistent solution. In one case, the processor compares the previous high-resolution solution of the previous iteration or initial guess to the present high-resolution solution, and if the difference is less than a certain value, the solution is determined to have converged to a self-consistent solution. If the processor determines that the solution has not converged at operation 970, then operations 910 through 960 are repeated. In one embodiment, operations 910 through 960 are repeated once. In other embodiments, operations 910 through 960 are repeated twice or more. If the solution has converged, the processor transforms the converged solution in Fourier space to the spatial domain to recover the improved resolution image $\sqrt{I_h}e^{i\varphi_h}$ and the FP reconstruction process ends.

Figure 10:
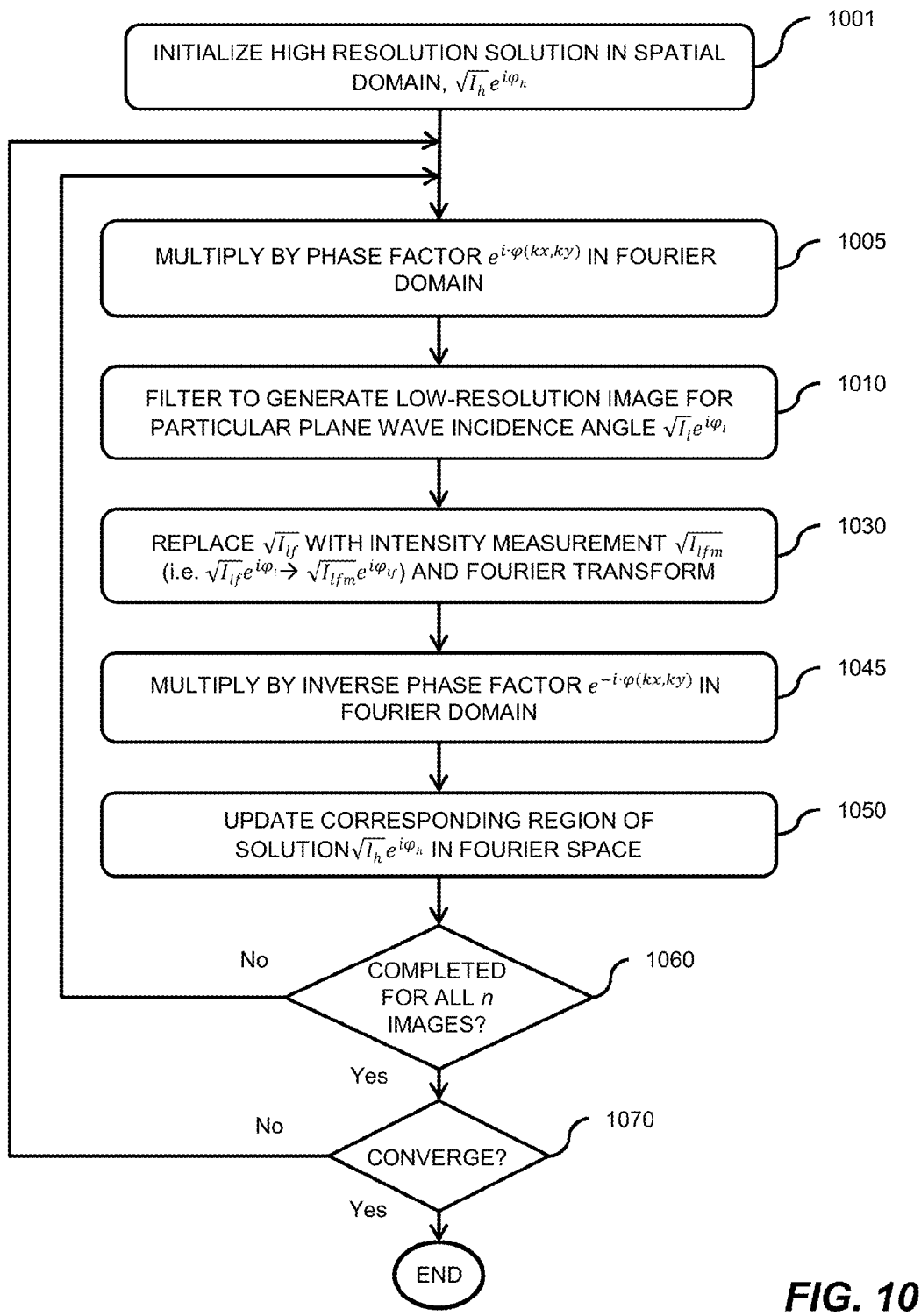
FIG. 10 is a flowchart of a FP reconstruction process, according to an embodiment.

FIG. 10 is a flowchart of a FP reconstruction process, according to an embodiment. Using this FP reconstruction process, an improved resolution image of the sample is reconstructed from n low-resolution intensity distribution measurements, $I_{lm}$ ($k_x^i$, $k_y^i$) (indexed by their illumination wavevector, $k_x^i$, $k_y^i$, with i=1, 2, . . . , n) such as the n raw intensity images acquired during operations 860, 870, and 880 of FIG. 8.

In this example, the FP reconstruction process includes digital wavefront correction. The FP reconstruction process incorporates digital wavefront compensation in the two multiplication operations 1005 and 1045. Specifically, operation 1005 models the connection between the actual sample profile and the captured intensity data (with includes aberrations) through multiplication with a pupil function: $e^{i\cdot\varphi(k_x,k_y)}$ by the processor. Operation 1045 inverts such a connection to achieve an aberration-free reconstructed image. Sample defocus is essentially equivalent to introducing a defocus phase factor to the pupil plane (i.e., a defocus aberration):

$$e^{i\cdot\varphi(k_x,k_y)} = e^{i\sqrt{(2\pi/\lambda)^2-k_x^2-k_y^2}\cdot z_0}, k_x^2+k_y^2 < (NA\cdot 2\pi/\lambda)^2 \quad \text{(Eqn. 1)}$$

where $k_x$ and $k_y$ are the wavenumbers at the pupil plane, $z_0$ is the defocus distance, and NA is the numerical aperture of the first objective.

At 1001, a high-resolution image: $\sqrt{I_h}e^{i\varphi_h}$ is initialized in the spatial domain, and a Fourier transform is applied to the initial value to obtain an initialized Fourier transformed image $\tilde{I}_h$. The initialized high-resolution solution may be an initial guess. In some aspects, the initial guess is determined based on the assumption that the sample is located at the out-of-focus plane $z=z_0$. In some cases, the initial guess is determined as a random complex matrix (for both intensity and phase). In other cases, the initial guess is determined as an interpolation of the low-resolution intensity measurement with a random phase. An example of an initial guess is $\varphi=0$ and $I_h$ interpolated from any low-resolution image of the sample area. Another example of an initial guess is a constant value. The Fourier transform of the initial guess can be a broad spectrum in the Fourier domain.

In the iterative operations of 1005, 1010, 1030, 1045, 1050, 1060, and 1070, the high-resolution image of the sample is computationally reconstructed by iteratively combining low-resolution intensity measurements in Fourier space using a processor of the MWB system.

At operation 1005, the processor multiplies by a phase factor $e^{i\cdot\varphi(k_x,k_y)}$ in Fourier domain.

At operation 1010, the processor performs low-pass filtering of the high-resolution image $\sqrt{I_h}e^{i\varphi_h}$ in the Fourier domain to generate a low-resolution image $\sqrt{I_l}e^{i\varphi_l}$ for a particular plane wave incidence angle ($\theta_x^i$, $\theta_y^i$) with a wave vector ($k_x^i$, $k_y^i$). The Fourier transform of the high-resolution image is $\tilde{I}_h$ and the Fourier transform of the low-resolution image for a particular plane wave incidence angle is $\tilde{I}_l$. In the Fourier domain, the process filters a low-pass region from the spectrum $\tilde{I}_h$ of the high-resolution image $\sqrt{I_h}e^{i\varphi_h}$. This region is a circular aperture with a radius of $NA*k_0$, where $k_0$ equals $2\pi/\lambda$ (the wave number in vacuum), given by the coherent transfer function of the first objective lens. In Fourier space, the location of the region corresponds to the incidence angle. For an oblique plane wave incidence with a wave vector ($k_x^i$, $k_y^i$), the region is centered about a position ($-k_x^i$, $-k_y^i$) in the Fourier domain of $\sqrt{I_h}e^{i\varphi_h}$.

At operation 1030, using the processor, the computed amplitude component $\sqrt{I_{lf}}$ of the low-resolution image at the in-focus plane, $\sqrt{I_{lf}}e^{i\varphi_{lf}}$, is replaced with the square root of the low-resolution intensity measurement measured by the light detector of the MWB system. This forms an updated low resolution target: $\sqrt{I_{lfm}}e^{i\varphi_{lf}}$.

At operation 1045, the processor multiplies by an inverse phase factor $e^{-i\cdot\varphi(k_x,k_y)}$ in Fourier domain.

At operation 1050, using the processor, a Fourier transform is applied to the updated target image propagated to the sample plane: $\sqrt{I_{ls}}e^{i\varphi_{ls}}$, and this data is updated in the corresponding region of high-resolution solution $\sqrt{I_h}e^{i\varphi_h}$ in the Fourier space corresponding to the corresponding to the incidence wave vector ($k_x^i$, $k_y^i$).

At operation 1060, the processor determines whether operations 1005 through 1050 have been completed for all n uniquely illuminated low resolution intensity images. If operations 1005 through 1050 have not been completed for all for all n uniquely illuminated low resolution intensity images, operations 1005 through 1050 are repeated for the next image.

At operation 1070, the processor determines whether the high-resolution solution has converged. In one example, the processor determines whether the high-resolution solution has converged to a self-consistent solution. In one case, the processor compares the previous high-resolution solution of the previous iteration or initial guess to the present high-resolution solution, and if the difference is less than a certain value, the solution has converged to a self-consistent solution. If processor determines that the solution has not converged, then operations 1005 through 1070 are repeated.

In one embodiment, operations 1005 through 1070 are repeated once. In other embodiments, operations 1005 through 1070 are repeated twice or more. If the solution has converged, the processor transforms the converged solution in Fourier space to the spatial domain to recover the high-resolution image $\sqrt{I_h}e^{i\varphi_h}$ and the FP reconstruction process ends.

In certain aspects, the neighboring regions in Fourier space, which are iteratively updated for each image, overlap each other. In the overlapping area between updated overlapping regions, the MWB system has multiple samplings over the same Fourier space. In one aspect, the overlapping area between neighboring regions has an area that is between 2% to 99.5% of the area of one of the neighboring regions. In another aspect, the overlapping area between neighboring regions has an area that is between 65% to 75% of the area of one of the neighboring regions. In another aspect, the overlapping area between neighboring regions has an area that is about 65% of the area of one of the neighboring regions.

IV. MWB System Demonstrations

Figure 11A:
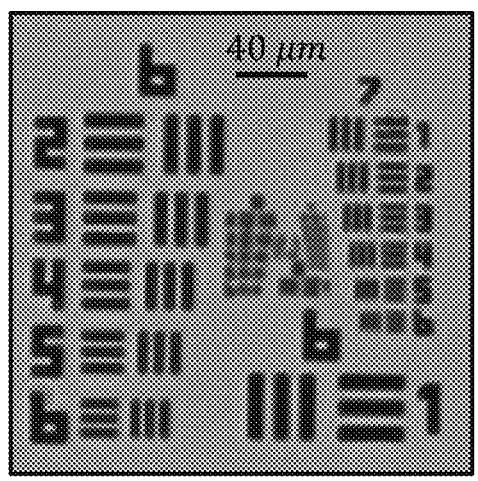
FIG. 11A is an image of a USAF target taken with a conventional microscope having a 4×/NA 0.1 objective with planar illumination.
Figure 11B:
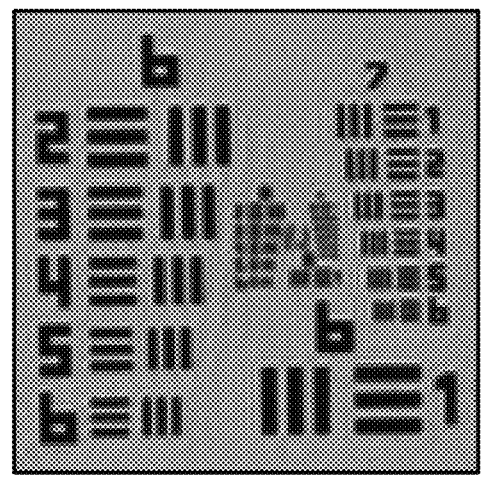
FIG. 11B is a raw intensity image of the USAF target taken by an MWB system having a 1:1 imaging configuration, according to an embodiment.

FIG. 11A is an image of a USAF target taken with a conventional microscope having a 4×/NA 0.1 objective with planar illumination. FIG. 11B is a raw intensity image of the USAF target taken by an MWB system having a 1:1 imaging configuration, according to an embodiment. This raw intensity image was based on a center LED illumination (i.e. LED located above the center of the USAF target). The smallest resolvable feature is group 7, element 5 (line width of 2.46 µm) in both cases. This indicates that the MWB system has the full field-of-view provided by the numerical aperture of the first objective lens in the 1:1 imaging configuration.

Figure 11C:
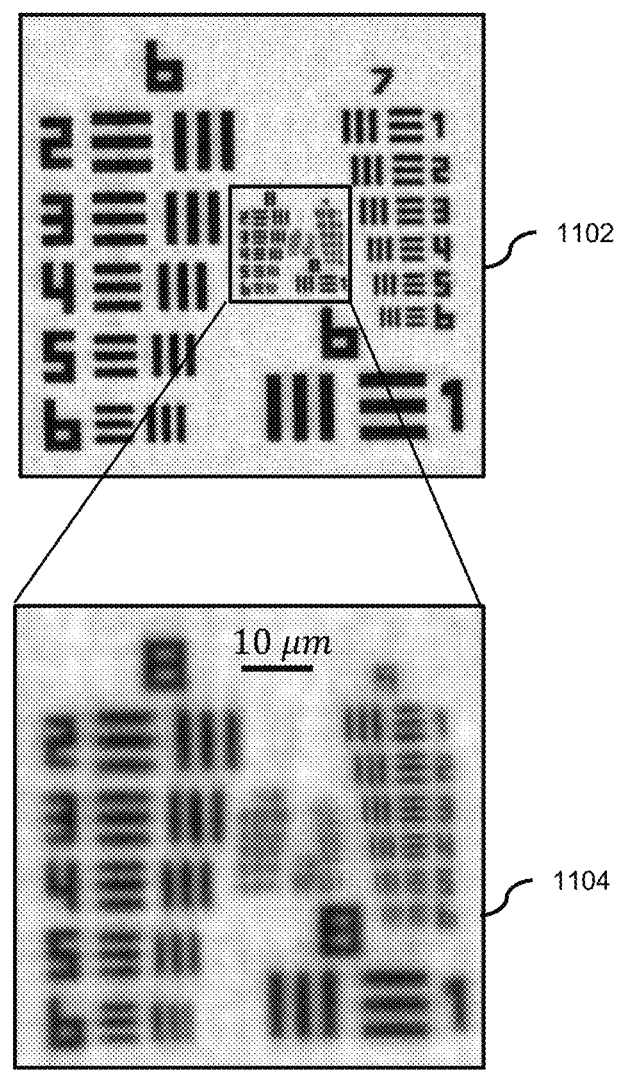
FIG. 11C includes a high resolution bright field image of a USAF target generated by an FP imaging process implemented by the MWB system, according to an embodiment.

FIG. 11C includes a high resolution bright field image 1102 of a USAF target generated by an FP imaging process implemented by the MWB system, according to an embodiment. The high resolution image was generated by combining data from 169 raw images (n=169) acquired during image acquisition of the FP construction process. The 169 raw images were acquired by sequentially illuminating 169 different LEDs of an LED matrix. Using the FP construction process with 169 raw images, the synthetic NA of the MWB system was 0.42 and the resolution of the MWB system was increased by four times, resolving the feature of group 9, element 5 (line width of 0.62 µm). FIG. 11C also includes an enlarged image 1104 of the area in the rectangle of the improved resolution bright field image 1102.

Figure 12A:
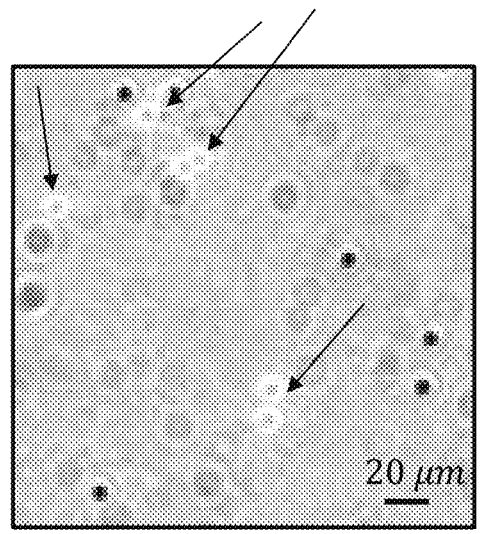
FIG. 12A is an overlay image of a low resolution brightfield image with a fluorescence image, acquired using an MWB system, according to an embodiment.
Figure 12B:
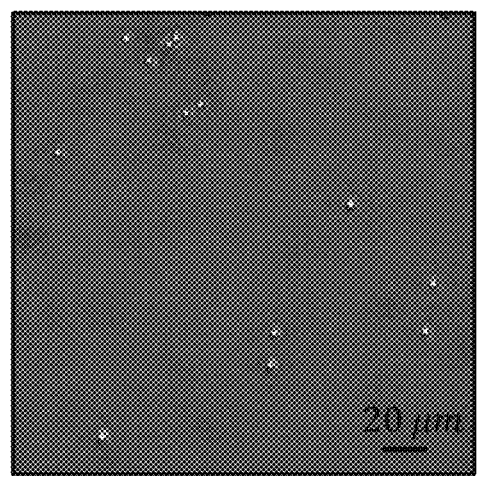
FIG. 12B is a reconstructed high resolution bright field image generated using the FP reconstruction process of the imaging method implemented by the MWB system, according to an embodiment.
Figure 12C:
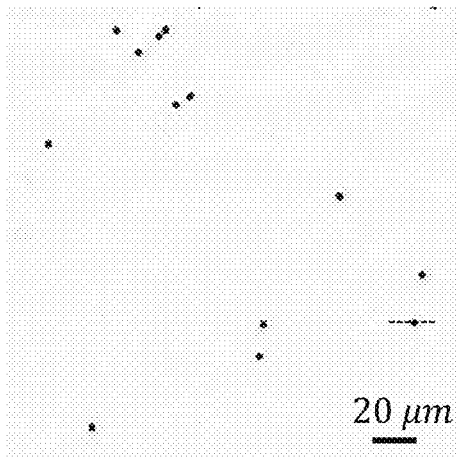
FIG. 12C is a reconstructed phase image generated using the FP reconstruction process of the imaging method implemented by the MWB system, according to an embodiment.

In FIGS. 12A, 12B, 12C, a mixture of 4.5 µm green fluorescent speeds and non-fluorescent beads were added to a sample. FIG. 12A is an overlay image of a low resolution bright-field image with a fluorescence image, acquired using an MWB system, according to an embodiment. The raw bright-field image of the sample was acquired during an FP image acquisition process of an imaging method implemented by the MWB system. The fluorescence image was generated during a fluorescence imaging process of the imaging method. In FIG. 12A, arrows are pointing to the green fluorescence beads.

FIG. 12B is a high resolution bright field image generated using the FP imaging process of the imaging method implemented by the MWB system, according to an embodiment. FIG. 12C is a reconstructed phase image generated using the FP reconstruction process of the imaging method implemented by the MWB system, according to an embodiment. As shown, the fluorescent beads are clearly distinguishable from the nonfluorescent beads by the fluorescent signal. Two beads that are attached to each other resolves from the reconstructed intensity and phase images in FIGS. 12B and 12C, and a fluorescence image in FIG. 12A gives information on which bead is fluorescence among them. In one aspect, an MWB system can be used to generate fluorescent images to identify targets labeled by, or expressing specific fluorophores, and FP reconstructed improved resolution images to compensate for the diffraction-limited fluorescence image of the targets.

Figure 12D:
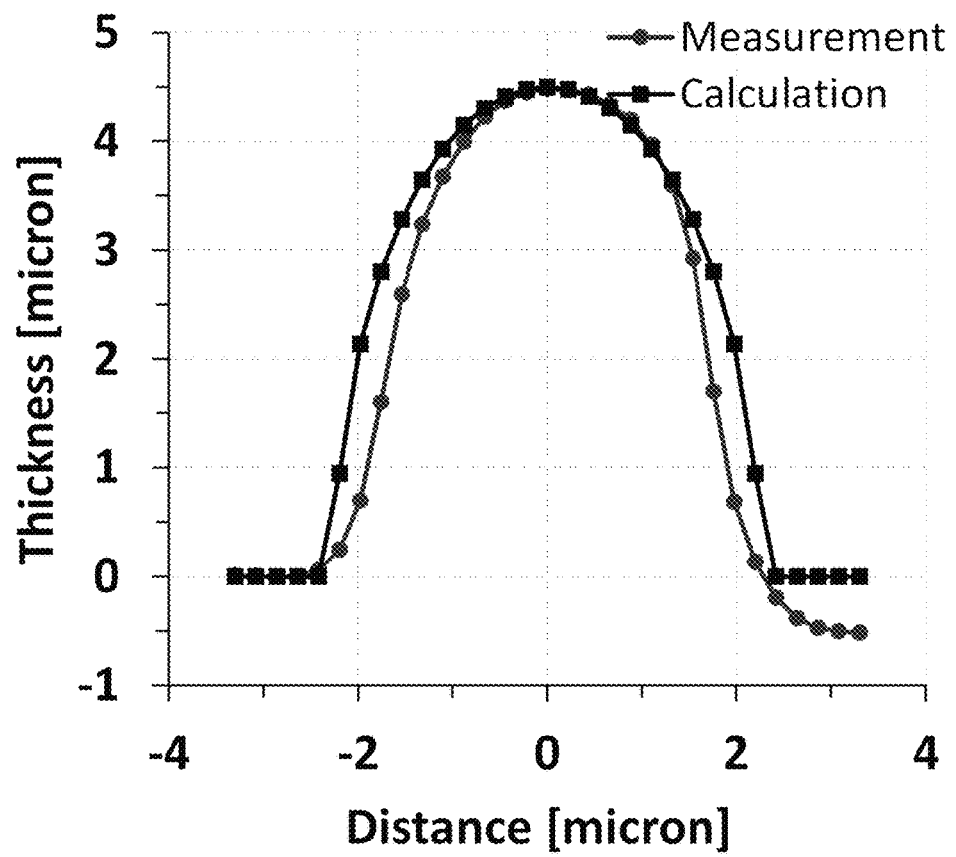
FIG. 12D is a plot of the thickness of a bead on the reconstructed phase image through a line indicated in FIG. 12C, according to an embodiment.

A complex field that contains intensity and phase information of the sample can be rendered by the iterative FP reconstruction process as discussed in X. Ou, R. Horstmeyer, C. Yang, and G. Zheng, "Quantitative phase imaging via Fourier ptychographic microscopy," Opt. Lett. 38(22), 4845-4848 (2013), which is hereby incorporated by reference for this discussion. In order to verify the quantitative accuracy of the phase information, the reconstructed phase information can be converted into the thickness of the bead using Eqn. 2:

$$T = \frac{\lambda}{2\pi} \cdot \frac{\Delta\phi}{\Delta n}, \quad \text{(Eqn. 2)}$$

where T is the thickness of the bead, λ is the wavelength of the light, Δφ is the phase relative to the background phase, and Δn is the refractive index difference between the sample and the background. In FIGS. 12A, 12B, and 12C, the polystyrene beads (n=1.58) are immersed in oil (n=1.515) and green LEDs (530 nm) are used for illumination. The converted line profile indicated in FIG. 12C is shown in FIG. 12D. FIG. 12D is a plot of the thickness of a bead on the reconstructed phase image through a line indicated in FIG. 12C. The reconstructed phase image was generated by the FP reconstruction process of the imaging method implemented by the MWB system. The measured curve closely matched the expected profile of an ideal sphere, which indicates the FPM reconstructed phase information of the MWB system is quantitatively accurate.

In one aspect, the MWB system can use the FP reconstruction process for digital refocusing. Digital refocusing is especially useful in live cell imaging, where multi-day or multi-week experiments can be vitiated by image defocus caused by system drifts and multi-well plate misalignments. By introducing a quadratic defocus phase term into the support constraint in the spatial frequency domain, the defocused raw images can be digitally re-re-focused during the FPM reconstruction as discussed in G. Zheng, R. Horstmeyer, and C. Yang, "Wide-field, high-resolution Fourier ptychographic microscopy," Nat. Photonics 7(9), 739-745 (2013).

Figure 13A:
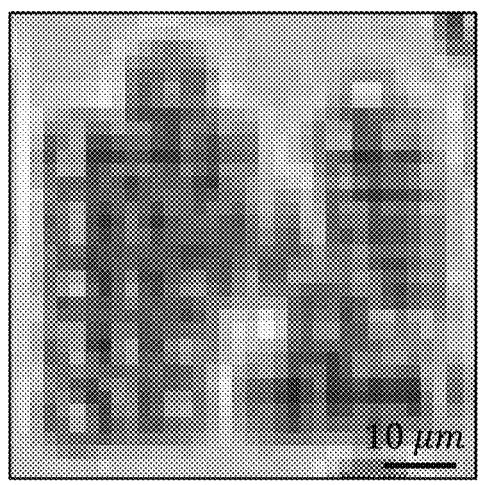
FIG. 13A is a defocused image of the USAF target at z=+100 μm.
Figure 13B:
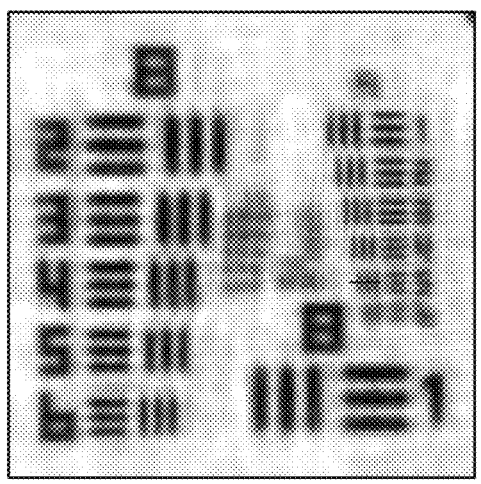
FIG. 13B is a digitally refocused image of the image shown in FIG. 13A as digitally refocused during the FP reconstruction process of an imaging method implemented by the MWB system, according to an embodiment.
Figure 14A:
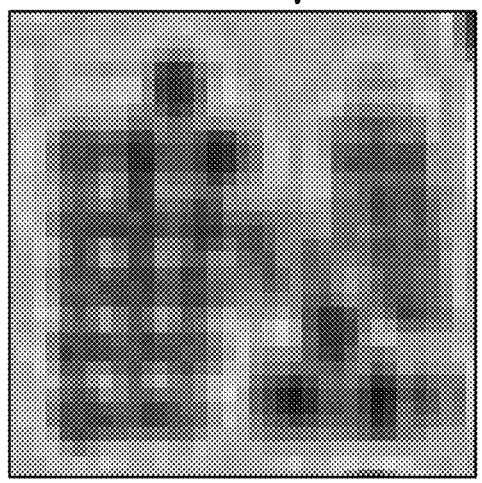
FIG. 14A is a defocused image of the USAF target at z=−100 μm.
Figure 14B:
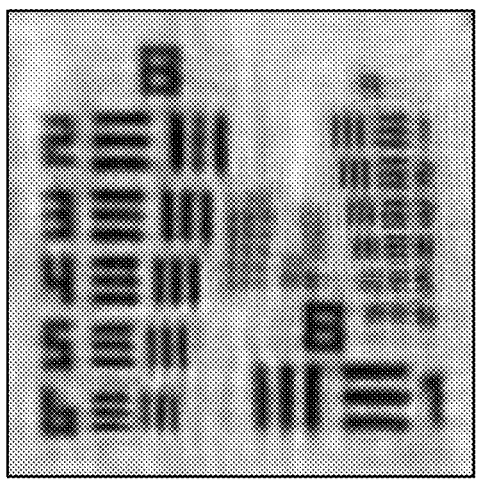
FIG. 14B is a digitally refocused image of the image shown in FIG. 14A as digitally refocused during the FP reconstruction process of an imaging method implemented by the MWB system, according to an embodiment.

In order to characterize the refocusing performance of the MWB system, a USAF target was intentionally defocused and then digitally refocused during the FP reconstruction process. FIG. 13A is a defocused image of the USAF target at z=+100 µm. FIG. 13B is a digitally refocused image of the image shown in FIG. 13A as digitally refocused during the FP reconstruction process of an imaging method implemented by the MWB system, according to an embodiment. FIG. 14A is a defocused image of the USAF target at z=−100 µm. FIG. 14B is a digitally refocused image of the image shown in FIG. 14A as digitally refocused during the FP reconstruction process of an imaging method implemented by the MWB system, according to an embodiment. As illustrated by the images in FIGS. 13B and 14B, within the defocusing range of ±100 µm, the MWB system digitally refocused the sample successfully.

Figure 15:
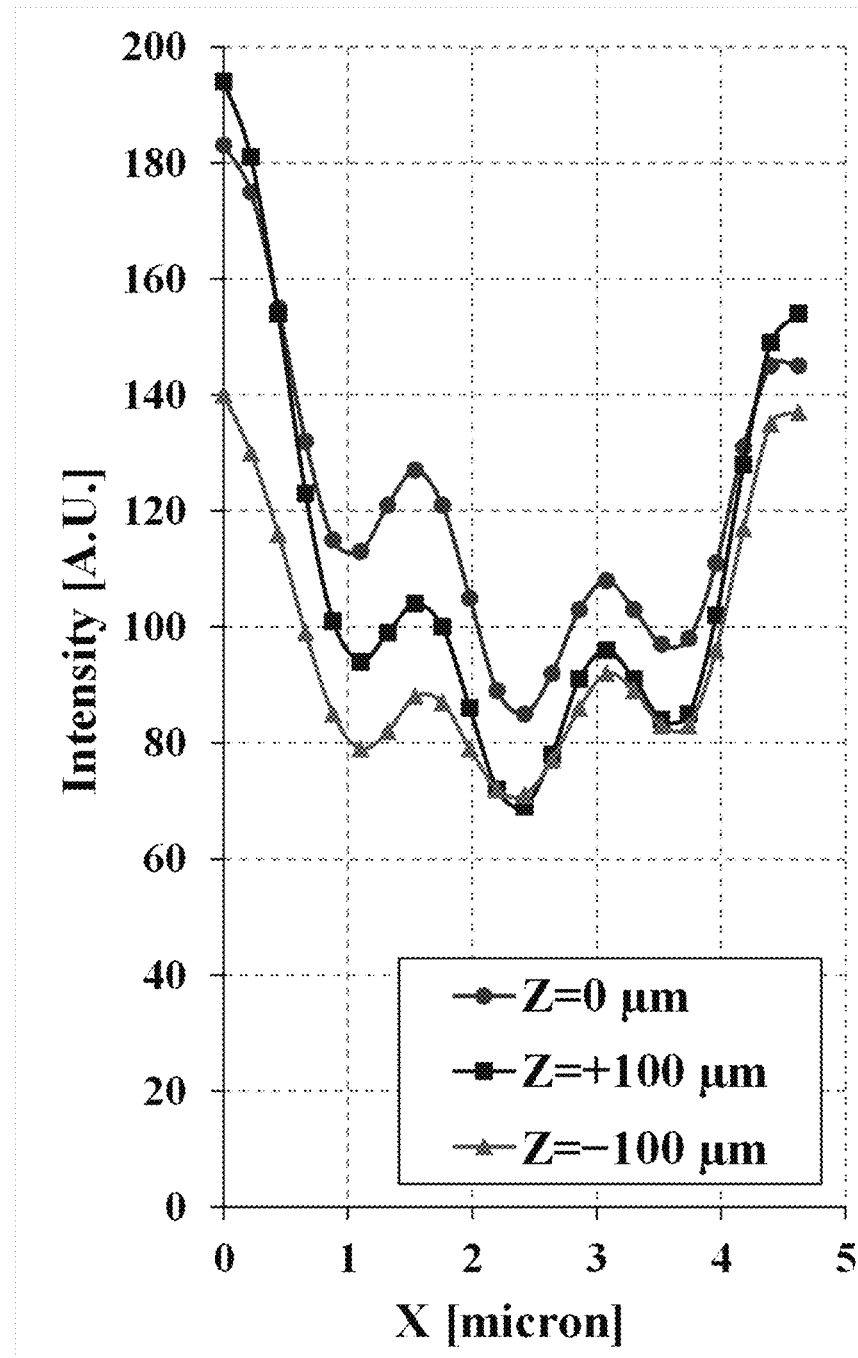
FIG. 15 is a plot of line traces of the smallest resolved features shown in FIGS. 13B and 14B, according to an embodiment.

FIG. 15 is a plot of line traces of the smallest resolved features shown in FIGS. 13B and 14B, according to an embodiment. In FIG. 15, the line traces for the smallest resolved feature in the case of the focused and z=±100 μm defocused samples are shown. Three dark lines are clearly distinguished from the line traces in all the cases, which indicates that the depth-of-field (DOF) of the MWB system is about 200 μm.

Figure 16A:
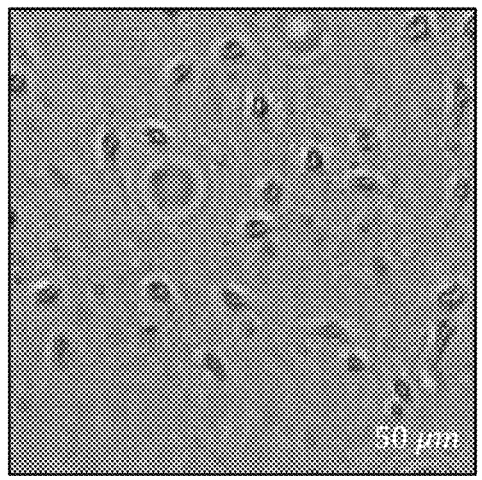
FIG. 16A is a defocused neuron culture sample image.
Figure 16B:
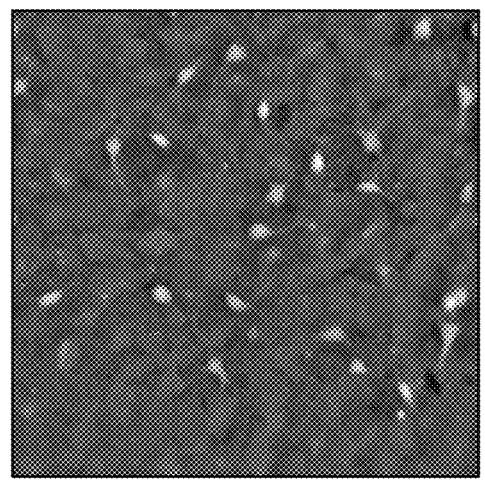
FIG. 16B is a digitally refocused phase image using FPM reconstruction of an imaging method implemented by an MWB system, according to an embodiment.

FIG. 16A is a defocused neuron culture sample image. FIG. 16B is a digitally refocused phase image using FPM reconstruction of an imaging method implemented by an MWB system, according to an embodiment. The sample used in the examples of FIGS. 16A and 16B was fixed with paraformaldehyde (PFA) and immersed in phosphate buffered saline (PBS) for the imaging.

Figure 17:
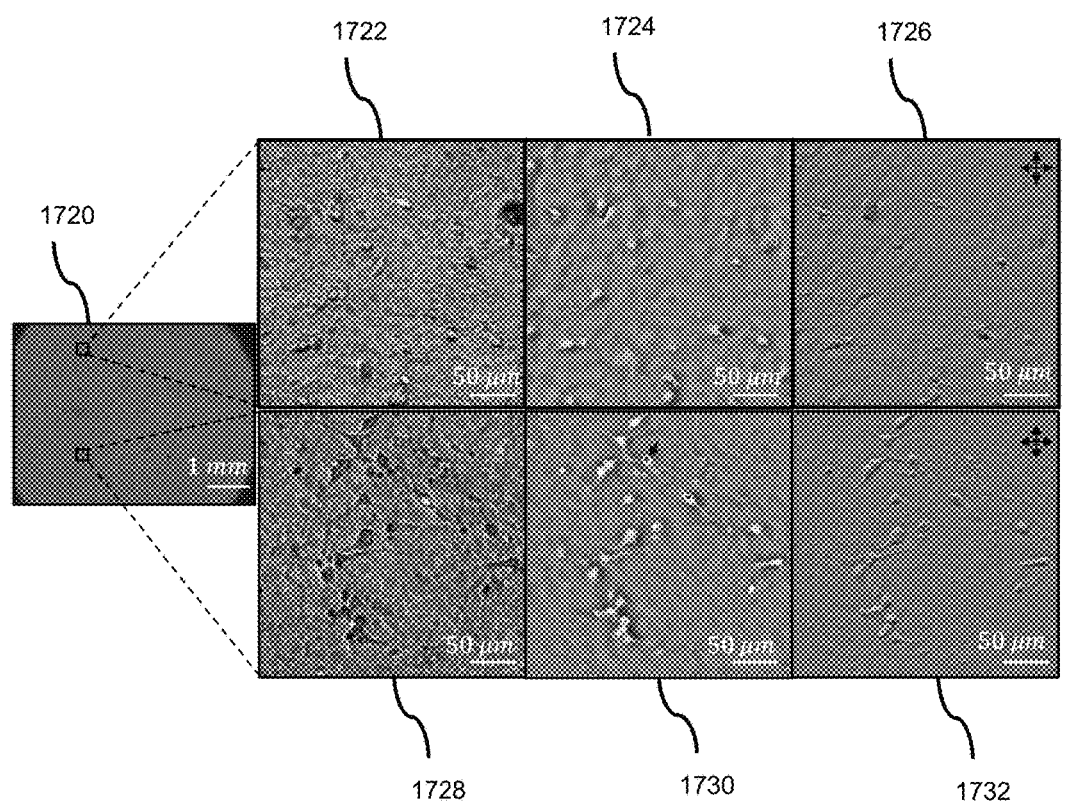
FIG. 17 shows large field-of-view images generated by an MWB system, according to an embodiment.

FIG. 17 shows large field-of-view images generated by an MWB system, according to an embodiment. Images 1722 and 1728 are raw images overlaid with fluorescence images. Images 1724 and 1730 are reconstructed phase images corresponding to images 1722 and 1728. Images 1722 and 1728 are raw images overlaid with fluorescence images. Images 1726 and 1732 are two channel phase gradient images corresponding to Images 1722 and 1728.

The full FOV of one imaging device of the MWB system was 5.7 mm×4.3 mm, as shown in the image 1720 in FIG. 17. The sample imaged was originally seeded with dopaminergic (DA) neurons that were engineered to express eGFP. 15 DA neurons were identified through the observed eGFP signals within the FOV shown in the image 1720 in FIG. 17. Images 1722, 1724, 1726, 1728, 1730, and 1732 are of two representative DA neurons. The eGFP fluorescence signal intensity from the DA neurons was strong enough to be used to identify the target cells, as shown in the images 1722 and 1728 of FIG. 17. Images 1724 and 1730 of FIG. 17 show the FPM reconstructed phase images at distances of 2.3 mm and 1.9 mm from the center of the FOV, respectively. Images 1726 and 1732 of FIG. 17 show 2 channel phase gradient images which were generated from the reconstructed phase images 1724 and 1730. The artifact caused by phase wrapping in the reconstructed phase images (indicated with arrow in image 1730) can be removed by converting the phase images into the phase gradient images.

Figure 18:
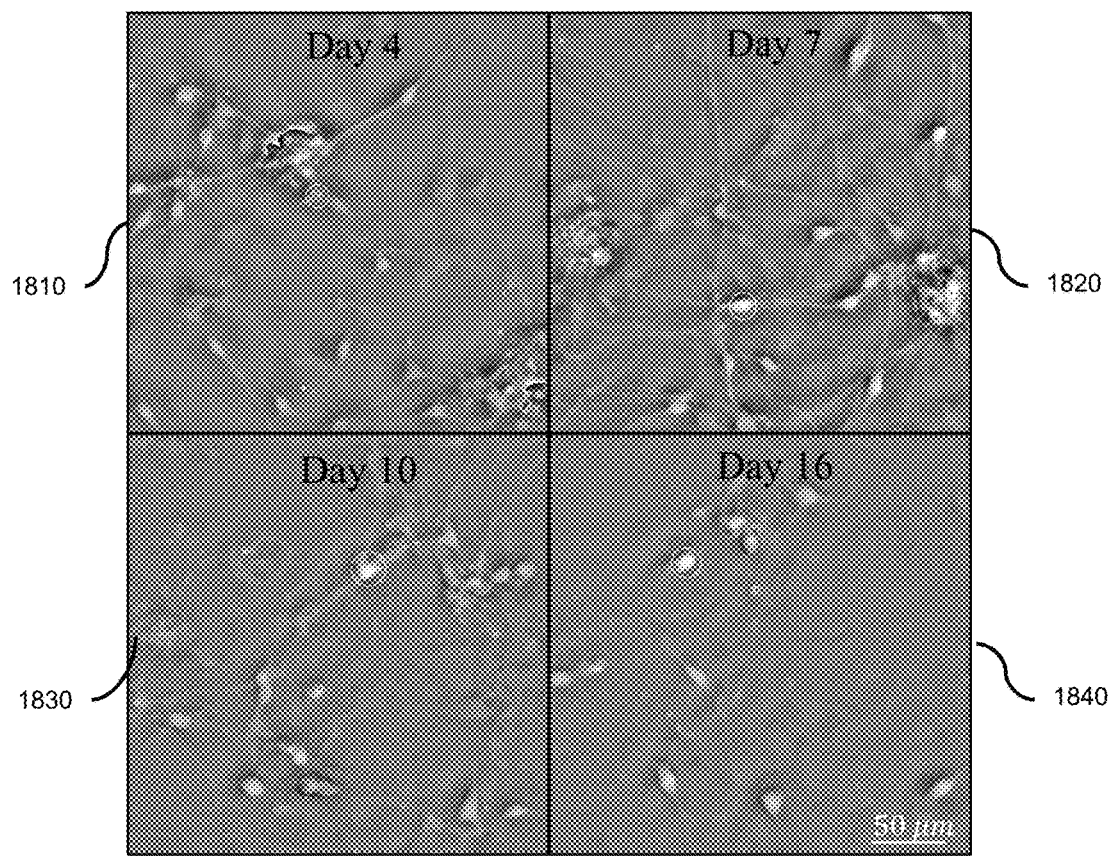
FIG. 18 is a time-lapse sequence of phase images generated by an FP process of an imaging method implemented by an MWB system, according to an embodiment.
Figure 19:
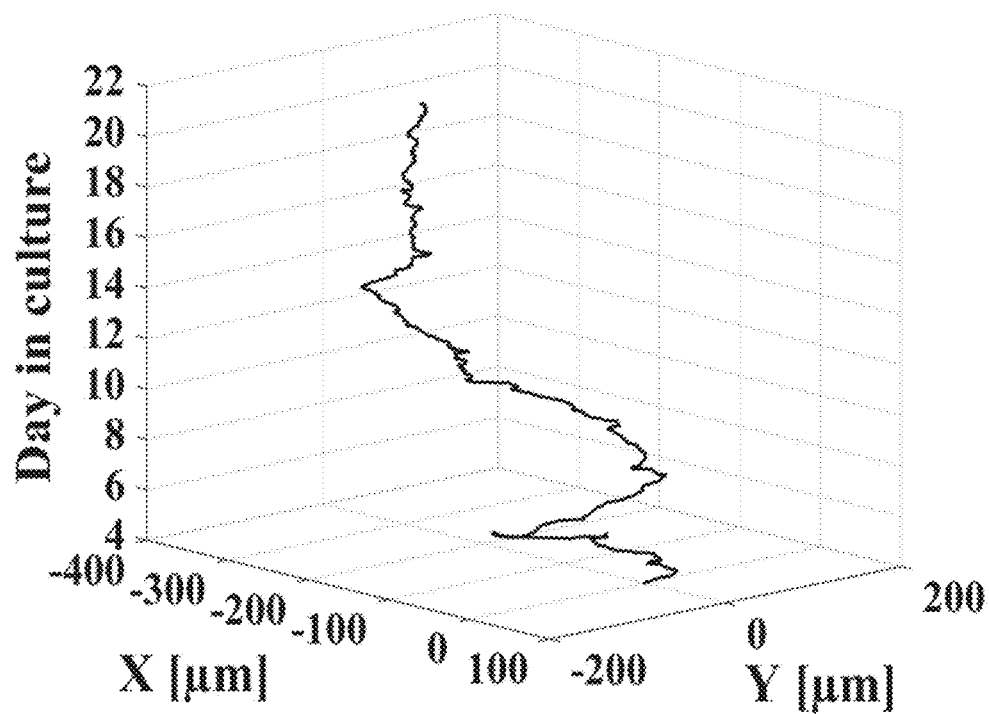
FIG. 19 is a plot of the positional trace of the tracked target cell based on images generated by an MWB system, according to an embodiment.

To conduct an example of live cell culture imaging using the MWB system, a sample was cultured of ventral midbrain from the GENSAT tyrosine hydroxylase (TH)-eGFP strain, a BAC transgenic mice line driving eGFP from the TH promoter. Each of the neuron-glia ventral midbrain cultures consisted of a glial cell monolayer, DA neurons generating TH-eGFP, and other midbrain neurons. The ventral midbrain culture was obtained from embryonic day 14 mouse embryos which were extracted from timed pregnant mice. The glial cells and midbrain neurons were grown in a 6-well plate and the culture medium was exchanged at three-day intervals over a 3-week imaging period. The MWB system was used to image and monitor the cultures in a 6-well plate over a 3-week period. The MWB system captured a sequence of n low resolution bright-field intensity images from each well at one hour intervals during the FP image acquisition process. A fluorescence imaging process was conducted once per day for each well. FIG. 18 is a time-lapse sequence of phase images 1810, 1820, 1830, and 1840 generated by an FP process of an imaging method implemented by an MWB system, according to an embodiment. The phase images 1810, 1820, 1830, and 1840 are of the mouse neuron culture discussed above. The phase images 1810, 1820, 1830, and 1840 were taken at day 4, day 7, day 10, and day 16 respectively. The tracked DA neuron is successfully identified using the eGFP fluorescence signal and marked with a yellow circle. By comparing each subsequent image, a cell was chosen having minimum position and size change with a target cell of previous time frame as a target cell of current time frame. In the one hour period time-lapse imaging, this tracking method worked well for most of cells. The target cell was tracked for the duration of the culture experiment. FIG. 19 is a plot of the positional trace of the tracked target cell based on images generated by an MWB system, according to an embodiment.

Figure 20:
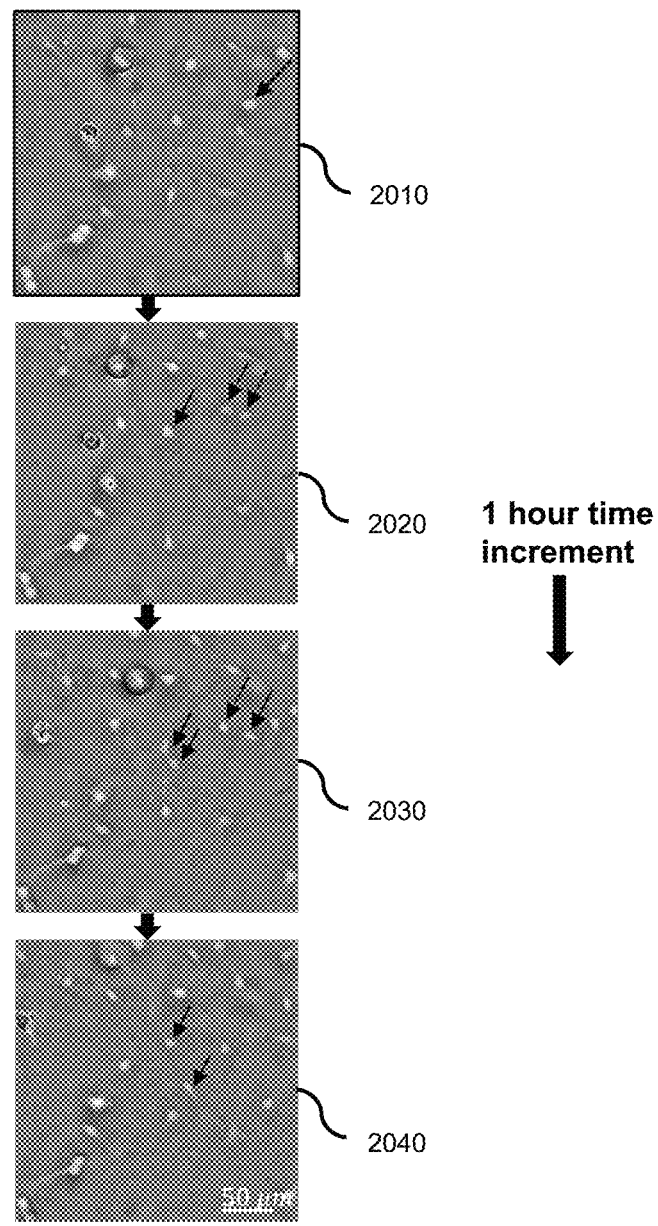
FIG. 20 is a time-lapse sequence of images generated by an FP process of an imaging method implemented by an MWB system, according to an embodiment.

FIG. 20 is a time-lapse sequence of images 2010, 2020, 2030, and 2040 generated by an FP process of an imaging method implemented by an MWB system, according to an embodiment. To conduct time-lapse imaging of dividing cells, mouse ventral midbrain cultures were mixed primary cultures. During the 21-day culture experiment, actively dividing cells were found from the time-lapse images 2010, 2020, 2030, and 2040. Two putative mother cells as indicated by the arrows divided into daughter cells. These cells began dividing on approximately day 14 of culture. Such cell divisions were observed in each of the 6 wells in the 6-well plate.

V. Subsystems

Figure 21:
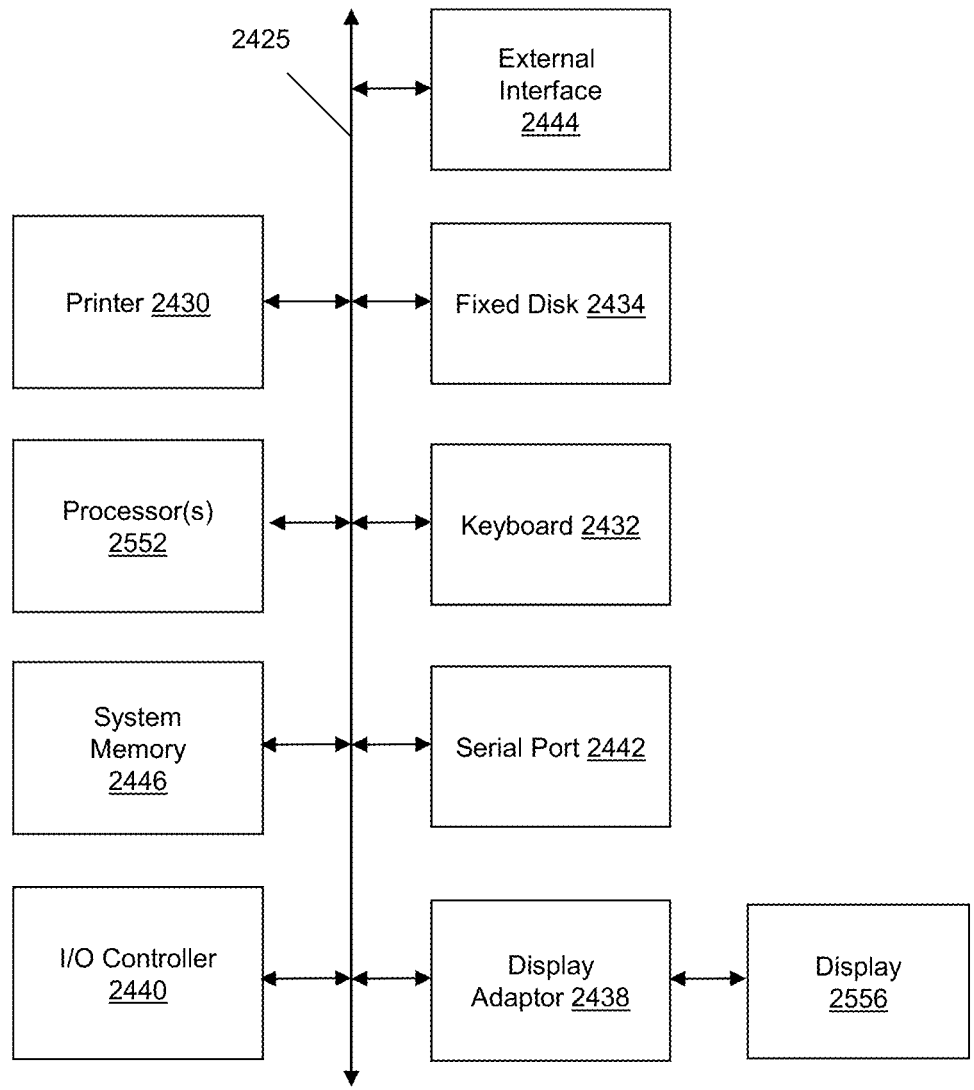
FIG. 21 is a block diagram of one or more subsystems that may be present in certain MWB systems, according to embodiments.

FIG. 21 is a block diagram of one or more subsystems that may be present in certain MWB systems, according to embodiments. A processor may be a component of the image sensor or maybe a separate component.

The various components previously described in the Figures may operate using one or more of the subsystems to facilitate the functions described herein. Any of the components in the Figures may use any suitable number of subsystems to facilitate the functions described herein. Examples of such subsystems and/or components are shown in a FIG. 21. The subsystems shown in FIG. 21 are interconnected via a system bus 2425. Additional subsystems such as a printer 2430, keyboard 2432, fixed disk 2434 (or other memory comprising computer readable media), display 56, which is coupled to display adapter 2438, and others are shown. Peripherals and input/output (I/O) devices, which couple to I/O controller 2440, can be connected by any number of means known in the art, such as serial port 2442. For example, serial port 2442 or external interface 2444 can be used to connect components of a computing device to a wide area network such as the Internet, a mouse input device, or a scanner. The interconnection via system bus 2425 allows the processor to communicate with each subsystem and to control the execution of instructions from system memory 2446 or the fixed disk 2434, as well as the exchange of information between subsystems. The system memory 2446 and/or the fixed disk 2434 may embody the CRM 182 in some cases. Any of these elements may be present in the previously described features.

In some embodiments, an output device such as the printer 2430 or display 182 of the Fourier camera system can output various forms of data. For example, the MWB system can output 2D color/monochromatic images (intensity and/or phase), data associated with these images, or other data associated with analyses performed by the MWB system.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. An imaging device for bright field Fourier ptychographic imaging and fluorescence imaging, the imaging device comprising:
   a first fluorescence illumination source configured to provide excitation light of a first range of wavelengths to a transparent well;
   an optical system having a pair of objectives, the pair of objectives comprising a first objective and a second objective positioned oppositely; and
   an image sensor configured to receive light propagated through the optical system from the transparent well, the image sensor further configured to acquire a sequence of uniquely illuminated intensity measurements of light passing through a sample being imaged during operation in the well based on sequential illumination at different illumination angles from a variable illumination source, the image sensor further configured to acquire a first fluorescence image of the sample based on light emitted by the sample in response to excitation light of the first range of wavelengths, wherein the first objective is configured to collect light from the transparent well and the second objective is configured to focus light to the image sensor.

2. The imaging device of claim 1, further comprising a processor configured to iteratively determine an improved resolution bright field image of the sample that is self-consistent with the sequence of uniquely illuminated intensity measurements.

3. The imaging device of claim 2, wherein the improved resolution bright field image of the sample and the first fluorescence image are determined on a periodic basis for time lapse imaging.

4. The imaging device of claim 1, wherein the excitation light of the first range of wavelengths and the illumination sequentially at different illumination angles are provided at different image acquisition times.

5. The imaging device of claim 1, wherein the optical system has an emission filter between the first and second objectives, the emission filter configured to block excitation light of the first range of wavelengths.

6. The imaging device of claim 5, wherein illumination from the variable illumination source is of a range of wavelengths within a passband of the emission filter.

7. The imaging device of claim 1,
   further comprising a second fluorescence illumination source configured to provide excitation light of a second range of wavelengths to the transparent well;
   wherein the image sensor is further configured to acquire a second fluorescence image of the sample based on light emitted by the sample in response to excitation light of the second range of wavelengths;
   wherein the processor is further configured to combine the first fluorescence image and the second fluorescence image to generate a multi-color fluorescence image of the sample.

8. The imaging device of claim 7, wherein the optical system has a dual band emission filter between the objectives, and wherein the dual band emission filter is configured to block excitation light of the first range of wavelengths and block excitation light of the second range of wavelengths.

9. The imaging device of claim 8, wherein illumination from the variable illumination source is of a range of wavelengths within a passband of the dual band emission filter.

10. The imaging device of claim 1, wherein wherein the first objective and the second objective have the same numerical aperture.

11. The imaging device of claim 1, wherein each objective has a numerical aperture of less than 0.55.

12. The imaging device of claim 1, wherein the first fluorescence illumination source directs excitation light of the first range of wavelengths at a small angle to a plane at a bottom surface of the transparent well and to a center of the transparent well.

13. The imaging device of claim 1, wherein the transparent well is in a multi-well plate.

14. The imaging device of claim 1, wherein the transparent well is in a 6-well plate or a 12-well plate.

15. The imaging device of claim 1, wherein the transparent well is at least 20 mm in width.

16. A system for Fourier ptychographic imaging and fluorescence imaging, the system comprising:
    a body configured to receive a multi-well plate;
    imaging devices arranged for one to one correspondence with transparent wells in the multi-well plate, each imaging device comprising:
    a first fluorescence illumination source configured to provide excitation light of a first range of wavelengths to the corresponding well;
    an optical system having a pair of objectives, the pair of objectives comprising a first objective and a second objective positioned oppositely; and
    an image sensor for capturing intensity measurements based on light received from the corresponding well, wherein the first objective is configured to collect light from the corresponding well and the second objective is configured to focus light to the image sensor; and a processor configured to generate an improved resolution brightfield image of each sample being imaged in a respective well during operation, the processor configured to generate the improved brightfield image using Fourier ptychographic reconstruction based on a sequence of uniquely illumination intensity measurements acquired during sequential illumination at different illumination angles by a variable illumination source; and wherein the system is also configured to generate a first fluorescence image of each sample being imaged based on light emitted by the sample in response to receiving excitation light of the first range of wavelengths.

17. The system of claim 16, wherein the processor is configured to iteratively determine the improved resolution bright field image that is self-consistent with the sequence of uniquely illuminated intensity measurements.

18. The system of claim 16, wherein the improved resolution bright field image of the sample and the first fluorescence image are determined on a periodic basis for time lapse imaging.

19. The system of claim 16, wherein the excitation light of the first range of wavelengths and the illumination sequentially at different illumination angles are provided at different image acquisition times.

20. The system of claim 16, wherein the optical system has an emission filter between the first and second objectives, the emission filter configured to block excitation light of the first range of wavelengths.

21. The system of claim 20, wherein illumination from the variable illumination source is of a range of wavelengths within a passband of the emission filter.

22. The system of claim 16,
wherein each imaging device further comprises a second fluorescence illumination source configured to provide excitation light of a second range of wavelengths to the corresponding transparent well;
wherein the image sensor is further configured to acquire a second fluorescence image of the sample being imaged based on light emitted by the sample in response to receiving excitation light of the second range of wavelengths; and
wherein the processor is further configured to overlay the first fluorescence image and the second fluorescence image to generate a multi-color fluorescence image of the sample.

23. The system of claim 22, wherein the optical system has a dual band emission filter between the first and second objectives, and wherein the dual band emission filter is configured to block excitation light of the first range of wavelengths and block excitation light of the second range of wavelengths.

24. The system of claim 23, wherein illumination from the variable illumination source is of a range of wavelengths within a passband of the dual band emission filter.

25. The system of claim 16, wherein the first objective and the second objective have the same numerical aperture.

26. The system of claim 16, wherein each of the first and second objectives has a numerical aperture of less than about 0.55.

27. The system of claim 16, wherein the first fluorescence illumination source directs excitation light of the first range of wavelengths at a small angle to a plane at a bottom surface of the corresponding transparent well and to a center of the corresponding transparent well.

28. The system of claim 16, wherein the first fluorescence illumination source is side mounted.

29. The system of claim 16, wherein the multi-well plate is a 6-well plate or a 12-well plate.

30. The system of claim 16, wherein each of the transparent wells is at least 20 mm in diameter.

31. An imaging method, comprising:
calibrating positions of light sources of a variable illumination source to locations of image sensors receiving light from wells in a multi-well plate;
illuminating the multi-well plate with excitation light of a first range of wavelengths;
for each well in the multi-well plate, acquiring a first fluorescence image of a sample being imaged during operation in the well;
sequentially illuminating the multi-well plate with plane wave illumination at a plurality of illumination angles using a variable illumination source;
for each well in the multi-well plate, acquiring, using an image sensor, a sequence of uniquely illuminated intensity measurements from light passing through the sample being imaged in the corresponding well based on the sequential illumination at the plurality of illumination angles; and
for each well in the multi-well plate, reconstructing with a Fourier ptychography reconstruction process an improved resolution brightfield image of the sample being imaged based on the sequence of uniquely illuminated intensity measurements.

32. The method of claim 31, wherein calibrating the positions of the light sources comprises:
illuminating a central light element of the variable illumination source providing the sequential illumination;
acquiring an intensity image from light passing through the sample being imaged in a respective well of the multi-well plate;
determining the center of the intensity image;
measuring a shift in the intensity image;
finding the central light element displacement using a lookup data; and
determining the plurality of illumination angles based on the central light displacement.

33. An imaging method, comprising:
sequentially illuminating a multi-well plate with plane wave illumination at a plurality of illumination angles using a variable illumination source;
for each well in the multi-well plate, acquiring, using an image sensor, a sequence of intensity measurements from light passing through the well based on sequential illumination at the plurality of illumination angles;
for each well in the multi-well plate, reconstructing, using a Fourier ptychography reconstruction process, an improved resolution brightfield image using the acquired sequence of intensity measurements;
illuminating the multi-well plate with excitation light of a first range of wavelengths;
for each well in the multi-well plate, acquiring, using the image sensor, a first fluorescence image based on emissions resulting from the illumination by excitation light of the first range of wavelengths;
illuminating the multi-well plate with excitation light of a second range of wavelengths; and
for each well in the multi-well plate, acquiring, using the image sensor, a second fluorescence image based on emissions resulting from the illumination by excitation light of the second range of wavelengths and overlaying the first and second fluorescence images to generate a multicolor fluorescence image.

34. The imaging device of claim 1, wherein the first fluorescence illumination source is side mounted.

35. An imaging method, comprising:
sequentially illuminating a multi-well plate with plane wave illumination at a plurality of illumination angles using a variable illumination source;
for each well in the multi-well plate, collecting light using a first objective and focusing the collected light to an imaging sensor using a second objective, the first objective and the second objective positioned oppositely;
for each well in the multi-well plate, acquiring, using the image sensor, a sequence of intensity measurements from light passing through the well based on the sequential illumination at the plurality of illumination angles;
reconstructing an improved resolution brightfield image using a Fourier ptychography reconstruction process and based on the acquired sequence of intensity measurements;
illuminating the multi-well plate with excitation light; and
for each well in the multi-well plate, acquiring, using the image sensor, a fluorescence image.

36. The imaging method of claim 35, wherein the first objective and the second objective have the same numerical aperture.

* * * * *